(12) United States Patent
Lee et al.

(10) Patent No.: US 8,206,593 B2
(45) Date of Patent: Jun. 26, 2012

(54) MICROFLUIDIC CHEMICAL REACTION CIRCUITS

(75) Inventors: Chung-cheng Lee, Irvine, CA (US);
Guodong Sui, Los Angeles, CA (US);
Arkadij Elizarov, Valley Village, CA (US); Hartmuth C. Kolb, Playa del Rey, CA (US); Jiang Huang, San Jose, CA (US); James R. Heath, South Pasadena, CA (US); Michael E. Phelps, Los Angeles, CA (US); Stephen R. Quake, Stanford, CA (US); Hsian-rong Tseng, Los Angeles, CA (US); Paul Wyatt, Tipperary (IE); Antoine Daridon, Mont-Sur-Rolle (CH)

(73) Assignees: Fluidigm Corporation, So. San Francisco, CA (US); California Institute of Technology, Pasadena, CA (US); The Regents of the University of California, Oakland, CA (US); Siemens Medical Solutions USA, Inc., Malvern, PA (US)

( * ) Notice: Subject to any disclaimer, the term of this patent is extended or adjusted under 35 U.S.C. 154(b) by 705 days.

(21) Appl. No.: 11/792,168

(22) PCT Filed: Dec. 5, 2005

(86) PCT No.: PCT/US2005/044072
§ 371 (c)(1),
(2), (4) Date: Feb. 14, 2008

(87) PCT Pub. No.: WO2006/071470
PCT Pub. Date: Jul. 6, 2006

(65) Prior Publication Data
US 2008/0281090 A1    Nov. 13, 2008

Related U.S. Application Data

(60) Provisional application No. 60/633,121, filed on Dec. 3, 2004, provisional application No. 60/721,607, filed on Sep. 29, 2005.

(51) Int. Cl.
*B01D 11/00* (2006.01)
*B01J 7/00* (2006.01)
*B01D 15/00* (2006.01)

(52) U.S. Cl. ......... 210/640; 210/634; 422/129; 422/134

(58) Field of Classification Search .................. 422/129, 422/188
See application file for complete search history.

(56) References Cited

U.S. PATENT DOCUMENTS
6,540,895 B1    4/2003    Spence et al.
(Continued)

FOREIGN PATENT DOCUMENTS
GB        0206117.4        3/2002
(Continued)

OTHER PUBLICATIONS

A. de Mello et al., "But what is it good for? Applications of microreactor technology for the fine chemical industry," Lab on a Chip 2, 7n (2002).

(Continued)

*Primary Examiner* — Krishnan S Menon
*Assistant Examiner* — Katherine Zalasky
(74) *Attorney, Agent, or Firm* — Kilpatrick Townsend & Stockton LLP

(57) ABSTRACT

New microfluidic devices, useful for carrying out chemical reactions, are provided. The devices are adapted for on-chip solvent exchange, chemical processes requiring multiple chemical reactions, and rapid concentration of reagents.

20 Claims, 23 Drawing Sheets

U.S. PATENT DOCUMENTS

| | | | |
|---|---|---|---|
| 6,885,982 | B2 | 4/2005 | Harris et al. |
| 6,951,632 | B2 | 10/2005 | Unger et al. |
| 7,042,649 | B2 | 5/2006 | Quake et al. |
| 7,059,348 | B2 | 6/2006 | Nat |
| 7,062,418 | B2 | 6/2006 | Lee et al. |
| 7,097,809 | B2 | 8/2006 | Dam et al. |
| 7,161,736 | B2 | 1/2007 | Legrand et al. |
| 7,192,629 | B2 | 3/2007 | Lammertink et al. |
| 7,217,367 | B2 | 5/2007 | Huang et al. |
| 7,232,109 | B2 | 6/2007 | Driggs et al. |
| 7,248,413 | B2 | 7/2007 | Quake et al. |
| 7,262,923 | B2 | 8/2007 | Quake et al. |
| 7,279,146 | B2 | 10/2007 | Nassef et al. |
| 7,291,512 | B2 | 11/2007 | Unger |
| 7,368,163 | B2 | 5/2008 | Huang et al. |
| 7,442,556 | B2 | 10/2008 | Manger et al. |
| 7,476,363 | B2 | 1/2009 | Unger et al. |
| 7,526,741 | B2 | 4/2009 | Lee et al. |
| 7,604,965 | B2 | 10/2009 | McBride et al. |
| 7,666,361 | B2 | 2/2010 | McBride et al. |
| 7,678,547 | B2 | 3/2010 | Eyal et al. |
| 7,691,333 | B2 | 4/2010 | McBride et al. |
| 7,749,737 | B2 | 7/2010 | McBride et al. |
| 4,565,026 | A1 | 8/2010 | Hansen et al. |
| 7,792,345 | B2 | 9/2010 | Taylor et al. |
| 7,815,868 | B1 | 10/2010 | Jones et al. |
| 7,820,427 | B2 | 10/2010 | Unger et al. |
| 7,833,708 | B2 | 11/2010 | Enzelberger et al. |
| 7,837,946 | B2 | 11/2010 | McBride et al. |
| 2004/0180377 | A1 | 9/2004 | Manger et al. |
| 2005/0053952 | A1 | 3/2005 | Hong et al. |
| 2005/0226776 | A1 | 10/2005 | Brady et al. |
| 2006/0172408 | A1 | 8/2006 | Quake et al. |
| 2006/0281183 | A1 | 12/2006 | Sun et al. |
| 2007/0134807 | A1 | 6/2007 | Bao et al. |
| 2007/0224617 | A1 | 9/2007 | Quake et al. |
| 2007/0248971 | A1 | 10/2007 | Maerkl et al. |
| 2008/0050283 | A1 | 2/2008 | Chou et al. |
| 2008/0075380 | A1 | 3/2008 | Dube et al. |
| 2008/0108063 | A1 | 5/2008 | Lucero et al. |
| 2008/0129736 | A1 | 6/2008 | Sun et al. |
| 2008/0176211 | A1 | 7/2008 | Spence et al. |
| 2008/0223721 | A1 | 9/2008 | Cohen et al. |
| 2008/0230387 | A1 | 9/2008 | McBride et al. |
| 2008/0264863 | A1 | 10/2008 | Quake et al. |
| 2008/0274493 | A1 | 11/2008 | Quake et al. |
| 2008/0281090 | A1 | 11/2008 | Lee et al. |
| 2008/0292504 | A1 | 11/2008 | Goodsaid et al. |
| 2009/0018195 | A1 | 1/2009 | Balagadde |
| 2009/0035838 | A1 | 2/2009 | Quake et al. |
| 2009/0069194 | A1 | 3/2009 | Ramakrishnan |
| 2009/0142236 | A1 | 6/2009 | Unger et al. |
| 2009/0147918 | A1 | 6/2009 | Fowler et al. |
| 2009/0239308 | A1 | 9/2009 | Dube et al. |
| 2009/0291435 | A1 | 11/2009 | Unger et al. |
| 2010/0104477 | A1 | 4/2010 | Liu et al. |
| 2010/0120018 | A1 | 5/2010 | Quake et al. |
| 2010/0120077 | A1 | 5/2010 | Daridon |
| 2010/0154890 | A1 | 6/2010 | Maerkl et al. |
| 2010/0166608 | A1 | 7/2010 | Quan et al. |
| 2010/0171954 | A1 | 7/2010 | Quake et al. |
| 2010/0183481 | A1 | 7/2010 | Facer et al. |
| 2010/0184202 | A1 | 7/2010 | McBride et al. |
| 2010/0187105 | A1 | 7/2010 | Unger et al. |
| 2010/0196892 | A1 | 8/2010 | Quake et al. |
| 2010/0197522 | A1 | 8/2010 | Liu et al. |
| 2010/0200782 | A1 | 8/2010 | Unger et al. |
| 2010/0230613 | A1 | 9/2010 | Pieprzyk et al. |
| 2010/0263732 | A1 | 10/2010 | Hansen et al. |
| 2010/0263757 | A1 | 10/2010 | Fernandes et al. |
| 2010/0311060 | A1 | 12/2010 | Facer et al. |
| 2010/0320364 | A1 | 12/2010 | Unger et al. |

FOREIGN PATENT DOCUMENTS

| | | | |
|---|---|---|---|
| WO | WO 01/67369 | A2 | 9/2001 |
| WO | WO 2004/040001 | A2 | 5/2004 |
| WO | WO 2004/059299 | A1 | 7/2004 |
| WO | WO 2004059299 | A1 * | 7/2004 |
| WO | WO 2004/093652 | A2 | 11/2004 |
| WO | WO 2004093652 | A2 * | 11/2004 |
| WO | WO 2007/033385 | A2 | 3/2007 |
| WO | WO 2007/044091 | A2 | 4/2007 |
| WO | WO 2008/043046 | A2 | 4/2008 |
| WO | WO 2009/100449 | A1 | 8/2009 |
| WO | WO 2010/011852 | A1 | 1/2010 |
| WO | WO 2010/017210 | A1 | 2/2010 |
| WO | WO 2010/077618 | A1 | 7/2010 |

OTHER PUBLICATIONS

Y. Kikutani et al., "Micro-Flow Reaction Systems for Combinatorial Syntheses," Macromolecular Rapid Communications 25, 158 (2004).

K. Jahnisch et al., "Chemistry in Microstructured Reactors," Angewandte Chemie-International Edition 43, 406 (2004).

P.D.I. Fletcher et al., "Micro reactors: principles and applications in organic synthesis," Tetrahedron 58, 4735 (2002).

O. Worz et al., "Microreactors, a new efficient tool for optimum reactor design," Chemical Engineering Science 56, 1029 (2001).

P. Watts et al., "Microfluidic combinatorial chemistry," Current Opinion in Chemical Biology 7, 380 (2003).

J. Kobayashi et al., "A Microfluidic Device for Conducting Gas-Liquid-Solid Hydrogenation Reactions," Science 304, 1305 (2004).

E.M. Chan et al., "Size-Controlled Growth of CdSe Nanocrystals in Microfluidic Reactions," Nano Letters 3, 199 (2003).

T. Kawaguchi et al., "Room-Temperature Swern Oxidations by Using a Microscale Flow System," Angewandte Chemie-International Edition 44, 2413 (2005).

J. W. Hong et al., "A nanoliter-scale nucleic acid processor with parallel architecture," Nature Biotechnology 22, 435 (2004).

M.E. Phelps, "Positron emission tomography provides molecular imaging of biological processes," Proceedings of the National Academy of Sciences of the United States of America 97, 9226 (2000).

K. Hamacher et al., "Efficient Stereospecific Synthesis of No-Carrier-Added 2-[18F]-Fluoro-2Deoxy-D-Glucose Using Aminopolyether Supported Nucleophilic Substitution," Journal of Nuclear Medicine 27, 235 (1986).

H.C. Padgett et al., "Computer-controlled Radiochemical Synthesis: A Chemistry Process Control Unit for the Automated Production of Radiochemicals," Applied Radiation and Isotopes 40, 433 (1989).

T. Thorsen et al., "Microfluidic Large-Scale Integration," Science 298, 580 (2002).

H.P. Chou et al., "A Microfabricated Rotary Pump," Biomedical Microdevices 3, 323 (2001).

N. Satyamurthy, in PET, Molecular Imaging and Its Biological Applications M. E. Phelps, Ed. (Springer-Verlag, New York, 2004) pp. 217-269.

J. P. Rolland et al., "Solvent-Resistant Photocurable "Liquid Teflon" for Microfluidic Device Fabrication," Journal of the American Chemical Society 126, 2322 (2004).

Lee et al., "Multistep synthesis of a Radiolabeled Imaging Probe Using Integrated Microfluidics," Science Dec. 16, 2005;310(5755):1793-6.

T. Vilkner et al., "Micro Total Analysis Systems. Recent Developments," Department of Chemistry, Imperial College London and ISAS—Institute for Analytical Sciences. Anal. Chemistry, 76, 3373-3386 (2004).

Shui-Yu Lu et al., "Syntheses of 11C- and 18F-labeled carboxylic esters within a hydrodynamically-driven micro-reaction," Miniaturisation for Chemistry, Biology & Bioengineering, first published as an Advance Article on the web, Sep. 28, 2004.

D. Roberge et al., "Microreactor Technology: A Revolution for the Fine Chemical and Pharmaceutical Industries?," Chem. Eng. Technol., 28, No. 3 (2005).

* cited by examiner

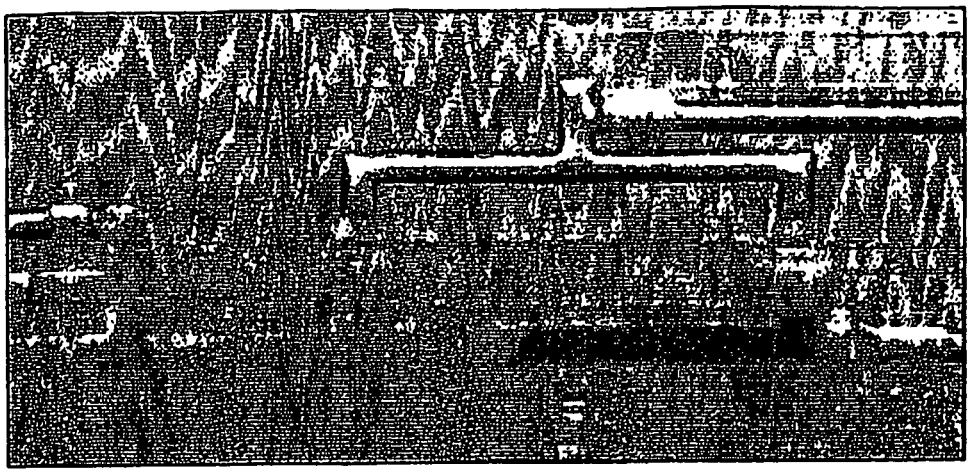
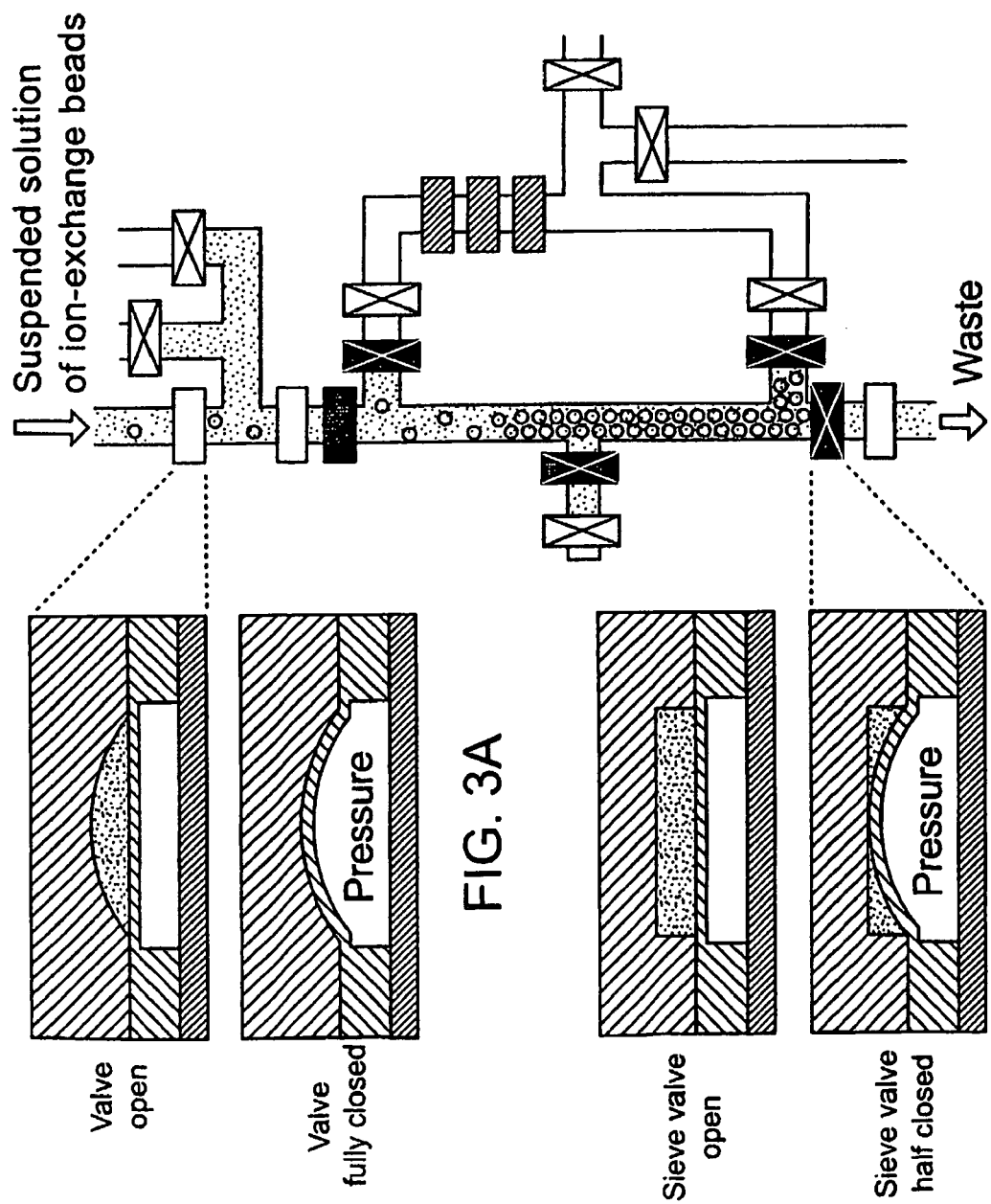
FIG. 3D
FIG. 3C
FIG. 3A
FIG. 3B

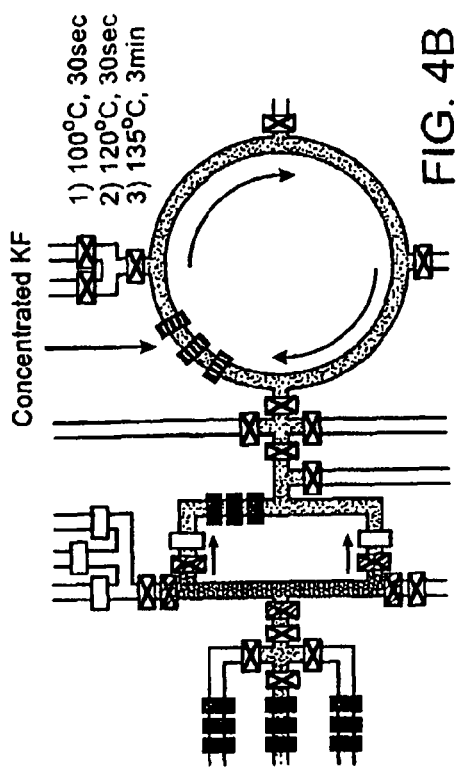
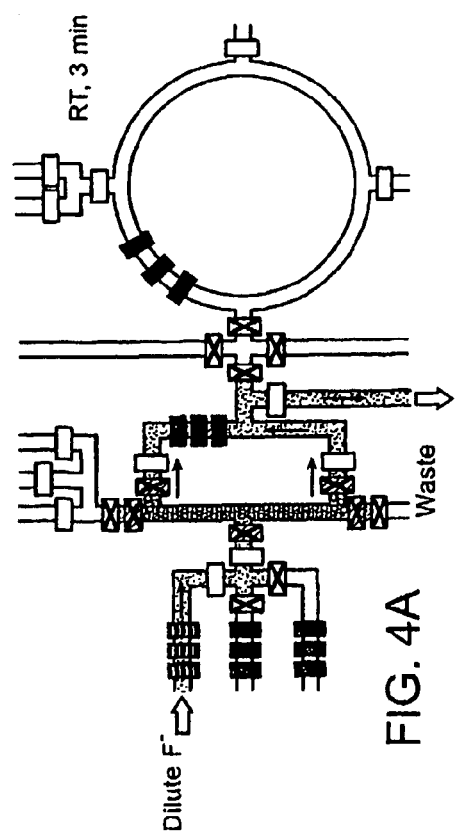
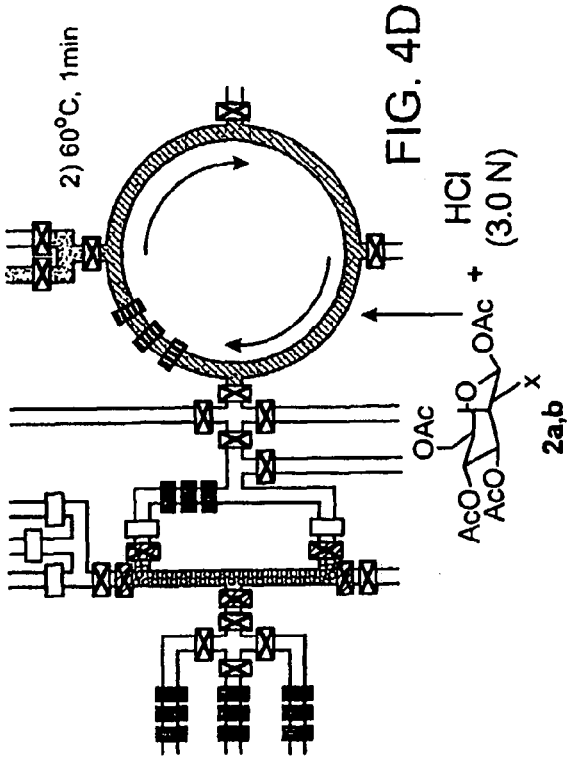
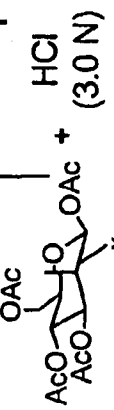
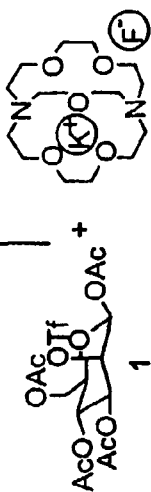
FIG. 4A  FIG. 4B  FIG. 4C  FIG. 4D

MICROFLUIDIC CHEMICAL REACTION CIRCUITS

CROSS-REFERENCE TO RELATED APPLICATIONS

This application claims benefit of U.S. Provisional Application No. 60/633,121, filed Dec. 3, 2004, and Provisional Application No. 60/721,607, filed Sep. 29, 2005, the entire contents of which are incorporated herein by reference.

STATEMENT REGARDING FEDERALLY SPONSORED RESEARCH

Work described herein has been supported, in part, by the Department of Energy (DOE grant no. DE-FC02-02ER63420-S-106,907) and the National Cancer Institute (5P50 CA086306). The United States Government may have certain rights in the invention.

FIELD OF THE INVENTION

The present inventions relate to microfabricated devices and methods for chemical synthesis using such devices. The inventions find application in the fields of microfluidics and synthetic chemistry.

BACKGROUND OF THE INVENTION

Microfluidic devices and methods are of significant and increasing importance in biomedical and pharmaceutical research. However, considerable challenges remain in applying microfluidic technology to sequential syntheses of fine chemicals and pharmaceuticals. Continuous flow microreactors have recently been used to manipulate individual chemical processes on nanoliter (nL) to microliter (μL) scales with advantages of enhanced heat transfer performance, faster diffusion times and reaction kinetics, and improved reaction product selectivity (de Mello et al., 2002, *Lab on a Chip* 2:7n; Kikutani and Kitamori, 2004, *Macromolecular Rapid Communications* 25:158; Jahnisch et al., 2004, *Angewandte Chemie-International Edition* 43:406; Fletcher et al., 2002, *Tetrahedron* 58:4735; Worz et al., 2001, *Chemical Engineering Science* 56, 1029; Watts et al. 2003, *Current Opinion in Chemical Biology* 7:380). However, in multi-step procedures, flow-through systems are plagued by cross contamination of reagents from different steps; side reactions and poor overall yield result from the inability to confine each individual step. Improved methods and devices are needed.

A compelling application for microfluidic synthesis is in the preparation of organic compounds bearing short-lived isotopes, whose emission permits detailed mapping of biological processes in living organs. See Phelps, 2000, *Proc. Nat. Acad. Sci. USA* 97: 9226. The development of sensitive radiolabeled molecular probes is crucial for expanding the capability of target-specific in vivo imaging for biological research and drug discovery. The United States already has a vast network of PET cyclotron production sites in place as convenient sources for radiolabeled precursors (e.g., $[^{18}F]$ fluoride, $[^{11}C]CO_2$ and $[^{11}C]MeI$) and a few labeled biomarkers. The capacity for diversifying radiolabeled probe structure is therefore limited only by the cost, speed, and efficiency of synthetic methods. A microfluidic device that could be used for synthesis of radiopharmaceuticals would constitute a significant advance in medicine and would provide immediate and significant benefit to patients.

BRIEF SUMMARY

In one aspect, the invention provides a method for solvent exchange using a microfluidic device by i) providing a microfluidic device comprising a reactor, where the reactor (a) is configured to fluidically communicate with at least one microfluidic channel; (b) is configured to be fluidically isolated; and (c) is defined by a wall at least a portion of which is permeable to a gas but substantially impermeable to a liquid corresponding to the gas; ii) introducing into the reactor a first solvent system comprising a first reactant; iii) fluidically isolating the reactor and withdrawing some or all of the first solvent system from the fluidically isolated reactor while retaining the first reactant in the reactor; iv) introducing into the reactor a second solvent system different from the first solvent system.

In one aspect, the invention provides a method for removing a solvent system from a microfluidic reactor by (i) providing a microfluidic device comprising a reactor, where the reactor (a) is configured to fluidically communicate with at least one microfluidic channel; (b) is configured to be fluidically isolated; and (c) is defined by a wall at least a portion of which is permeable to a gas but substantially impermeable to a liquid corresponding to the gas; where the reactor optionally contains a first solvent system and, if present, the first solvent system comprises a first solute and optionally comprised additional solutes; ii) introducing into the reactor a second solvent system comprising a second solute and optionally comprised additional solutes; iii) isolating the reactor, whereby the reactor contains a third solvent system and a solute denoted Solute A, where Solute A is first solute, the second solute, or a product of a reaction in which either or both of the first and second solutes are reactants and where the third solvent system is the same as the second solvent system or is a solvent system comprised of the combination of the first and second solvent systems; iv) withdrawing at least 25% of the volume of the third solvent system from the fluidically isolated reactor, where the third solvent system is withdrawn from the reactor more rapidly than Solute A is withdrawn, and where the amount of Solute A in the reactor per unit volume of the third solvent system in the reactor increases as the third solvent system is withdrawn. In one embodiment Solute A is in solution in the third solvent system the concentration of Solute A in the reactor increases as the third solvent system is withdrawn.

In one aspect, the invention provides a method for carrying out a chemical reaction using a microfluidic device by i) providing a microfluidic device comprising a reactor, where the reactor (a) is configured to fluidically communicate with at least one microfluidic channel; (b) is configured to be fluidically isolated; and (c) is defined by a wall at least a portion of which is permeable to a gas but substantially impermeable to a liquid corresponding to the gas; ii) introducing into the reactor a first solvent system comprising a first reactant; iii) fluidically isolating the reactor and withdrawing some or all of the first solvent system from the fluidically isolated reactor while retaining the first reactant in the reactor; iv) introducing into the reactor a second solvent system comprising a second reactant, where the first reactant and the second reactant are compounds that chemically react, under reaction conditions, to generate a product. The method may include the further steps of fluidically isolating the reactor and maintaining the reactor in a fluidically isolated state for a time and under conditions sufficient for a first reaction product to accumulate in the reactor and/or may include the further step of withdrawing some or all of the reaction solvent system from the fluidically isolated reactor while retaining the product in the reactor.

The method can include i) fluidically joining the reactor and a microfluidic channel; ii) introducing into the reactor a third solvent system comprising a third reactant and/or a catalyst, while retaining the first product in the reactor; iii) maintaining the reactor in a fluidically isolated state for a time and under conditions sufficient for a second reaction product to accumulate in the reactor. An aforementioned method can include i) fluidically joining the reactor and a microfluidic channel; ii) introducing into the reactor a third solvent system comprising a third reactant and/or a catalyst, while retaining the first product in the reactor; iii) maintaining the reactor in a fluidically isolated state for a time and under conditions sufficient for a second reaction product to accumulate in the reactor.

In one aspect, the invention provides a method for carrying out a chemical reaction using a microfluidic device by i) providing a microfluidic device comprising a reactor, where the reactor (a) is configured to fluidically communicate with at least one microfluidic channel; (b) is configured to be fluidically isolated; and (c) is defined by a wall at least a portion of which is permeable to a gas but substantially impermeable to a liquid corresponding to the gas; ii) introducing into the reactor a first solvent system comprising a first reactant; iii) introducing into the reactor a second solvent system comprising a second reactant, where the first reactant and the second reactant are compounds that chemically react, under reaction conditions, to generate a product; iv) fluidically isolating the reactor, whereby the reactor contains (1) a reaction solvent system and (2) the first and second reactants and/or the product. This method may include the steps of v) maintaining the reactor in a fluidically isolated state for a time and under conditions sufficient for a first reaction product to accumulate in the reactor; and withdrawing some or all of the reaction solvent system from the fluidically isolated reactor while retaining the product in the reactor. An aforementioned method can include i) fluidically joining the reactor and a microfluidic channel; ii) introducing into the reactor a third solvent system comprising a third reactant and/or a catalyst, while retaining the first product in the reactor; iii) maintaining the reactor in a fluidically isolated state for a time and under conditions sufficient for a second reaction product to accumulate in the reactor. In one embodiment of this method, a substantial amount of the reaction product is produced prior to step (iv). In another embodiment of this method an insubstantial amount of the reaction product is produced prior to step (iv).

In one aspect, the invention provides a method for carrying out a chemical reaction in an integrated microfluidic device by i) providing a microfluidic device comprising a reactor where the reactor (a) is configured to fluidically communicate with at least one microfluidic channel; (b) is configured to be fluidically isolated; and (c) is defined by a wall at least a portion of which is permeable to a gas but substantially impermeable to a liquid corresponding to the gas; ii) reacting a first reactant and a second reactant in the reactor, where the first and second reactants are in solution in a reaction solvent system, where the reactor is fluidically isolated, and where a first reaction product is produced; iii) evaporating at least a portion of the reaction solvent system from the fluidically isolated reactor; iv) introducing into the reactor a solution comprising a third reactant and/or a catalyst, while retaining the first product in the reactor.

In one aspect, the invention provides a method for carrying out a chemical reaction using a microfluidic device by i) providing a microfluidic device comprising a reactor, where the reactor (a) is configured to fluidically communicate with at least one microfluidic channel; (b) is configured to be fluidically isolated; and (c) is defined by a wall at least a portion of which is permeable to a gas but substantially impermeable to a liquid corresponding to the gas; ii) introducing into the reactor a first solvent system comprising a first reactant; iii) introducing into the reactor a second solvent system comprising a second reactant, where the first reactant and the second reactant are compounds that chemically react, under reaction conditions, to generate a product; iv) fluidically isolating the reactor, whereby the reactor contains 1) a reaction solvent system and 2) the first and second reactants and/or the product; where the reactor is coin-shaped and/or where vent channels are positioned adjacent over the reactor.

In one aspect, the invention provides a method for carrying out a chemical reaction in an integrated microfluidic device by (i) providing a microfluidic device comprising a reactor and a separation column comprising a stationary phase; (ii) introducing into the separation column a solution containing a first reactant, and adsorbing the first reactant to the stationary phase; (iii) eluting the first reactant from the stationary phase; (iv) introducing the first reactant into the reactor; (v) introducing the second reactant into the reactor, where the second reactant is introduced before, after, or simultaneously with the first reactant; (vi) maintaining the reactor for a time and under conditions sufficient for the first reagent and the second reagent to react and produce a first reaction product. In some embodiments, the reactor a) is configured to fluidically communicate with at least one microfluidic channel; b) is configured to be fluidically isolated; and c) is defined by a wall at least a portion of which is permeable to a gas but substantially impermeable to a liquid corresponding to the gas.

In one aspect, the invention provides a method for carrying out sequential chemical reactions using an integrated microfluidic device by i) providing a microfluidic device comprising a reactor and providing reagents sufficient for carrying out at least two sequential chemical reactions; ii) carrying out a first chemical reaction in the reactor, thereby producing a product; iii) carrying out a second chemical reaction in the reactor, where the product from (ii) is a reactant in the second chemical reaction and where the product from (ii) is not removed from the reactor prior to step (iii).

In certain embodiments of the aforementioned methods, the first reactant or the second reactant is purified or concentrated in an on-chip microfluidic separation column prior to being introduced into the reactor. In certain embodiments the separation column is an ion exchange column, such as an ion exchange column that binds the a reactant. In an embodiment the separation column is an anion exchange column and the first reactant is $^{18}$F[fluoride]. In certain embodiments the separation column is a sieve column. In certain embodiments the first or second reactant is first bound to the stationary phase of the column in a binding step and then eluted from the stationary phase of the column in an elution step prior to being introduced into the reactor. In certain embodiments the microfluidic device has a closed flow path defined by the separation column and one or more flow channel(s) and the binding step comprises circulating a solution comprising the first or second reactant through the column at least twice. In some cases the microfluidic device has a closed flow path defined by the separation column and one or more flow channel(s) and the eluting step comprises circulating an elution solution through the column at least twice.

In certain embodiments of the aforementioned methods, the first and second chemical reactions are carried out in different solvent systems. In certain embodiments of the aforementioned methods, the first solvent system and second solvent system are introduced simultaneously. In certain embodiments of the aforementioned methods, the reactor is not a closed loop. In certain embodiments of the aforementioned methods, the reactor is coin-shaped.

In certain embodiments of the aforementioned methods, the reactor has a fluid capacity of at least 4 ul. In certain embodiments of the aforementioned methods, the reactor is heated to produce reaction conditions that result in generation of the product. For example, in some cases the reactor contains a reaction solvent system and the reaction solvent system is heated to a temperature higher than the normal atmospheric boiling point of the reaction solvent system.

In certain embodiments of the aforementioned methods, the reactor is configured to fluidically communicate with at least one flow channel that is a distribution manifold. In certain embodiments of the invention, such as aspects and embodiments above, the microfluidic device reactor is not configured be fluidically isolated and/or is not defined by a wall at least a portion of which is permeable to a gas but substantially impermeable to a liquid corresponding to the gas.

In one aspect, the invention provides a method for carrying out a series of chemical reactions using a microfluidic device by i) providing a microfluidic device comprising a reactor, where the reactor (a) is configured to fluidically communicate with at least one microfluidic channel; (b) is configured to be fluidically isolated; and (c) is defined by a wall at least a portion of which is substantially impermeable to liquid water and liquid acetonitrile, but permeable to water vapor and acetonitrile vapor; ii) introducing into the reactor an aqueous solution comprising [$^{18}$F]fluoride; iii) introducing into the reactor an acetonitrile solution comprising mannose triflate; iv) fluidically isolating the reactor; v) reacting the [$^{18}$F]fluoride and the mannose triflate to produce 2-deoxy-2-$^{18}$F-fluoro-1,3,4,6-tetra-O-acetyl-beta-D-glucose; vi) fluidically joining the reactor and a microfluidic channel; vii) introducing aqueous HCl into the reactor while retaining the 2-deoxy-2-$^{18}$F-fluoro-1,3,4,6-tetra-O-acetyl-beta-D-glucose in the reactor; viii) fluidically isolating the reactor; ix) hydrolyzing the 2-deoxy-2-$^{18}$F-fluoro-1,3,4,6-tetra-O-acetyl-beta-D-glucose to produce 18F-FDG. In some embodiments, the method includes (a) introducing [$^{18}$F]Fluorine into the reactor in an aqueous solvent system; (b) removing the aqueous solvent system and replacing it with acetonitrile; and (c) introducing an acetonitrile solution of mannose triflate into the reactor, prior to step (ii). In some embodiments the microfluidic device includes a microfluidic separation column; has a closed flow path defined by the separation column and one or more flow channel(s); and the binding step includes circulating a solution comprising the first or second reactant through the column at least twice.

The method of claim where the [$^{18}$F]fluoride is first bound to the stationary phase of the column in a binding step and then eluted from the stationary phase of the column in an elution step prior to being introduced into the reactor, and where the binding step comprises circulating a solution comprising the first or second reactant through the column at least twice and/or the eluting step comprises circulating an elution solution through the column at least twice.

In another aspect, the invention provides a microfluidic device that includes a separation column comprising an immobile phase through which a fluid can pass, the column having an inlet and an outlet; and one or more flow channel(s) not comprising the solid phase; where the flow channel(s) and separation column define a closed path. In some embodiments the device includes a peristaltic pump capable of moving fluid through the closed path. In some embodiments the device includes a reactor configured to be in fluidic communication with one of the one or more flow channels.

In another aspect, the invention provides a microfluidic device having a reactor, where the reactor i) does not form a closed path; ii) can be fluidically isolated; iii) has a liquid capacity of from 5 microliters to 10 microliters. In some embodiments the device has from 1 to 5 reactors. In some embodiments the device has a single reactor. In some embodiments the device has a coin-shaped reactor. In some embodiments the device has a reactor is configured to fluidically communicate with at least one flow channel that is a distribution manifold.

In one aspect, the invention provides a method for removing solvent from a reaction chamber (reactor) of a microfluidic device, the method by providing a microfluidic device comprising a reactor that contains a solute compound and a solvent system and removing all or a portion of the solvent system while retaining the solute compound in the reactor, whereby the amount of the solute compound per unit volume of the solvent is increased. In some embodiments the solute compound remains in solution and the concentration of the solute in the solution is increased. In some embodiments at least 50% of the solvent system is removed from the reactor. In some embodiments at least 95% of the solvent system remains in the reactor. In some embodiments the solvent is water while in others the solvent is other than water. In some embodiments the solute compound comprises a radionuclide or a molecule comprising a radionuclide. For example, the radionuclide is [$^{11}$C], [$^{124}$I], [$^{18}$F], [$^{124}$I], [$^{13}$N], [$^{52}$Fe], [$^{55}$Co], [$^{75}$Br], [$^{76}$Br], [$^{94}$Tc], [$^{111}$In], [$^{99}$Tc], [$^{111}$In], [$^{67}$Ga], [$^{123}$I], [$^{125}$I], [$^{14}$C], or [$^{32}$P]. In an embodiment the solute compound is [$^{18}$F]fluoride or [$^{18}$F]-potassium fluoride. In an embodiment the solute compound is i) 2-deoxy-2-$^{18}$F-fluoro-1,3,4,6-tetra-O-acetyl-beta-D-glucose; ii) 2-(1-{6-[(2-(p-toluenesulfonyloxy)ethyl)(methyl)amino]-2-napthyl}ethylidine)malononitrile; or iii) D-mannose triflate. In one embodiment the solute compound is a cryptand, for example 4,7,13,16,21,24-Hexaoxa-1,10-diazabicyclo[8.8.8]hexacosane.

In one aspect, the invention provides a method for synthesizing a radiolabeled product in a microfluidic environment by mixing a radiolabled reactant with a precursor reactant compound to produce a radiolabeled product, where the mixing and reacting occurs in a microfluidic reactor and where the radiolabled reagent is introduced into the reactor in a first solvent and the radiolabeled precursor is introduced in a second solvent that is different from the first. In an embodiment the radiolabeled reactant is [$^{18}$F]-potassium fluoride and the precursor reactant is 2-(1-{6-[(2-(p-toluenesulfonyloxy)ethyl)(methyl)amino]-2-napthyl}ethylidine)malononitrile or D-mannose triflate. In an embodiment, the radiolabeled product is a radiolabeled molecular imaging probe. In an embodiment the precursor reactant is D-mannose triflate; 2-(1-{6-[(2-[(p-toluenesulfonyloxy)ethyl)(methyl)amino]-2-naphthyl}ethylidine)malononitrile; N-Boc-5'-O-dimethoxytrityl-3'-O-(4-nitrophenylsulfonyl)-thymidine; N2-(p-anisyldiphenylmethyl)-9-[(4-p-toluenes-ulfonyloxy)-3-(p-anisyldiphenylmethoxymethyl)butyl]guanine; N2-(p-anisyldiphenylmethyl)-9-[[1-[(.beta.-anisy-ldiphenyl-methoxy)-3-(p-toluenesulfonyloxy)-2-propoxy]methyl] guanine; 8-[4-(4-fluorophenyl)-4,4-(ethylenedioxy)bu-tyl]-3-[2'-(2,4,6-trimethylphenylsulfonyloxyethyl)]-1-phenyl-1,3,8-triazas-piro[4.5]decan-4-one; 5'-O-Boc-2,3'anhydrothymidine; N-[2-[4-(2-methoxyphenyl)-1-piperazinyl]ethyl-1]-4-nitro-N-2-pyridinyl-benzamide; 1,2- bis(tosyloxy)ethane and N,N-dimethylethanolamine; ditosylmethane or N,N-dimethylethanol amine.

In certain embodiments, an aforementioned method includes the further step of concentration of the radioactive reactant and/or deprotection or chemical modification of the radiolabeled product to produce a radiodiagnostic agent or radiotherapeutic agent.

In various aspects of the invention, a radiolabeled molecular imaging probe or a precursor of a radiolabeled molecular imaging probe is produced, such as 2-deoxy-2-[$^{18}$F]fluoro-D-glucose ([$^{18}$F]FDG); 6-[$^{18}$F]fluoro-L-3,4-dihydroxyphenylalanine ([$^{18}$F]FDOPA); 6-[$^{18}$F]fluoro-L-meta-tyrosine ([$^{18}$F]FMT), 9-[4-[$^{18}$F]fluoro-3-(hydroxymethyl)butyl]guanine ([$^{18}$F]FHBG), 9-[(3-[$^{18}$F]fluoro-1-hydroxy-2-propoxy)methyl]guanine([$^{18}$F]FHPG), 3-(2'-[$^{18}$F]fluoroethyl)spiperone([$^{18}$F]FESP), 3'-deoxy-3'-[$^{18}$F]fluorothymidine([$^{18}$F]FLT), 4-[$^{18}$F]fluoro-N-[2-[1-(2-methoxyphenyl)-1-piperazinyl]ethyl]-N-2-pyr-idinyl-benzamide([$^{18}$F]p-MPPF), 2-(1-{6-[(2-[$^{18}$F]fluoroethyl)(met-hyl)amino]-2-naphthyl}ethylidine)malononitrile([$^{18}$F]FDDNP), 2-[$^{18}$F]fluoro-alpha-methyltyrosine, [$^{18}$F]fluoromisonidazole([$^{18}$F]FMISO), 5-[$^{18}$F]fluoro-2'-deoxyuridine([$^{18}$F]FdUrd), [$^{11}$C]raclopride, [$^{11}$C]N-methylspiperone, [$^{11}$C]cocaine, [$^{11}$C]nomifensine, [$^{11}$C]deprenyl, [$^{11}$C]clozapine, [$^{11}$C]methionine, [$^{11}$C]choline, [$^{11}$C]thymidine, [$^{11}$C]flumazenil, [$^{11}$C]alpha-aminoisobutyric acid or a protected form of any of the foregoing compounds.

BRIEF DESCRIPTION OF THE FIGURES

FIG. 3. Schematic representations illustrate the operation mechanisms of (A) a regular valve having a round-profiled fluidic channel and (B) a sieve valve having a rectangular-profiled fluidic channel. When pressure is introduced into the control channels, the elastic membranes expand into the fluidic channels. In a regular valve, the fluidic channel is completely sealed because of the perfect fit between the expanded membranes and the round profile of the fluidic channel. In a sieve valve, the square-profiled fluidic channel is only partially closed, which allows fluid to flow through the two edges. Sieve valves can be used to confine solid objects within the fluidic channel, but allow liquid to flow through it. (C) Schematic illustration of the loading of anion exchange beads into a column module incorporating one fluidic channel and five sieve and five regular valves. [☐], open valve; [X], closed valve. A suspended solution of anion exchange beads is introduced into the column modules where five sieve valves and five regular valves operate cooperatively to trap anion exchange beads inside the fluidic channel (total volume: 10 nL). A miniaturized anion exchange column for fluoride concentration is achieved when the fluidic channel is fully loaded. (D) A snapshot of the bead-loading process in action.

FIG. 4. Schematic diagrams show the four most critical steps of FDG (3a,b) production in the CRC. (A) Concentration of dilute fluoride ion: with the cooperation of regular valves, a dilute fluoride solution (indicated in blue) is introduced into the ion exchange column by a metering pump. (B) Evaporating water from the concentrated KF solution: after transferring the concentrated KF solution from the fluoride concentration loop to the circular-shaped reaction loop, the CRC is heated on a hotplate to evaporate water from the reaction loop. Meanwhile, all of the surrounding regular valves are completely closed and the circulating pump is turned on. (C) Fluorination reaction: after introducing a MeCN solution (green) of Kryptofix and the D-mannose triflate 1 into the reaction loop, the inhomogeneous reaction mixture was isolated in the reaction loop, mixed using the circulating pump, and heated under a computer-controlled gradient to generate the intermediate 2a (or 2b). (D) Hydrolysis reaction: after evaporating the MeCN, an HCl solution (blue) is introduced into the reaction loop to hydrolyze the intermediate 2a (or 2b) to give the final product, FDG (3a,b).

FIG. 14 also indicates that a lower channel can be used for introduction of HCl. The synthesis of FDDNP did not require a hydrolysis step. However, the same chip design has been used for a synthesis of 3'-deoxy-3'-[18F]fluorothymidine("[$^{18}$F]FLT") which does include an acid hydrolysis step. In that case, acid can be introduced as indicated.

DETAILED DESCRIPTION

Section 1. Definitions

Figure 1:
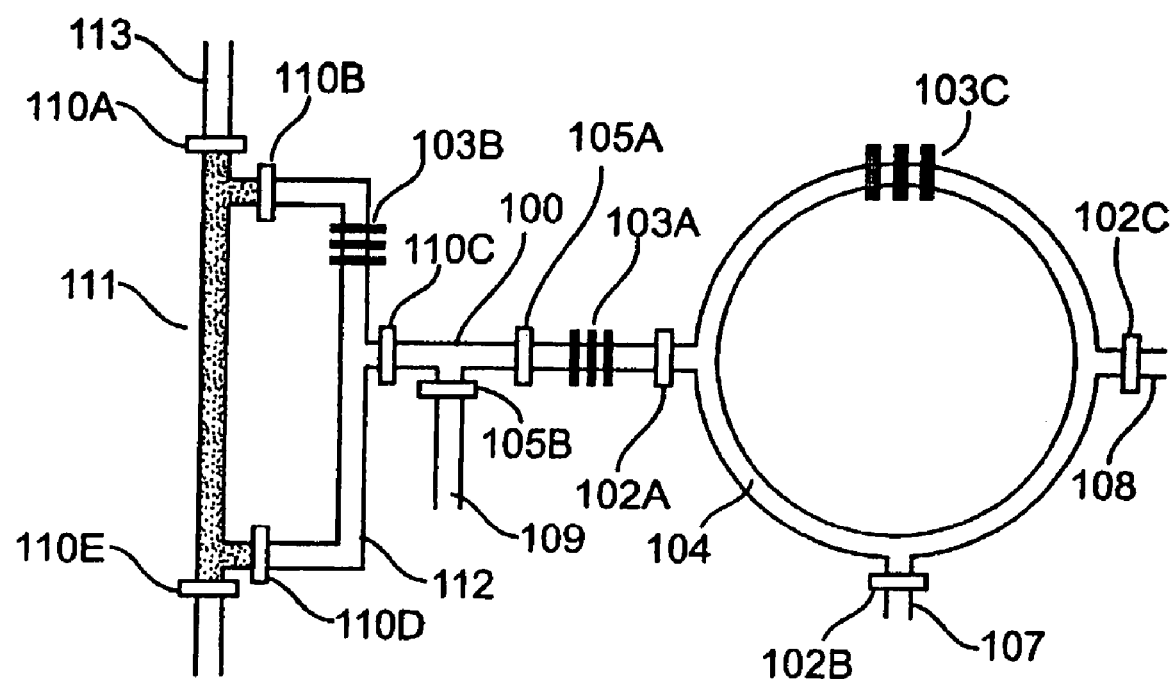
FIG. 1 provides a schematic diagram of a device for synthesis of the radioimaging agent [$^{18}$F]FDG.

As used herein, "fluid" refers to a liquid capable of flowing through a microchannel (or "flow channel;" see description in Section 3B, below) having at least one cross-sectional dimension less than 1 mm. For purposes of this disclosure, the term "fluid" does not encompasses gasses.

As used herein, the terms "microfluidic device," "integrated microfluidic device," and "chip," are used interchangeably to refer to a single integral unit that has a microfluidic reactor, microfluidic flow channels, and valves. Microfluidic devices typically also have other microfluidic components, such as pumps, columns, mixers, and the like. Most often the chip is fabricated from elastomer, glass, or silicon. Typically, the chip is box-shaped with a height that is relatively small compared to length and width; however, the chip can have other shapes including cubical, cylindrical, and others.

As used herein, the term "Chemical Reaction Circuit (CRC)," refers to a chip that contains a microfluidic reactor, flow channels, and valves, and has an architecture that renders the chip useful for carrying out sequential chemical reactions.

As used herein, a "microfluidic system" refers to a system for carrying out sequential chemical reactions, and comprises at least one microfluidic device (e.g., CRC) as well as one or more components external to the device(s). Examples of external components include external sensors, external chromatography columns, actuators (e.g., pumps or syringes), control systems for actuating valves, data storage systems, reagent storage units (reservoirs), detection and analysis devices (e.g., a mass spectrophotometer), and other components known in the art.

The terms "fluidic communication," "configured to fluidically communicate," "configured to be fluidically isolated" "fluidically isolated," and "fluidically joined," describe relationships between components of a microfluidic system, and particularly the relationship of flow channels and valves with a reactor, or the relationship of flow channels and valves with a microfluidic column.

As used herein, "fluidic communication" has its usual meaning in the microfluidic arts. Two chip components are in "fluidic communication" when a fluid can be transported (e.g., pumped) from one component to the other. For example a reactor and a flow channel are in fluidic communication when the flow channel connects to the reactor and any valve(s) that would prevent transport of a liquid from the reactor to the channel are in an "open" position. Likewise, a reactor and column that are connected by a flow channel are in fluidic communication when any valve(s) that would prevent transport of a liquid from the reactor to the column are in an "open" position.

The terms "configured to fluidically communicate" and "configured to be fluidically isolated," as used herein, refer to the presence of valves positioned or situated to prevent or permit transport of fluid from one chip component to another. Two components are "configured to fluidically communicate" if fluid could be transported from one component to the other provided any valves that would prevent flow between the components when closed are open. "Configured to fluidically communicate" refers to relationship between microfluidic components that give them the potential of being in fluidic communication, although two components "configured to fluidically communicate" may or may not be in actual fluidic communication.

A reactor is "configured to be fluidically isolated" when valves are positioned such that, if they were closed, the reactor would not be in fluidic communication with any other chip component (i.e., fluid would be confined to the reactor). Thus, a reactor that is "configured to be fluidically isolated" has the potential (if appropriate valves are closed) to be in fluidic communication with other chip components, such as flow channels and has valves positioned so that, if closed, the reactor is not in fluidic communication with other components. Chip components other than reactors can also be "configured to be fluidically isolated," i.e., when valves are positioned such that, if they were closed, the component would not be in fluidic communication with any other chip component (i.e., fluid would be confined to the fluidically isolated component). A reactor or other component that is configured to be fluidically isolated is "fluidically isolated" when the reactor or component is not in fluidic communication with any another component (e.g., valves are closed) and is "fluidically joined" when at least one valve is open and the reactor or component is in fluidic communication with at least one another component.

The term "fluidically isolating" refers to the process in which valves are closed (actuated) to change the state of a reactor or other component from fluidically joined to fluidically isolated. The term "fluidically joining" refers to the process in which valves are opened to change the state of a reactor or other component from fluidically isolated to fluidically joined.

In the special case in which one-way valves are used, the terms "fluidic communication," "configured to fluidically communicate," "configured to be fluidically isolated" "fluidically isolated," and "fluidically joined," are intended to take into account the directionality of flow. One-way valves (e.g., one-way valves, check valves, and fluidic rectifiers or diodes) allow fluidic transport in only one direction such as from a flow channel into a reactor but not in the other direction (see, e.g., Adams et al., 2005, *J. Micromech. Microeng.* 15:1517-21; and references 6-12 therein). For example, a reactor connected to four flow channels, each of which is divided from the reactor by a one-way valve oriented to allow flow into but not out of the reactor, would be considered fluidically isolated. A reactor connected to four flow channels, three of which were oriented to allow flow in but not out of the reactor, one of which was a conventional two-way valve, would be considered fluidically isolated when the two-way valve was closed and would be considered fluidically joined when the two-way valve was open. In the case in which a first chip component (e.g., column) is connected via a flow channel to a second component (e.g., reactor) with an intervening one-way valve allowing flow only from the first to the second component, the first component is in fluidic communication with the second component, but the second component is not in fluidic communication with the first component.

As used herein, the "reactants" are molecules that are capable of chemically interacting with each other under suitable reaction conditions to produce a product.

As used herein, a "chemical reaction" is a process involving one, two or more substances (reactants) in solution, that chemically interact to yield one or more product(s) which are different from the reactants. Examples of chemical interactions include molecules or radicals combining to form larger molecules, molecules breaking apart to form two or more smaller molecules, and rearrangements of atoms within molecules. Most often, a chemical reaction involves the breaking and creation of covalent bonds. As used herein, a mere change of state (e.g., crystallization; isomerization, interconversion of polymorphs, or transition from liquid to gas) by itself is not a chemical reaction. In important embodiments, the reactant(s) and product(s) are in solution during the chemical reaction process. In certain embodiments, processes in which reactants are immobilized on a solid phase (e.g., conjugated to a bead) are specifically excluded from the definition of chemical reactions. In certain embodiments, reactions catalyzed by enzymes (e.g., proteins, ribozymes or the like) are specifically excluded from the definition of chemical reactions.

As used herein, two chemical reactions are "sequential" when a product of one reaction (i.e., the first reaction) is a reactant or catalyst in the other reaction (i.e., the second reaction).

As used herein, a "chemical process" means a chemical reaction, the process of solvent exchange, or the process of concentration.

As used herein, the term "solvent system" refers to a solvent (e.g., acetonitrile) or combination of solvents (e.g., 25% methanol/75% water) in which a solute is or can be dissolved.

As used herein, the term "reaction solvent system" refers to the solvent system present in a reactor at the time, following introduction of all reactants for a particular chemical reaction, that the reactor is fluidically isolated. Thus, the reaction solvent system is comprised of the solvent systems in which the reactants are introduced into a reactor plus any solvent(s) present in the reactor prior to introduction of the reactants, as modified by any solvent(s) withdrawn from the reactor after the first introduction of a reactant for the particular chemical reaction and prior to the time the reactor is fluidically isolated. Generally, the reaction solvent system is the solvent system in which a chemical reaction takes place in a reactor.

As used herein, reference to removal of a solvent system from a reactor "while retaining" a solute, reactant, product or other compound means that solvent is removed by evaporation from a fluidically isolated reactor. When a solvent system is removed from a reactor while retaining a solute compound in the reactor according to the invention, the rate of loss of solvent from the reactor exceeds the rate of loss of the solute compound. Thus the process of removing a solvent system from a fluidically isolated reactor while retaining the solute compound in the reactor results in an increase in the amount of the compound in the reactor per unit volume of the solvent in the reactor. In the absence of complete removal of solvent and/or precipitation of the compound, the concentration of the compound in the solution increases with the removal of the solvent system. In certain cases, the solvent is evaporated without removing the compound from the reactor (see below). In other cases some portion of the compound in the reactor enters or passes through the gas permeable portion of the reactor wall (e.g., the elastomer).

As used herein, reference to removal of a solvent system from a reactor "without removing" a solute, reactant, product or other compound means that at most an insignificant proportion of the solute, reactant, product or other compound is removed from the reactor. In this context an insignificant amount is less than 25%, more often less than 10%, very often less than 5% and sometimes less than 1% of the amount in the reactor prior to solvent removal. In some cases, no detectable amount of the compound is removed.

Figure 6A:
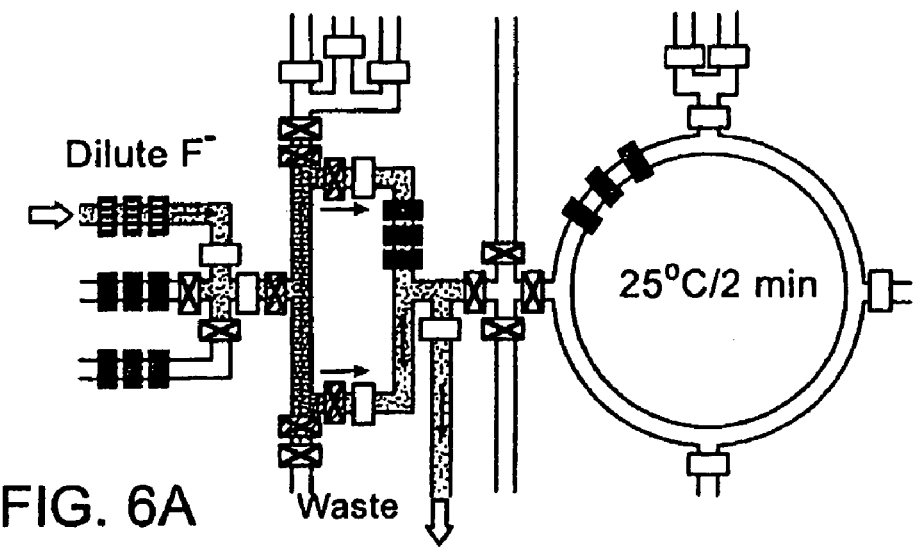
FIG. 6. Schematic diagrams summarize the fluoride concentration process which consisted of 9 steps in the CRC. (A) Diluted fluoride solution (indicated in blue) was introduced into the fluoride concentration loop from the top-left channel on the chip. The fluoride ion was trapped by anion exchange beads in the column. The filtrate solution was exported out of the device through the waste channel. The loading speed of fluoride solution was controlled by the metering pump (labeled in yellow). The loading process took around 2 min. (B) Following fluoride loading, 18 nL of $K_2CO_3$ solution (0.25 M) was pumped into fluoride concentration loop from the left-middle channel. This step takes 6 seconds at 25° C. (C) The $K_2CO_3$ solution was circulated in the fluoride concentration loop for 2 minutes to assure all the fluoride trapped on beads was released into the solution. By the end of this step, the fluoride concentration within the loop can increase by two orders of magnitude compared to the concentration of loaded fluoride solution. (D) After circulation, 20 nL of $K_2CO_3$ solution was introduced into the fluoride concentration loop to displace the concentrated fluoride solution into the reaction loop. This dead-end filling process (all the valves are closed except the valve controlling the loading channel, the air inside the loop is pushed out through the porous PDMS matrix) took 20 seconds. (E) With all the valves around reaction loop closed, the CRC was heated on a digitally controlled hotplate with a gradient (100° C. for 30 seconds, 120° C. for 30 seconds, 135° C. for 3 minutes). Most of the water from the concentrated fluoride solution was removed through direct evaporation. (F) The CRC was cooled down to 35° C. within 1 minute. (G) Anhydrous MeCN (in green) was introduced into the reaction loop through the bottom middle channel by dead-end filling. This step took less than 20 seconds at 25° C. (H) The CRC was heated again with a gradient (80° C./30 seconds, 100° C./1 minutes) to remove the remaining water inside the loop. With all valves around the loop closed, MeCN and water vapors were removed through direct evaporation. (I) The CRC was cooled down to 35° C. within 40 seconds.
Figure 6B:
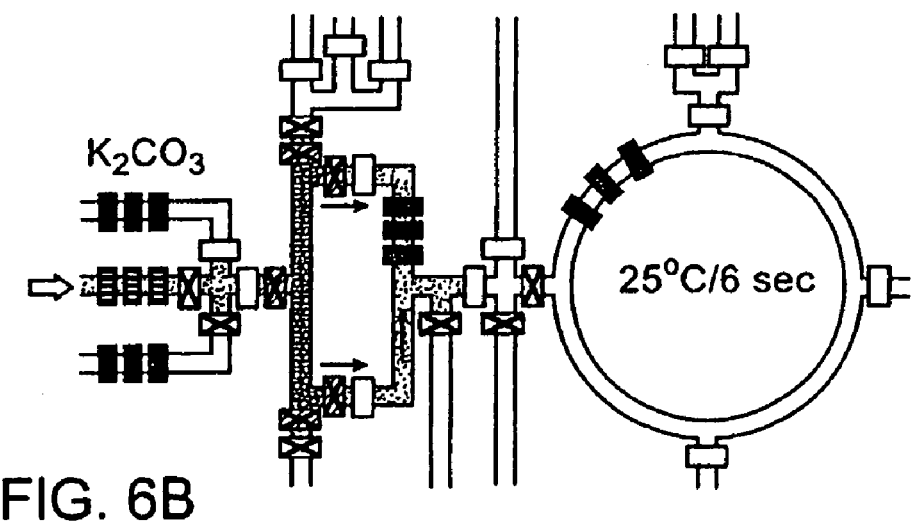
Figure 6C:
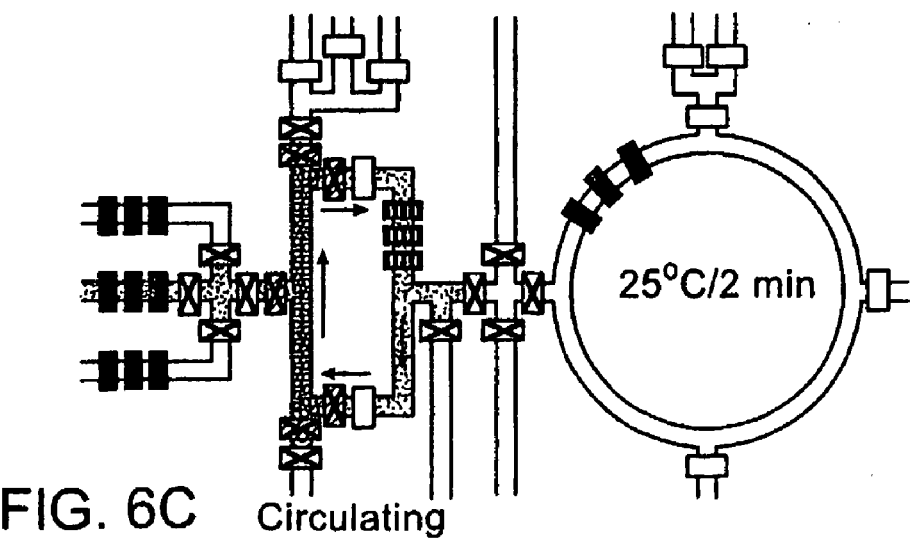
Figure 6D:
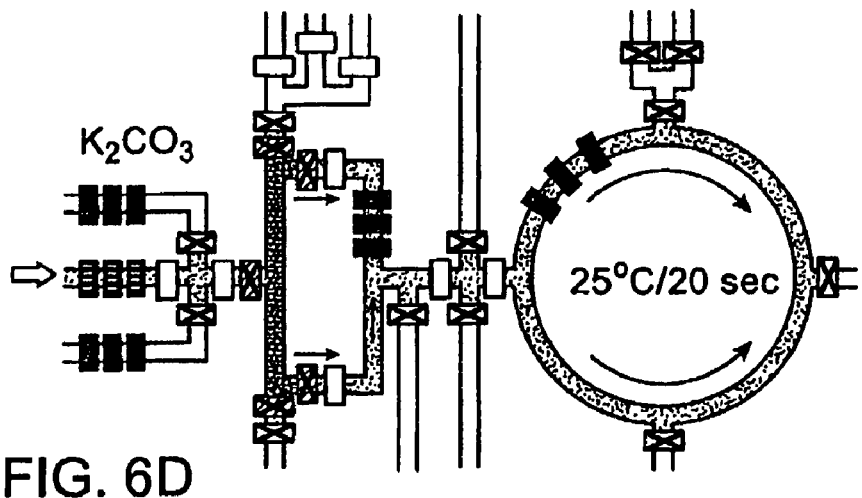
Figure 6E:
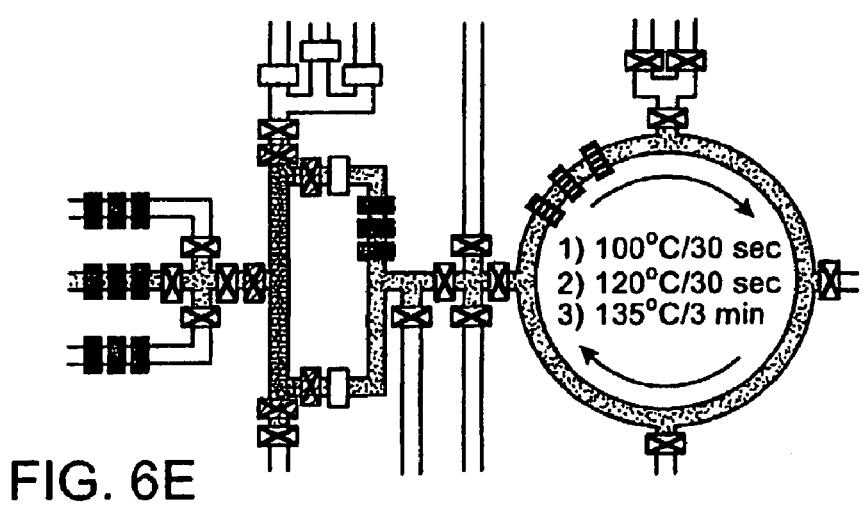
Figure 6F:
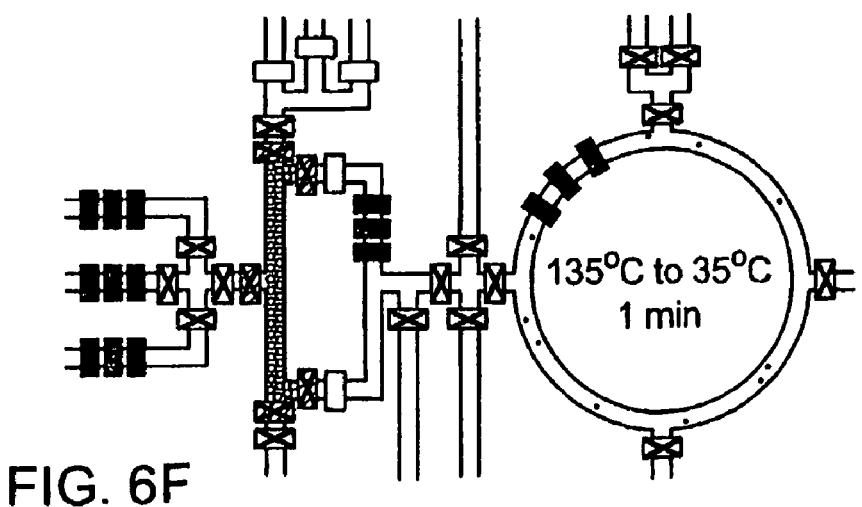
Figure 6G:
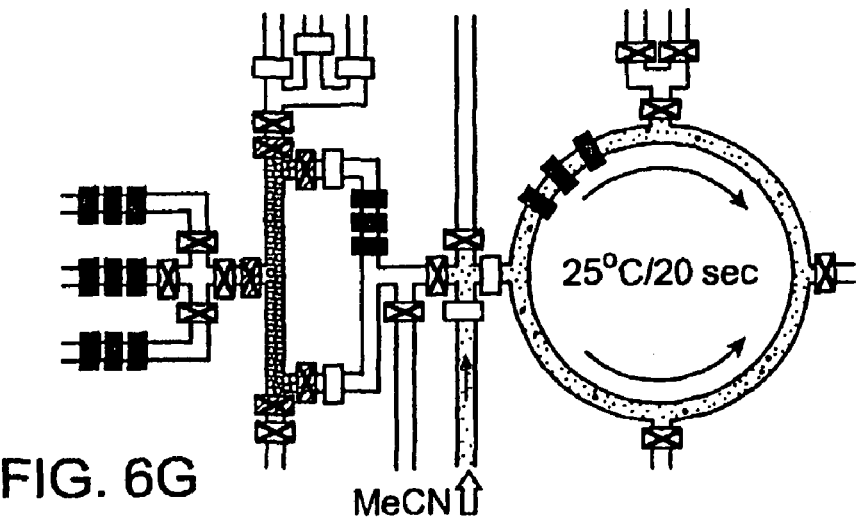
Figure 6H:
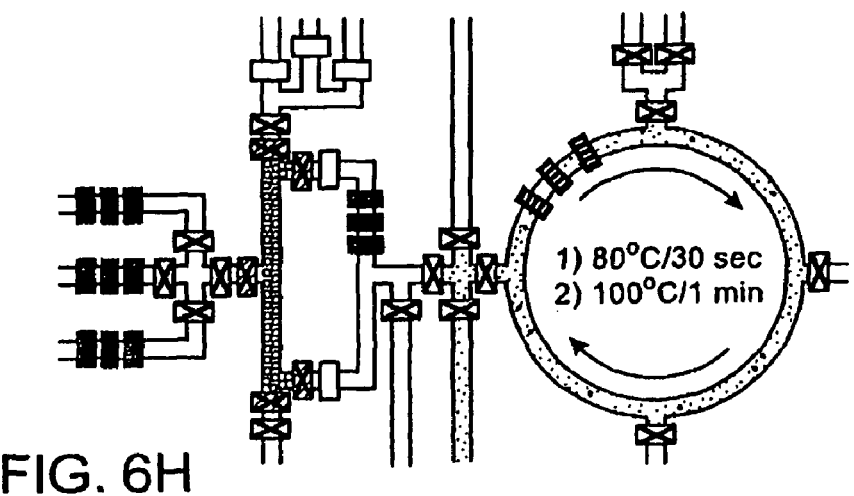
Figure 6I:
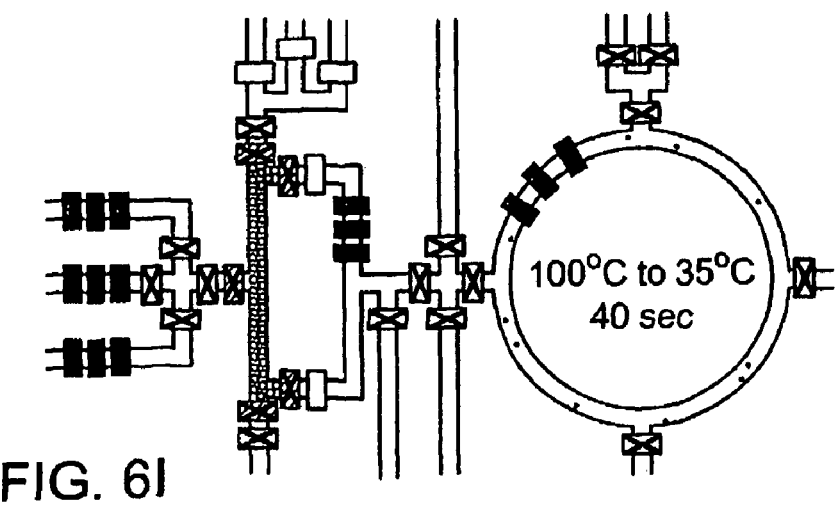
Figure 7A:
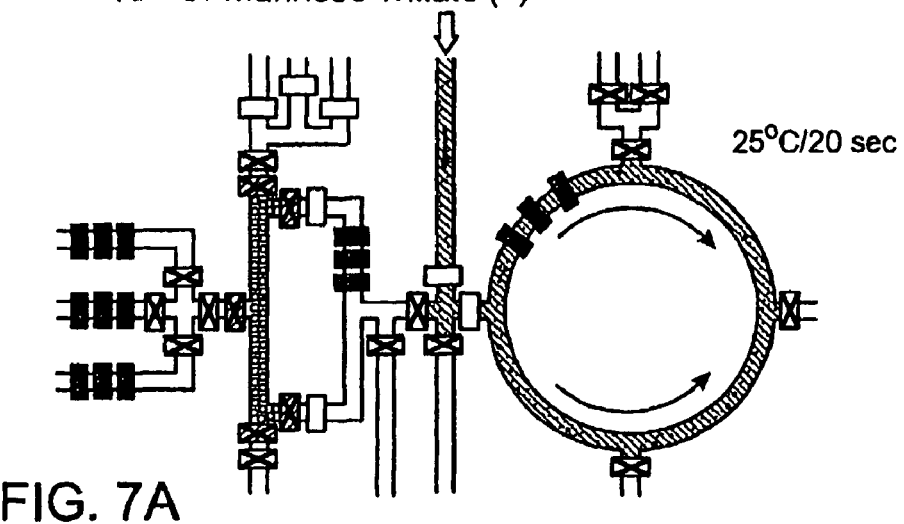
FIG. 7. Schematic diagrams summarize the fluorine substitution process which is composed of 3-step sequential operations in the CRC. (A) Kryptofix 222/the mannose triflate 1 in anhydrous MeCN were introduced from the top middle channel to the reaction loop by dead-end filling. This step took 20 seconds at 25° C. (B) The CRC was heated with a gradient (100° C./30 seconds, 120° C./50 seconds). At the same time, the solution was actively mixed by the circulating pump. The fluorinated intermediate 2a (or 2b) was obtained by the end of this step. (C) The CRC was cooled down to 35° C. within 40 seconds.
Figure 7B:
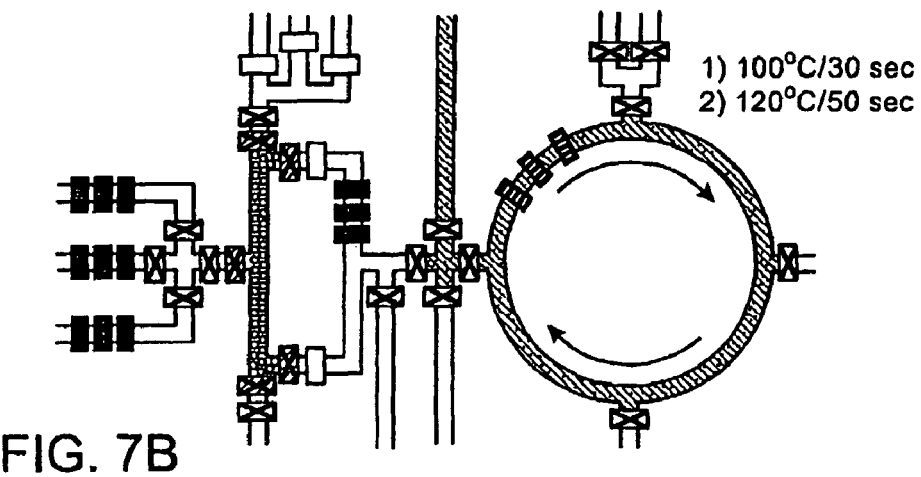
Figure 7C:
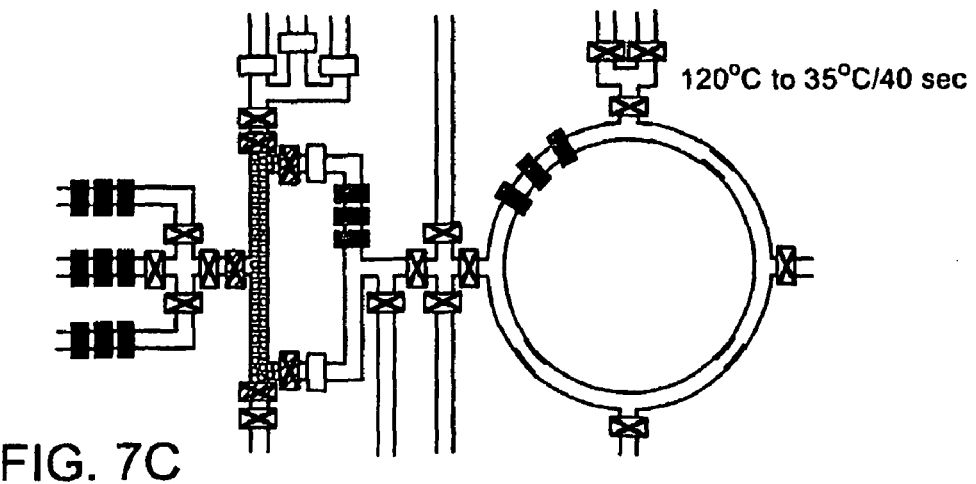

As used herein, a "closed path," or a "closed flow path" refers to a flow channel or a combination of flow channels (including channels in which a chromatography material is disposed) thorough which liquid can circulate. A closed path means that the channel or combination of channels can be temporarily isolated from other parts of the chip, for example by closing valves in any channels which lead into or out of the path, and that a liquid can then circulate through the path (when driven, for example, by a pump). A closed flow path may be circular (see, e.g., FIG. 1), rectilinear (see, e.g., FIGS. 6C and 14), curvilinear, and the like. Examples of closed paths include loop channels and concentration loops.

Section 2: Overview

The invention provides, in one aspect, an integrated microfluidic device, or chip, in which chemical reactions, and in particular, sequential chemical reactions, can be carried out. The chip has (1) at least one reactor that is fabricated at least in part from a gas-permeable material and that is configured to fluidically communicate with microfluidic flow channels, and (2) valves sufficient to fluidically isolate the reactor. Other microfluidic components also can be integrated into the chip, including, for example, control channels, guard channels, vent channels, fluid reservoirs, mixing reactors, rotary mixers, separation modules (e.g., separation columns), sorting regions, pumps, ports, vias, nozzles, monitoring systems, lenses, sensors, temperature control systems, heat sources, light sources, waveguides and the like. Examples of microfluidic chips include elastomeric chips, non-elastomeric chips, and partially elastomeric chips.

The invention also provides methods for carrying out chemical processes using a microfluidic chip and system. Using these methods, a wide variety of products can be synthesized rapidly, in high yields, and at low cost.

Although the invention is described in detail with reference to specific embodiments below, a brief overview of an exemplary chip and method will aid the reader in understanding the invention. It will be appreciated that this brief description is for illustration and is not intended to limit the invention in any way.

The chip architecture illustrated in FIG. 1 represents a design that is capable of supporting several sequential chemical processes, including ion exchange, product purification, solvent evaporation, aqueous chemical reactions, anhydrous chemical reactions, and chemical reactions under elevated temperature or pressure conditions. Channel 111 can serve as a chromatographic column for the purpose of supporting the chemical processes of ion exchange, or reactant or product purification, or the like. To do this, channel 111 is loaded with an appropriate chromatographic resin material designed for ion exchange or product or reactant purification, as illustrated. Valve 110E is configured to retain a chromatographic resin but allow fluid to flow through the valve. A reaction mixture may be flowed through the column by opening valve 110A and introducing the reaction mixture through channel 113, with valves 110B and 110D closed.

It may be desirable to route a reaction mixture through a column multiple times. In that case, the reaction mixture is introduced through channel 113 via open valve 110A. Valve 110E and 110C are closed. The air permeability of the channel material is then utilized to completely fill channel 111 (column 111) and channel 112 with a reaction mixture (e.g., comprising a reactant in solution). Peristaltic pump 103B is used to cycle the reaction mixture around the loop described by the closed and open valves, thereby pushing the reactant mixture through the column 111 multiple times.

(The same column may be alternatively used by flowing a reaction mixture through the column, and then using the flow-through fraction (or, alternatively an eluate) in other regions of the chemical reaction circuit for subsequent chemical processing. For example, a reaction mixture can be introduced via column 113 through open valve 110A, with valves 110B and 110D closed, and eluting the product through valve 110E for further use.)

The reaction mixture prepared or purified on the column 111 may then be subjected to further chemical processes. By opening valves 110A, 110D, 110C, 105A, and 102A the reaction mixture may be flushed off of the column, through channel 100, and introduced into the reaction chamber 104 (reactor 104). (Alternatively, a reaction mixture may be introduced into reactor 104 from another source via channel 100.) Additional chemical reactants may be introduced from channel 109 by opening valve 105B (optionally with valve 110C closed). Other reactants may be introduced from, for example, channel 107 by opening valve 102B. The reaction mixture within the reaction chamber 104 may be mixed using peristaltic pump 103C for a desired amount of time. The entire reaction mixture may be heated during the chemical reaction process by heating the chip or a section thereof.

Solvent may be removed from reaction chamber 104 by evaporating the solvent through the matrix material from which the microfluidic chemical reaction circuit, reactor, or portion thereof is comprised. Additional solvents and/or reagents may then be introduced into the reactor through, for example, channel 107.

It will be apparent that reaction chambers of various shapes and sizes, additional columns, etc., may be introduced into the chemical reaction circuit design as necessary to accomplish specific chemical processes.

Figure 2A:
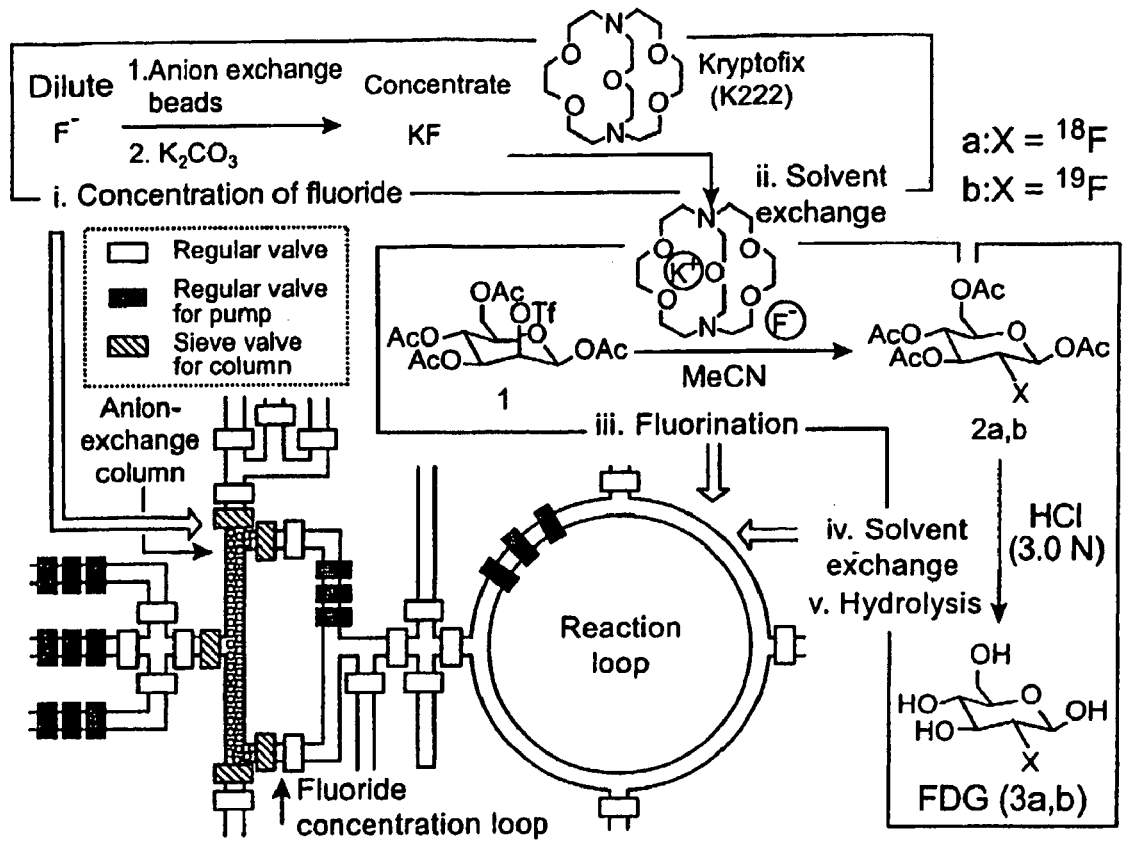
FIG. 2. (A) Schematic representation of a chemical reaction circuit (CRC) used in the production of 2-deoxy-2-fluoro-D-glucose (FDG) (3a,b). Five sequential processes—(i) concentration of dilute fluoride ion using a miniaturized anion-exchange column located in a square-shaped fluoride concentration loop, (ii) solvent exchange from water to dry MeCN, (iii) fluorination of the D-mannose triflate precursor 1, (iv) solvent exchange back to water; and (v) acidic hydrolysis of the fluorinated intermediate 2a (or 2b) in a ring-shaped reaction loop—produce nanogram (ng) levels of FDG (3a,b). The operation of the CRC is controlled by pressure-driven valves, with their delegate responsibilities illustrated by their colors: red for regular valves (for isolation), yellow for pump valves (for fluidic metering circulation), and blue for sieve valves (for trapping anion exchange beads in the column module). (B) Optical micrograph of the central area of the CRC. The various channels have been loaded with food dyes to help visualize the different components of the microfluidic chip: (red) control channels for regular valves, (blue) control channels for sieve valves, (yellow) control channels for pump valves, and (green) fluidic channels. Inset: Actual view of the device; a penny (18.9 mm in diameter) calibrates the dimensions on the device.
Figure 2B:
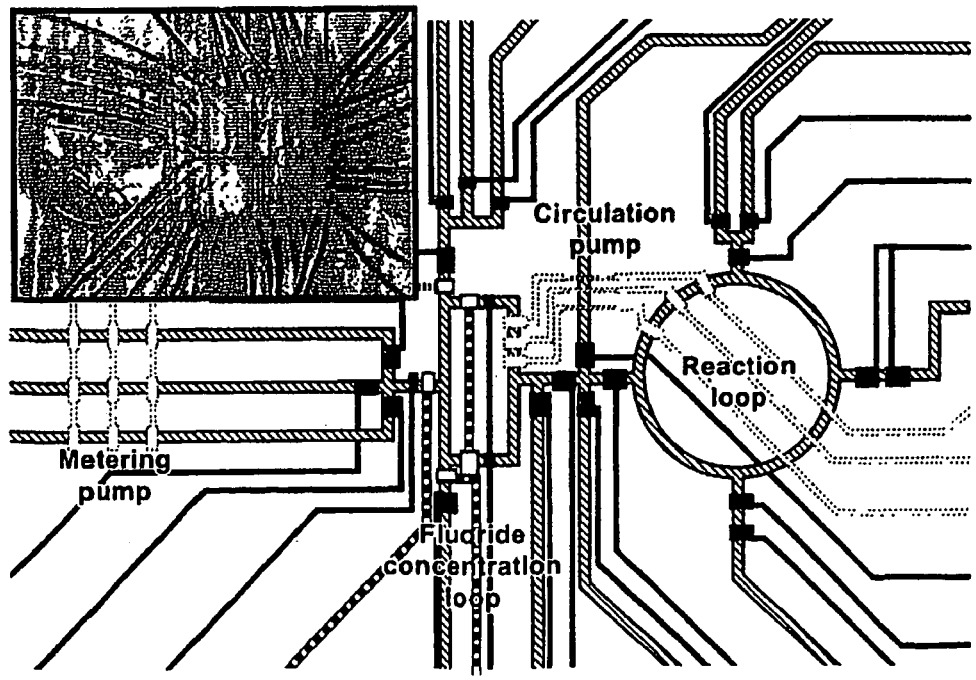

A specific embodiment of a chemical reaction circuit, designed for the preparation of the radiolabeled molecular imaging agent, [$^{18}$F]fluordeoxyglucose([$^{18}$F]FDG) is presented in FIG. 2. This particular application of chemical reaction circuits illustrates many important aspects of the Chemical Reaction Circuit (CRC), since the preparation of [$^{18}$F]FDG involves the use of a column, multiple solvents, sequential chemical steps, chemical processes at elevated temperatures and pressures, and product elution. In particular, the synthesis of [$^{18}$F]FDG proceeds according to a synthetic scheme that includes the following sequential chemical reactions:

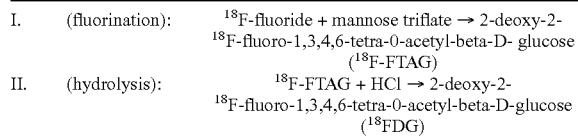

| I. | (fluorination): | $^{18}$F-fluoride + mannose triflate → 2-deoxy-2-$^{18}$F-fluoro-1,3,4,6-tetra-0-acetyl-beta-D- glucose ($^{18}$F-FTAG) |
|---|---|---|
| II. | (hydrolysis): | $^{18}$F-FTAG + HCl → 2-deoxy-2-$^{18}$F-fluoro-1,3,4,6-tetra-0-acetyl-beta-D-glucose ($^{18}$FDG) |

The device shown in FIG. 1 is simplified, but illustrates important features of the invention. See FIGS. 3-4, 6-8 and 11-12, 14 and 17-18 for more detailed schematics.

The chip illustrated in FIG. 2 is designed to carry out five sequential chemical processes—[$^{18}$F]fluoride concentration, water evaporation, radiofluorination, solvent exchange, and hydrolytic deprotection. Referring to FIG. 2, an aqueous potassium fluoride solution is transported by pump 103A from a source through flow channel 100, through open valve 102A, and into reactor loop 104, which has at least one gas permeable portion. The source can be, for example, a fluoride concentration loop. The solution transported into reactor 104 is retained in the reactor because valves 102B-C are closed. After filling or partially filling the reactor, valve 102A is closed thereby fluidically isolating the reactor. Reactor 104 is heated using a heater to evaporate solvent (water) from the reactor. Solvent (Water) vapor escapes reactor 104 though gas permeable material from which the chemical reaction circuit is fabricated, at least in part. When sufficient solvent is evaporated, valve 102B is opened, an acetonitrile solution of Kryptofix 222 and d-mannose triflate is transported from a source through flow channel 106 into the reactor 104, and valve 102B is closed to fluidically isolate the reactor. The $^{18}$F-fluoride and d-mannose triflate react to produce $^{18}$F-FTAG while the reactants are being introduced into reactor 104 and/or after valve 102B is closed. Reactor 104 is again heated using the heater to evaporate solvent (acetonitrile) from the reactor though the gas permeable material from which the chemical reaction circuit is, at least in part, composed. After evaporating sufficient acetonitrile, valve 102D is opened and an aqueous HCl solution is transported from a source through flow channel 108 and through valve 102D into reactor 104. Valve 102D is then closed to fluidically isolate the reactor 104. The introduction of HCl results in hydrolysis of $^{18}$F-FTAG to produce [$^{18}$F]FDG, while the reactants are being introduced into reactor 104 is being filled and/or after valve 102D is closed. Valves 102C and 102E are then opened and water is introduced into the reactor 104 via flow channel 107, forcing the solution containing the reaction product through open valve 102E and flow channel 109 to a reservoir or other component of the system. Distribution manifolds (described below) also can be used for introducing solutions into the reactor.

The synthesis of [$^{18}$F]FDG using a device of the type in FIG. 2 and in the Examples, illustrates a multistep chemical synthesis involving removing and exchanging solvents specific to individual synthetic steps and isolating distinct regions on the chip for individual chemical processes.

Section 3: Microfluidic Device and System

This section describes exemplary materials and components of CRC chips.

A. Materials and Fabrication of Device

Devices of the invention can be constructed out of any material or combination of materials from which a reactor and an associated network of channels and valves can be formed. Materials from which a chip can be fabricated include, without limitation, elastomers, silicon, glass, metal, polymer, ceramic, inorganic materials, and/or combinations of these materials.

The methods used in fabrication of a CRC device will vary with the materials used, and include soft lithography methods, microassembly, bulk micromachining methods, surface micro-machining methods, standard lithographic methods, wet etching, reactive ion etching, plasma etching, stereolithography and laser chemical three-dimensional writing methods, modular assembly methods, replica molding methods, injection molding methods, hot molding methods, laser ablation methods, combinations of methods, and other methods known in the art or developed in the future. A variety of exemplary fabrication methods are described in Fiorini and Chiu, 2005, "Disposable microfluidic devices: fabrication, function, and application" *Biotechniques* 38:429-46; Beebe et al., 2000, "Microfluidic tectonics: a comprehensive construction platform for microfluidic systems." *Proc. Natl. Acad. Sci. USA* 97:13488-13493; Rossier et al., 2002, "Plasma etched polymer microelectrochemical systems" *Lab Chip* 2:145-150; Becker et al., 2002, "Polymer microfluidic devices" *Talanta* 56:267-287; Becker et al., 2000, "Polymer microfabrication methods for microfluidic analytical applications" *Electrophoresis* 21:12-26; U.S. Pat. No. 6,767,706 B2, e.g., Section 6.8 "Microfabrication of a Silicon Device"; Terry et al., 1979, A Gas Chromatography Air Analyzer Fabricated on a Silicon Wafer, *IEEE Trans. on Electron Devices*, v. ED-26, pp. 1880-1886; Berg et al., 1994, *Micro Total Analysis Systems*, New York, Kluwer; Webster et al., 1996, Monolithic Capillary Gel Electrophoresis Stage with On-Chip Detector in International Conference On Micro Electromechanical Systems, MEMS 96, pp. 491496; and Mastrangelo et al., 1989, *Vacuum-Sealed Silicon Micromachined Incandescent Light Source*, in Intl. Electron Devices Meeting, *IDEM* 89, pp. 503-506.

In preferred embodiments, the device is fabricated using elastomeric materials. Fabrication methods using elastomeric materials will only be briefly described here, because elastomeric materials, methods of fabrication of devices made using such materials, and methods for design of devices and their components have been described in detail (see, e.g., Unger et al., 2000, *Science* 288:113-16; U.S. Pat. Nos. 6,960,437 (Nucleic acid amplification utilizing microfluidic devices); 6,899,137 (Microfabricated elastomeric valve and pump systems); 6,767,706 (Integrated active flux microfluidic devices and methods); 6,752,922 (Microfluidic chromatography); 6,408,878 (Microfabricated elastomeric valve and pump systems); 6,645,432 (Microfluidic systems including three-dimensionally arrayed channel networks); U.S. Patent Application publication Nos. 2004/0115838, 20050072946; 20050000900; 20020127736; 20020109114; 20040115838; 20030138829; 20020164816; 20020127736; and 20020109114; PCT patent publications WO 2005/084191; WO05030822A2; and WO 01/01025; Quake & Scherer, 2000, "From micro to nanofabrication with soft materials" Science 290: 1536-40; Xia et al., 1998, "Soft lithography" Angewandte Chemie-International Edition 37:551-575; Unger et al., 2000, "Monolithic microfabricated valves and pumps by multilayer soft lithography" *Science* 288:113-116; Thorsen et al., 2002, "Microfluidic large-scale integration" *Science* 298:580-584; Chou et al., 2000, "Microfabricated Rotary Pump" Biomedical Microdevices 3:323-330; Liu et al., 2003, "Solving the "world-to-chip" interface problem with a microfluidic matrix" *Analytical Chemistry* 75, 4718-23," Hong et al, 2004, "A nanoliter-scale nucleic acid processor with parallel architecture" *Nature Biotechnology* 22:435-39; Fiorini and Chiu, 2005, "Disposable microfluidic devices: fabrication, function, and application" *Biotechniques* 38:429-46; Beebe et al., 2000, "Microfluidic tectonics: a comprehensive construction platform for microfluidic systems." *Proc. Natl. Acad. Sci. USA* 97:13488-13493; Rolland et al., 2004, "Solvent-resistant photocurable "liquid Teflon" for microfluidic device fabrication" *J. Amer. Chem. Soc.* 126:2322-2323; Rossier et al., 2002, "Plasma etched polymer microelectrochemical systems" *Lab Chip* 2:145-150; Becker et al., 2002, "Polymer microfluidic devices" Talanta 56:267-287; Becker et al., 2000, "Polymer microfabrication methods for microfluidic analytical applications" *Electrophoresis* 21:12-26; Terry et al., 1979, A Gas Chromatography Air Analyzer Fabricated on a Silicon Wafer, IEEE Trans. on Electron Devices, v. ED-26, pp. 1880-1886; Berg et al., 1994, Micro Total Analysis Systems, New York, Kluwer; Webster et al., 1996, Monolithic Capillary Gel Electrophoresis Stage with On-Chip Detector in International Conference On Micro Electromechanical Systems, MEMS 96, pp. 491496; and Mastrangelo et al., 1989, Vacuum-Sealed Silicon Micromachined Incandescent Light Source, in Intl. Electron Devices Meeting, IDEM 89, pp. 503-506; and other references cited herein and found in the scientific and patent literature.

Elastomeric Materials

Elastomers in general are polymers existing at a temperature between their glass transition temperature and liquefaction temperature. See Allcock et al., *Contemporary Polymer Chemistry*, 2nd Ed. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Elastomeric materials having a Young's modulus of between about 1 Pa-1 TPa, more preferably between about 10 Pa-100 GPa, more preferably between about 20 Pa-1 GPa, more preferably between about 50 Pa-10 MPa, and more preferably between about 100 Pa-1 MPa are useful in accordance with the present invention, although elastomeric materials having a Young's modulus outside of these ranges could also be utilized depending upon the needs of a particular application.

Given the tremendous diversity of polymer chemistries, precursors, synthetic methods, reaction conditions, and potential additives, there are a huge number of possible elastomer systems that could be used to make the devices of the invention. Common elastomeric polymers include perfluoropolyethers, polyisoprene, polybutadiene, polychloroprene, polyisobutylene, poly(styrene-butadiene-styrene), polyurethanes, and silicones, for example, or poly(bis(fluoroalkoxy) phosphazene) (PNF, Eypel-F), poly(carborane-siloxanes) (Dexsil), poly(acrylonitrile-butadiene) (nitrile rubber), poly (1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon), polydimethylsiloxane, polydimethylsiloxane copolymer, and aliphatic urethane diacrylate. For illustration, a brief description of the most common classes of elastomers is presented here:

Silicones: Silicone polymers have great structural variety, and a large number of commercially available formulations. In an exemplary aspect of the present invention, the present systems are fabricated from an elastomeric polymer such as GE RTV 615 (formulation), a vinyl-silane crosslinked (type) silicone elastomer (family). The vinyl-to-(Si—H) crosslinking of RTV 615 allows both heterogeneous multilayer soft lithography and photoresist encapsulation. However, this is only one of several crosslinking methods used in silicone polymer chemistry and suitable for use in the present invention. In one embodiment, the silicone polymer is polydimethylsiloxane (PDMS).

Perfluoropolyethers: Functionalized photocurable perfluoropolyether (PFPE) is particularly useful as a material for fabricating solvent-resistant microfluidic devices for use with certain organic solvents. These PFPEs have material properties and fabrication capabilities similar to PDMS but with compatibility with a broader range of solvents. See, e.g., PCT Patent Publications WO 2005030822 and WO 2005084191 and Rolland et al., 2004, "Solvent-resistant photocurable "liquid Teflon" for microfluidic device fabrication" *J. Amer. Chem. Soc.* 126:2322-2323.

Polyisoprene, polybutadiene, polychloroprene: Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). Homogeneous multilayer soft lithography would involve incomplete vulcanization of the layers to be bonded and photoresist encapsulation would be possible by a similar mechanism.

Polyisobutylene: Pure Polyisobutylene has no double bonds, but is crosslinked to use as an elastomer by including a small amount (~1%) of isoprene in the polymerization. The isoprene monomers give pendant double bonds on the polyisobutylene backbone, which may then be vulcanized as above.

Poly(styrene-butadiene-styrene): Poly(styrene-butadiene-styrene) is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes: Polyurethanes are produced from di-isocyanates (A-A) and di-alcohols or di-amines (B-B); since there are a large variety of di-isocyanates and di-alcohols/amines, the number of different types of polyurethanes is huge. The A vs. B nature of the polymers, however, would make them useful for heterogeneous multilayer soft lithography just as RTV 615 is: by using excess A-A in one layer and excess B-B in the other layer.

The selection of materials (whether elastomeric or non-elastomeric) will take into account the need for particular material properties and will depend on a variety of factors including: ease of manufacture, the nature of the chemical synthesis, solvent resistance and temperature stability. For example, fluidic circuits fabricated from PDMS will not be compatible with all organic solvents (see, e.g., Lee et al., 2003, *Anal. Chem.* 75:6544-54). This issue can be addressed by the use of chemically resistant elastomers in place of PDMS in at least some regions of the device. For example, perfluoropolyether (PFPE) can be used (see Rolland et al., 2004, "Solvent-resistant photocurable "liquid Teflon" for microfluidic device fabrication" *J. Amer. Chem. Soc.* 126: 2322-23, and citations herein above). Alternatively, the elastomer (e.g., PDMS) surface can be chemically modified to increase compatibility with organic solvents and improve function Methods and reagents for such modification include those described in US 2004/0115838 [para. 0293] et seq.; copolymers of tetrafluoroethylene, perfluoromethylvinylether (also called TFE-perfluorovinylether polymers) such as Chemraz (Greene-Tweed, 10% solution) diluted 1:1 in low boiling point perfluorocarbon liquid, e.g. Flourinert from 3M), Kalrez (Du Pont), Chemtex (Utex Industries), and fluorocarbon polymers (FKM, e.g. poly(tetrafluoro-co-hexafluoropropylene) such as Cytop coating (poly(perfluoro (alkenyl vinyl ether) from Bellex International Corp. and Novec EGC-1700 coating (fluoroaliphatic polymer) from 3M which can be applied by flushing the solutions though channels (e.g., 3×40 microliters at 25 psi, at 1 min intervals). In addition, many chemical reactions can be carried out in a variety of solvents. Reaction series to be carried out in a chip made using particular materials can be designed to use solvents that are compatible with the materials over the period of time necessary to complete the reaction.

For devices made using multilayer soft lithography (in which layers of elastomer are cured separately and then bonded together) another important consideration for fabrication is the ability to bond multiple layers of elastomers together. This scheme requires that cured layers possess sufficient reactivity to bond together. Either the layers may be of the same type, and are capable of bonding to themselves, or they may be of two different types, and are capable of bonding to each other. Other possibilities include the use an adhesive between layers, the use of thermoset elastomers, and use of composite structures.

Elastomeric Fabrication Methods

Methods of fabrication of complex microfluidic circuits using elastomeric are known and are described in Unger et al., 2000, *Science* 288:113-116; Quake & Scherer, 2000, "From micro to nanofabrication with soft materials" *Science* 290: 1536-40; Xia et al., 1998, "Soft lithography" *Angewandte Chemie-International Edition* 37:551-575; Unger et al., 2000, "Monolithic microfabricated valves and pumps by multilayer soft lithography" *Science* 288:113-116; Thorsen et al., 2002, "Microfluidic large-scale integration" *Science* 298: 580-584; Chou et al., 2000, "Microfabricated Rotary Pump" *Biomedical Microdevices* 3:323-330; Liu et al., 2003, "Solving the "world-to-chip" interface problem with a microfluidic matrix" *Analytical Chemistry* 75, 4718-23," and other references cited herein and known in the art.

Microfluidic devices are generally constructed utilizing single and multilayer soft lithography (MSL) techniques and/or sacrificial-layer encapsulation methods. The basic MSL approach involves casting a series of elastomeric layers on a micro-machined mold, removing the layers from the mold and then fusing the layers together. In the sacrificial-layer encapsulation approach, patterns of photoresist are deposited wherever a channel is desired. One exemplary method for fabricating elastomeric devices is briefly described below.

In brief, one method for fabricating elastomeric devices involve fabricating mother molds for top layers (the elastomeric layer with the control channels and reactors, the elastomeric layer with the flow channels) on silicon wafers by photolithography with photoresist (Shipley SJR 5740). Channel heights can be controlled precisely by the spin coating rate. Photoresist channels are formed by exposing the photoresist to UV light followed by development. Heat reflow process and protection treatment is typically achieved as described by Unger et al. supra. A mixed two-part-silicone elastomer (GE RTV 615) is then spun into the bottom mold and poured onto the top mold, respectively. Spin coating can be utilized to control the thickness of bottom polymeric fluid layer. The partially cured top layer is peeled off from its mold after baking in the oven at 80° C. for 25 minutes, aligned and assembled with the bottom layer. A 1.5-hour final bake at 80° C. is used to bind these two layers irreversibly. Once peeled off from the bottom silicon mother mold, this RTV device is typically treated with HCL (0.1N, 30 min at 80° C.). This treatment acts to cleave some of the Si—O—Si bonds, thereby exposing hydroxy groups that make the channels more hydrophilic.

The device can then optionally be hermetically sealed to a support. The support can be manufactured of essentially any material, although the surface should be flat to ensure a good seal, as the seal formed is primarily due to adhesive forces. Examples of suitable supports include glass, plastics and the like.

The devices formed according to the foregoing method result in the substrate (e.g., glass slide) forming one wall of the flow channel. Alternatively, the device once removed from the mother mold is sealed to a thin elastomeric membrane such that the flow channel is totally enclosed in elastomeric material. The resulting elastomeric device can then optionally be joined to a substrate support.

Access to the fluidic channels is achieved by punching holes through the bulk material, and the devices are readily bonded to glass or silicon substrates. Large arrays of active components, such as channels, reactors, valves and pumps, can be created by stacking multiple, individually fabricated layers.

Composite Structures

Diverse materials can be used in fabrication of the chip and reactor. Devices, and in particular, reactors, can be fabricated from combinations of materials. For example, in some embodiments the walls and ceiling of a reactor are elastomeric and the floor of the reactor is formed from an underlying nonelastomeric substrate (e.g., glass), while in other embodiments, both the walls and floors of the reactor are constructed from a nonelastomeric material, and only the ceiling of the reactor is constructed from elastomer. These chips and reactors are sometimes referred to as "composite structures." See, e.g., US 20020127736. A variety of approaches can be employed to seal the elastomeric and nonelastomeric components of a device, some of which are described in U.S. Pat. No. 6,719,868 and US 20020127736, ¶¶0227 et seq.

B. Basic Device Components: Flow Channels, Reactors, Valves

Flow Channels

The term "flow channel" refers to a microfluidic channel through which a solution can flow. The dimensions of flow channels can vary widely but typically include at least one cross-sectional dimension (e.g., height, width, or diameter) less than 1 mm, preferably less than 0.5 mm, and often less than 0.3 mm. Flow channels often have at least one cross-sectional dimension in the range of 0.05 to 1000 microns, more preferably 0.2 to 500 microns, and more preferably 10 to 250 microns. The channel may have any suitable cross-sectional shape that allows for fluid transport, for example, a square channel, a circular channel, a rounded channel, a rectangular channel, etc. In an exemplary aspect, flow channels are rectangular and have widths of about in the range of 0.05 to 1000 microns, more preferably 0.2 to 500 microns, and more preferably 10 to 250 microns. In an exemplary aspect, flow channels have depths of 0.01 to 1000 microns, more preferably 0.05 to 500 microns, more preferably 0.2 to 250 microns, and more preferably 1 to 100 microns. In an exemplary aspect, flow channels have width-to-depth ratios of about 0.1:1 to 100:1, more preferably 1:1 to 50:1, more preferably 2:1 to 20:1, and most preferably 3:1 to 15:1, and often about 10:1. As shown in FIG. 3, flow channels in elastomeric devices may have a curved or elliptical face that allows the deflected elastomeric membrane is fully compliant to the round-profile fluidic channel and allowing complete closure of monolithic valves (except at the positions of sieve valves, as discussed below). In one embodiment the flow channel dimensions are 250-300 microns by 45 microns. Although certain preferred embodiments have been described, the flow channels of the invention are not limited to the dimensions above.

Figure 11B:
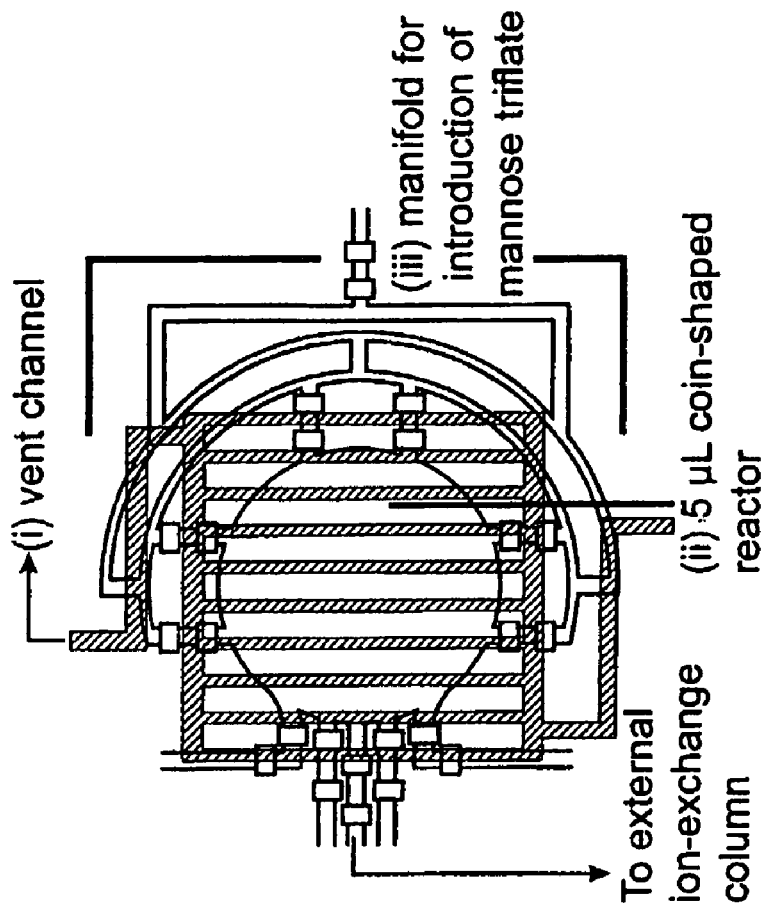
FIG. 11. (A) A photograph of second generation CRC in use for [$^{18}$F]FDG production. (B) Schematic representation of the second generation CRC composed of three major functional components, including (i) vent channel, (ii) coin-shaped reactor and (iii) manifold for introduction of the mannose triflate solution.
Figure 11A:
Figure 12A:
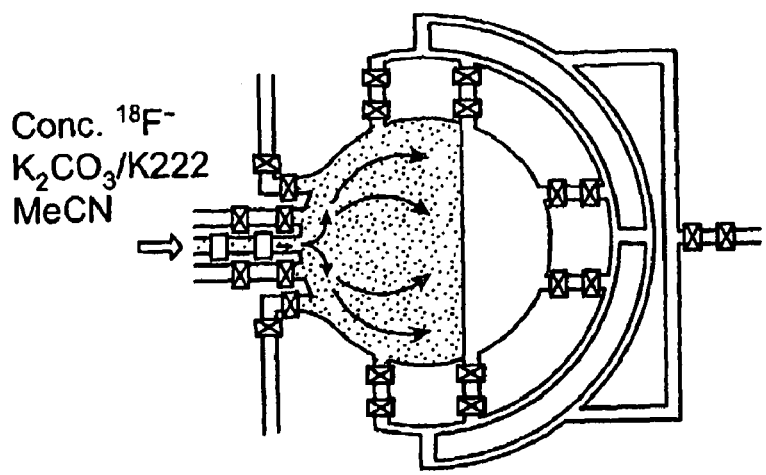
FIG. 12 shows schematic diagrams summarizing the [$^{18}$F] FDG (3a) synthesis on the second generation CRC. (A) Concentrated mixture of $^{18}$F$^-$/Kryptofix222/K$_2$CO$_3$ in MeCN is introduced into the reaction chamber until the reaction chamber is ⅔ full. This process is accelerated by applying vacuum to the vent above the reaction chamber to remove the gas being displaced by the fluoride solution. (B) The mannose triflate 2a solution in MeCN (25 mg/mL) is loaded to fill the distribution manifold by dead-end filling. The manifold is designed to introduce mannose triflate 2a solution into the reaction chamber equally and simultaneously through the six ports. (C) The mannose triflate 2a solution is introduced into the reaction chamber by employing 10 psi of loading pressure. (D) The reaction mixture was kept at 25° C. for 5 min, and the fluorination reaction is carried out at 65° C. for 2 min. The vacuum in the vent is then turned on to evaporate ¼ of MeCN in the reaction chamber. (E) 3N HCl solution is loaded into the reaction chamber, and the acidic hydrolysis is performed at 60° C. (F) The remaining MeCN is evaporated at 75° C. for 5 min. (G) The reaction chamber is cooled to 40° C. and vacuum in the vent is turned off prior to elution. (H) As the valves are opened on the water inlet and the product outlet, [$^{18}$F]FDG (3a) is flushed out of the chamber. The tangential inlet and outlet allow the water trajectory to follow along the far wall of the reaction chamber ensuring complete product elution.
Figure 12B:
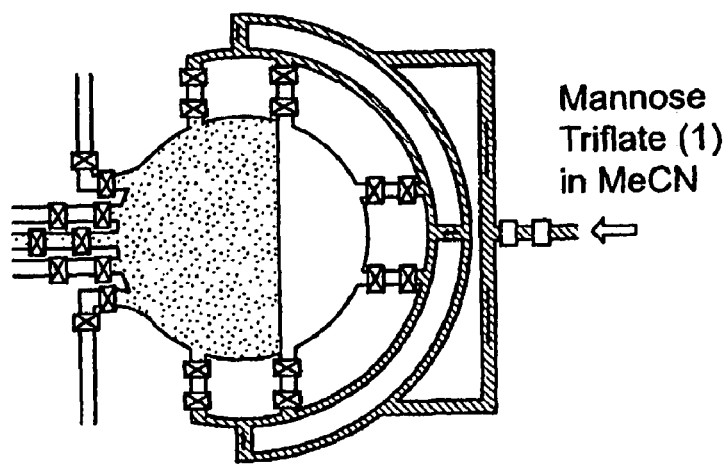
Figure 12C:
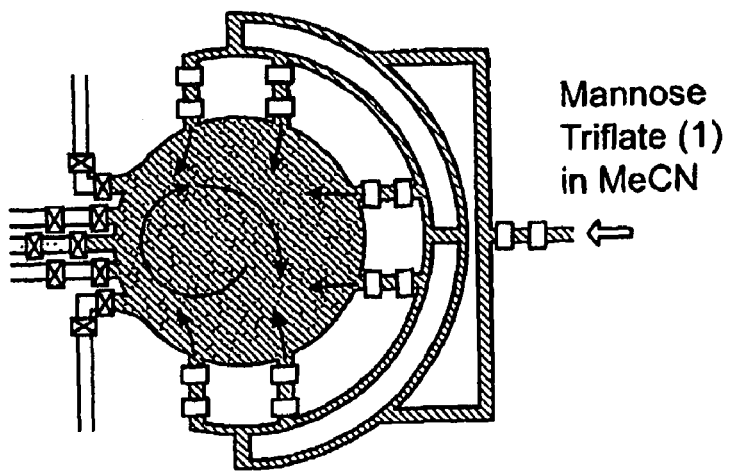
Figure 12D:
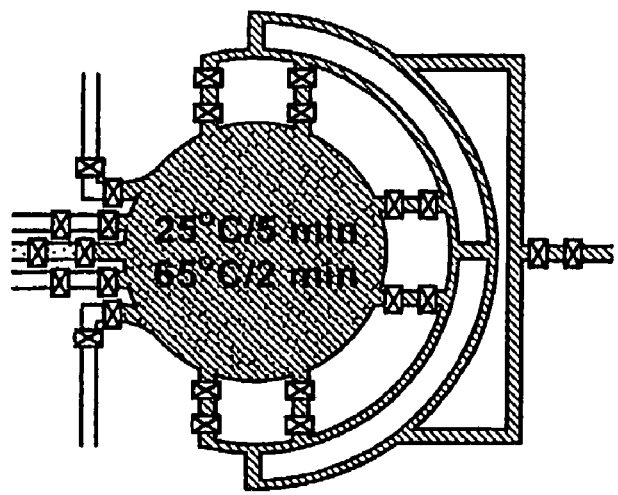
Figure 12E:
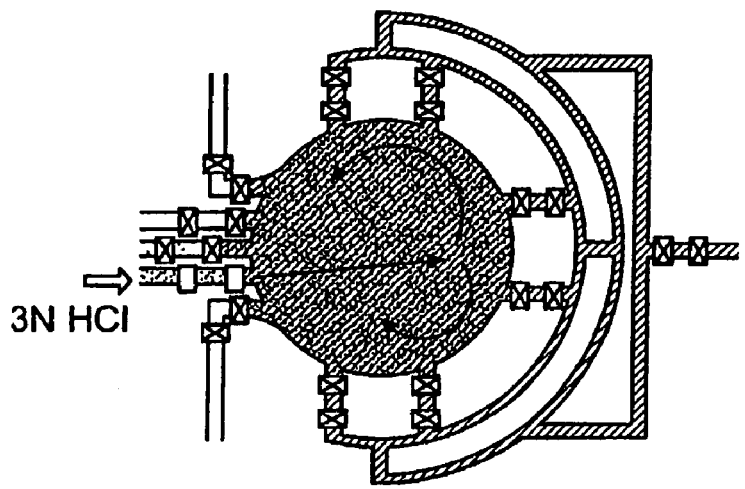
Figure 12F:
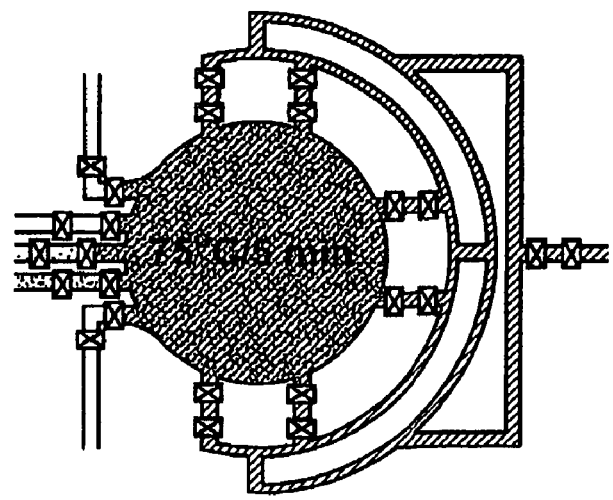
Figure 12G:
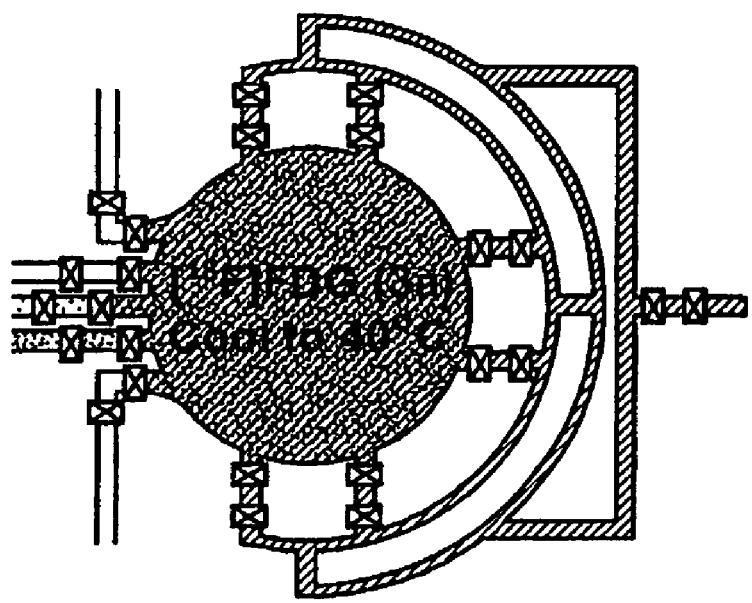
Figure 12H:
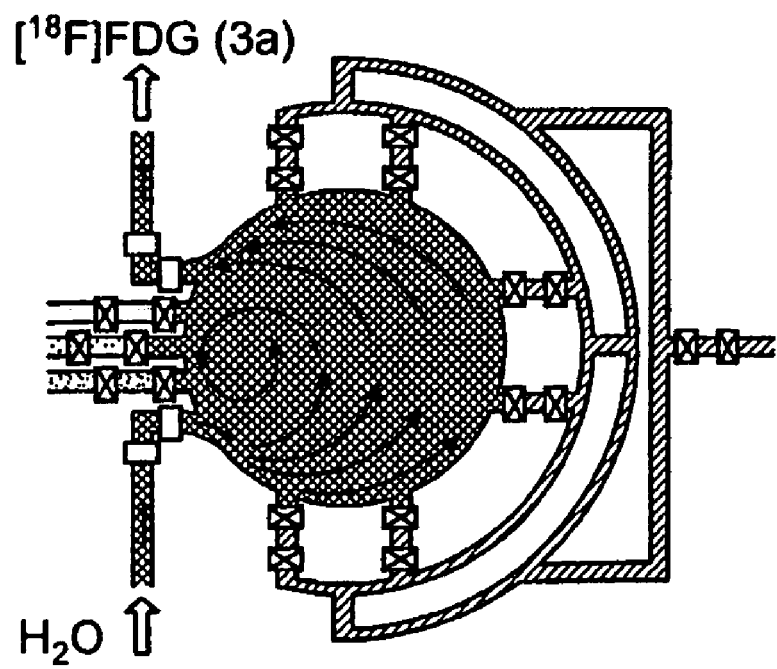

At least some flow channels of a chip of the invention are in fluidic communication with a reactor (described below). In one embodiment, the flow channel is configured as a distribution manifold, and reference herein to a flow channel in fluidic communication with a reactor is intended to include distribution manifolds unless otherwise indicated or clear from context. A distribution manifold is a configuration of a flow channel that serves divide flow into several parts, with the parts being introduced through different ports into the same reactor (see, e.g., FIGS. 11 and 12). In a preferred embodiment, the solution is introduced equally and simultaneously through the ports. In one embodiment, a manifold for introduction of a solution to a reactor, particularly a "coin-shaped" reactor, is fashioned generally as shown in FIGS. 11 and 12. The six-channel manifold allows a solution to enter the chamber from 6 directions simultaneously which leads to faster mixing and shorter reaction times. Simultaneous introduction of liquid is accomplished by having equal path lengths in the channel work from the origin of the manifold to each opening to the chamber. It is also facilitated by having one valve at the source of the manifold and a second set of valves at the entrances of the channels to the chamber—this allows the manifold to be filled first, prior to releasing the fluid into the reactor. In alternative embodiments the distribution manifold has 4-10 channels equidistant from the first splitting point.

Reactors

In one aspect, the invention provides a method for carrying out a chemical reaction using a microfluidic device that has at least one reactor (also referred to as a "reaction chamber"). In some embodiments, the device has multiple reactors, which may be configured serially, in parallel, or otherwise, for carrying out multiple and/or parallel reaction series.

In general, a reactor is characterized by the following three properties:

1. The Reactor is Configured to Fluidically Communicate with at Least One Flow Channel The reactor is configured to fluidically communicate with at least one flow channel. Typically the reactor is in fluidic communication with more than one flow channel such as at least two, at least three, at least four, at least five, at least six, or more than six different flow channels. For illustration, a reactor may be in fluidic communication or configured to fluidically communicate with 1 to 20 flow channels, 1 to 10 flow channels, 2 to 10 flow channels, 3 to 10 flow channels, 4 to 10 flow channels or 5 to 10 flow channels. As discussed above, in some embodiments one or more flow channels are configured as a distribution manifold(s). In one embodiment the reactor is in fluidic communication with at least one distribution manifold (considered a single channel for the purposes of enumeration).

2. The Reactor is Configured to be Fluidically Isolated

The reactor is configured so that is can be fluidically isolated. Typically this is accomplished by closing (actuating) valves so as to prevent liquid flow from a flow channel into the reactor or from the reactor to a flow channel. Thus, when a reactor is fluidically isolated liquid cannot, to any significant degree, flow out of the reactor.

3. The Reactor is Permeable to a Gas But Substantially Impermeable to the Liquid Corresponding to the Gas and to Reactants and Products Dissolved in the Liquid The reactor is adapted for solvent exchange. That is, at least a portion of the reactor wall is selectively permeable so that when the reactor is fluidically isolated (and thus any liquid in the reactor is confined to the chamber) vapor can escape by passing through the reactor wall. Thus, a solvent (e.g., acetonitrile) in liquid phase is contained in a fluidically isolated reactor but escapes the fluidically isolated reactor when converted to gas phase. A liquid solvent is converted to the gas phase by evaporation and/or by heating the liquid and/or reducing the ambient pressure. In one embodiment, the liquid in the reactor is heated to or above its normal (atmospheric) boiling point. In one embodiment, the reactor wall is essentially impermeable to liquid water (thus water does not leak through the chamber wall and out of the device) but is permeable to water vapor. Exemplary solvents to which the reactor wall (or gas permeable portion thereof) is selectively permeable can include one or more of water; acetic acid; acetone; acetonitrile; benzene; 1-butanol; 2-butanol; 2-butanone; t-butyl alcohol; carbon tetrachloride; chlorobenzene; chloroform; cyclohexane; 1,2-dichloroethane; diethyl ether; diethylene glycol; diglyme (diethylene glycol dimethyl ether); 1,2-dimethoxy-ethane (glyme, DME); dimethyl-formamide (DMF); dimethyl sulfoxide (DMSO); dioxane; ethanol; ethyl acetate; ethylene glycol; glycerin; heptane; hexamethylphosphoramide (HMPA); hexamethylphosphorous triamide (HMPT); hexane; methanol; methyl t-butyl; ether (MTBE); methylene chloride; N-methyl-2-pyrrolidinone (NMP); nitromethane; pentane; Petroleum ether (ligroine); 1-propanol; 2-propanol; pyridine; tetrahydrofuran (THF); toluene; triethyl amine; and xylene, and combinations thereof. It will be understood that the reactor wall may be permeable to gas mixtures such as, for example, the mixture created by evaporation of an azeotrope, such as the azeotrope of water and acetonitrile.

In one embodiment, the reactor is formed, at least in part, by a gas permeable elastomeric material, such as an elastomer described above. Certain elastomers, such as PDMS and PFPE, in particular are characterized by outstanding gas permeability to certain solvents.

Other materials (not necessarily considered elastomeric) may also be used. For example, the permeable material may include a polymer (e.g., a single polymer type, a co-polymer, a polymer blend, a polymer derivative, etc.) including polyfluoroorganic materials such as polytetrafluoroethylenes and amorphous fluoropolymers; polystyrenes; polysulfones; polycarbonates; acrylics (e.g., polymethyl acrylate and polymethyl methacrylate); polyethylenes (e.g., high, low, ultra low, and linear low-density polyethylenes); polyvinylchlorides; poly(4-methylpentene-1) ("PMP"); poly(4-methylhexene-1), poly(4-methylheptene-1); poly(4-methyloctene-1), and poly(1-trimethlsilyl-1-pro-pyne).

In some embodiments, the entire interior surface of the reactor (e.g., "floor," "ceiling," and "walls") is composed of a gas permeable material. This may be the case when the device is fabricated from PDMS, for example. In some embodiments, at least a portion of the interior surface of the reactor is defined by a material that is not a gas permeable material (e.g., silicon, glass or metal). For example, for a reactor of the device can have a floor and walls fabricated from glass, and have a "ceiling" fabricated from PDMS (see, e.g., description of composite structures above).

In some embodiments, the device is constructed so that the distance from the interior surface of the reactor to the exterior of the device, or to a vent to the exterior such as the lumen of a vent channel is less than 1000 microns (i.e., the thickness of the gas-permeable material the vapor must pass through to reach the topological exterior of the device). In some embodiments, the thickness of the gas-permeable material is from 1 to 1000 microns, sometimes from 1 to 1000 microns, often from 50 to 500 microns, and most often from 50 to 200 microns, e.g., 100 microns. It will be appreciated that the optimal or appropriate thickness will vary depending on the material and intended use of the reactor. In some embodiments, the device has channels, referred to as "vent channels" positioned to accelerate or facilitate withdrawal of gas from the reactor. Vent channels are described below.

Alternatively the solvent can be evaporated out of the reactor and into an elastomeric or other gas-permeable material and remain in the material (i.e., without any substantial amount of the gas reaching the exterior).

In addition to the properties above, in certain embodiments, a reactor may have one or more of the following properties (related to reactor size, number, shape, and relationship to a chromatography column):

4. The Liquid Capacity of a Reactor May be Large

The volume (or liquid capacity) can vary widely from the nanoliter to microliter range. In certain embodiments the reactor capacity is less than 1 microliter (e.g., 1 nL to 1000 nL, often 100 nL to 500 nL). In certain embodiments, the volume or liquid capacity of the reactor is greater than 1 microliter, sometimes greater than 5 microliters, and sometimes greater than 10 microliters. In certain embodiments, the volume of the reactor is from 1 to 20 microliters, 2 to 20 microliters, 5 to 20 microliters, or 10 to 20 microliters. In certain embodiments, the volume of the reactor is from 1 to 10 microliters, 2 to 10 microliters, 5 to 10 microliters, or 7 to 10 microliters.

5. The Reactor May have a Variety of Geometries

The reactor may have a variety of geometries or interior shapes. The selection of reactor shape will vary with the intended use of the device such as, in some cases, the volume of reactants or solutions to be introduced into the reactor, the quantity of product desired, and other factors. For example, if the reactant is eluted from a column and transported in its entirely to a reactor, the reactor would usually have a volume equal to the elution volume (alternatively, one or more rounds of solvent removal could be used to reduce the volume). Preferably the shape and dimensions of the reactor are selected to allow efficient mixing of solutions introduced into the reactor. Exemplary shapes include tubular, spherical, cylindrical, polyhedral (e.g., a hexahedron), coin-shaped, box-like, bar-bell shaped, and others. In one embodiment the reactor has an irregular shape. In some embodiments, a reactor chamber may include baffles or other structures to increase mixing efficiency.

In one embodiment, the reactor has the form of a flow channel (or loop channel) that can be isolated from other channels to form a closed path through which fluid can circulate (see Example 1, below). Loop channels are described in U.S. Pat. No. 6,767,706. Typically such a reactor has dimensions that fall within the ranges provided above for flow channels (e.g., 200 microns by 45 microns) although larger dimensions can be used to accommodate larger volume reactions. A closed path means that the channel can be temporarily isolated from other parts of the chip, for example by closing valves in any channels which lead into or out of the loop, and that a liquid can then circulate through the path. Pumps such as peristaltic pumps, can be used to circulate liquid. Alternatively, other mechanisms can be used for circulation and/or mixing in the isolated reactor.

In one embodiment, the reactor has the form of a circular loop channel. In one embodiment, the reactor has the form of a loop channel other than a circular channel. See, for example, FIG. 20 of U.S. Pat. No. 6,767,706 for a description of a closed loop channel in which a solution may be circulated or two solutions circulated and mixed.

In some embodiments the reactor has a shape other than a loop channel. In some embodiments the dimensions of the reactor are such that the height, width and length or height and diameter, or the like, vary by no more than a factor of 50 (i.e., the longest dimension is no more than 50-fold as much as the shortest dimension). In other embodiments the dimensions of the reactor vary by no more than a factor of 40, no more than 30, no more than 20, no more than 10, no more than 5 or no more than 2.

In one embodiment the reactor is "coin-shaped." That is, roughly a cylinder with a high diameter to height ratio, usually greater than 5, usually greater than 10, often greater than 15, and sometimes 20 or greater. An exemplary reactor has a height of from 25 to 1,000 micrometers and a diameter of from 1,000 to 20,000 micrometers. An exemplary reactor has dimensions of 250 micrometers (height) by 5000 micrometers (diameter). In one embodiment, the reactor has the shape of a wide and short cylinder (coin-shaped, 250 um in height and 5 to 7 mm diameters). See FIGS. 11 and 12.

In other embodiments the reactor is "box-like." That is, having a rectangular floor and ceiling and a height dimension significantly smaller than the other dimensions (e.g., a high width to height ratio, usually greater than 5, usually greater than 10, often greater than 15, and sometimes 20 or greater). In related embodiments, the reactor has a floor and/or ceiling with the shape of any regular or irregular parallelogram. In other embodiments, the reactor has a floor and/or ceiling with an irregular shape. In other embodiment the interior shape of the reactor is roughly spherical or roughly cubical, or has a different aspect ratio than described above.

In certain embodiments, the reactor does not have the form of a circular flow channel and does not form a closed path. For example, a coin-shaped reactor does not have the form of a circular flow channel and does not form a closed path. In certain embodiments, a reactor has the form of a circular flow channel but has cross-sectional dimensions that do not fall within the ranges provided above for flow channels (<1 mm). In certain embodiments, the interior of the reactor does not have the shape of a tube. In certain embodiments, the reactor does not have the shape of a circular loop channel. In certain embodiments, the reactor does not have the shape of a non-circular loop channel. In certain embodiments, the interior of the reactor does not have the shape of a polyhedron. In certain embodiments, the reactor is not coin-shaped. In certain embodiments, the reactor is not cylindrical. Exemplary shapes include tubular, spherical, cylindrical, polyhedral (e.g., a hexahedron), coin-shaped, box-like, and others.

6. The Device May have a Small Number of Reactors

In certain embodiments, the device has a single reactor. In other embodiments, the device has 2-5 reactors. In other embodiments, the device has 2-10 reactors, or 2-50 reactors. In other embodiments the device may have up to 10,000 reactors.

7. The Reactor is Configured to Fluidically Communicate with a Microfluidic Separation Column or Concentration Loop Including a Microfluidic Separation Column In certain embodiments the reactor is configured to fluidically communicate with a microfluidic separation column. That is, an eluate from the column can be transported from the column to the reactor, or from the reactor to a column. The column can be on the chip (for example, formed in a flow channel or similarly integral to the chip) or external to the chip. In one embodiment the column is on the chip. Exemplary on-chip microfluidic separation columns ("columns") are described below. Examples of off-chip columns include any columns suitable for chromatography of small volumes. An off chip column device may have the fluidic inputs and outputs and controlling valve functions performed by the chip or microfluidic device.

In some embodiments, the device comprises a concentration loop. A concentration loop includes an on-chip separation column (through which a solution can pass), a column inlet, a column outlet, and a flow channel or channels that connect the outlet to the inlet, and sufficient valves such that when valves between the loop and other flow channels are closed, flow channel(s) and the separation column(s) define a closed path through which fluid can circulate. In a preferred embodiment, the concentration loop includes a pump, preferably a peristaltic pump, capable of moving a solution through the closed path such that the solution flows through the column multiple times. See FIGS. 2 and 3 and accompanying text for illustrations of such a column and closed path. In one embodiment, the concentration loop has a generally rectangular configuration. As describe in Example 1, the concentration loop configuration allows a solution to be circulated multiple times though the column to ensure efficient binding of a compound in the solution to the stationary phase of the column and, in a similar manner, allows an elution solution to flow multiple times though the column to ensure a high degree of elution of reactant or product from the column.

In some embodiments, the solution containing the reaction product is transported from a reactor to a column (e.g., an on-chip column) for, for example, purification or concentration of the product. The eluate from the column can be transported back to the reactor for further modification of the produce or solvent system. More often the eluate from the column can be transported to a different reactor. Alternatively the eluate can be transported to another chip component or to an off-chip component (including, for example, a collection vial).

Valves

Valves of the microfluidic device can be selectively actuated (and/or are one-way valves) to regulate flow in and between channels, reactors, and other chip components. Valves of the device serve to block flow within a flow channel, from a flow channel into a reservoir or reactor, from a reservoir or reactor to a flow channel, or at other sites in which liquid flows.

Valves of various types are known in the art, including micromechanical valves, elastomeric valves, solid-state microvalves, and others. See, e.g., Felton, 2003, The New Generation of Microvalves" *Analytical Chemistry* 429-432. Two common approaches to fabrication of microelectromechanical (MEMS) structures such as pumps and valves are silicon-based bulk micro-machining (which is a subtractive fabrication method whereby single crystal silicon is lithographically patterned and then etched to form three-dimensional structures), and surface micro-machining (which is an additive method where layers of semiconductor-type materials such as polysilicon, silicon nitride, silicon dioxide, and various metals are sequentially added and patterned to make three-dimensional structures).

In one embodiment, the valve is a monolithic valve. In a preferred embodiment the valve is a pressure-actuated "elastomeric valve." A pressure-actuated elastomeric valve consists of a configuration in which two microchannels are separated by an elastomeric segment that can be deflected into or retracted from one of the channels (e.g., a flow channel) in response to an actuation force applied to the other channel (e.g., a control channel). Examples of elastomeric valves include upwardly-deflecting valves (see, e.g., US 20050072946), downwardly deflecting valves (see, e.g., U.S. Pat. No. 6,408,878), side actuated valves (see, e.g., US 20020127736, e.g., paragraphs 0215-0219], normally-closed valves (see, e.g., U.S. Pat. No. 6,408,878 B2 and U.S. Pat. No. 6,899,137) and others. In some embodiments a device can have a combination of valves (e.g., upwardly and downwardly deflecting valves). Valves can be actuated by injecting gases (e.g., air, nitrogen, and argon), liquids (e.g., water, silicon oils and other oils), solutions containing salts and/or polymers (including but not limited to polyethylene glycol, glycerol and carbohydrates) and the like into the control channel. Some valves can be actuated by applying a vacuum to the control channel.

In addition to elastomeric valves actuated by pressure-based actuation systems, monolithic valves with an elastomeric component and electrostatic, magnetic, electrolytic and electrokinetic actuation systems may be used. See, e.g., US 20020109114; US 20020127736, e.g., ¶¶0168-0176; and U.S. Pat. No. 6,767,706 B2 e.g., §6.3. One-way valves have also been described (see, e.g., Adams et al., 2005, *J. Micromech. Microeng.* 15:1517-21; and references 6-12 therein)

In some embodiments, pairs of valves are used, with one acting as a "back-up valve" or "double valves." See, e.g., FIG. 11. Back-up valves are used to confine reaction mixtures in the event the primary valve fails (e.g., due to the relatively higher vapor pressure the valves may be subjected to during the solvent exchange process). Bursts of high pressure may be generated inside the reaction chamber that are strong enough to push the valves open at least briefly (e.g., for a fraction of a second). In such an event, if there is back pressure behind the closed valve, such valve may close back down after being briefly opened without loss of pressure inside the reactor. If there is a much lower pressure behind the valve, some liquid may escape from the chamber, in turn pushing the valve open further. The back pressure behind the valves surrounding the reaction chamber is achieved by having a second set of valves a short distance from the first ones.

C. Other Device Components

Vent Channels

In one embodiment, the device has channels, referred to as "vent channels" positioned to accelerate or facilitate withdrawal of gas from the reactor during solvent exchange or reactor filling (e.g., dead-end or blind filling). A vent channel system comprises channels separated from a reactor by a thin gas permeable (e.g., elastomeric) membrane. The vent channels typically lie over or under a reactor (e.g., in a vent layer or control layer). Vapor can be drawn out of the reactor, pass through an intervening gas permeable material (such as an elastomer), and enter the vent channels(s). Vapor can diffuse into the vent channel or removal can be accelerated by reducing the pressure in the vent channel relative to the reactor chamber. This reduction can be achieved, for example, by flowing gas through the vent channel(s) or drawing a vacuum through the channel(s), as described below, or by any other method that reduces vent channel pressure. Thus, vent channels can be used for accelerating evaporation to concentrate a solute and reduce the volume of a liquid in a chamber. This mechanism for accelerating solvent evaporation is particularly valuable when a large (microliter) volume reactor is used.

The dimensions of vent channels can vary widely. In an exemplary aspect, vent channels have at least one cross-sectional dimension in the range of 0.05 to 1000 microns, often 50 to 500 microns, and most often 100 to 400 microns. In some embodiments, the channel height is not more than about 500 microns or less than about 20 microns (in some embodiments, not more than about 250 microns or less than about 50 microns) and the channel width is not more than 5000 microns or less than 20 microns). In one embodiment, vent channels have rectangular cross-sectional dimensions of about 250 microns×250 microns. In some embodiments, vent channels preferably have width-to-depth ratios of about 1:10 to 100:1, such as between about 2:1 and 1:2, and sometimes about 1:1. In embodiments in which a vacuum is applied to a vent channel dimensions may be selected to avoid collapse of the channel under vacuum (e.g., higher height:width ratios). However, the vent channels are not limited to these particular dimensions or proportions.

As noted above, in some embodiments, the lumen of the vent channel(s) is separated from the interior of the reactor by less than 1000 microns, such as from 10 to 1000 microns, often from 50 to 1000 microns, often from 50 to 500 microns, and most often from 50 to 200 microns, e.g., 100 microns. In one embodiment, a vent is placed above the chamber consisting of a radiator of 250×250 micron channels separated from the chamber by a 100 micron membrane (gas-permeable). See, e.g., FIG. 11.

With reference to an elastomeric or partially elastomeric device, a system of vent channel can lie in an elastomer layer one side of which constitutes a portion of the interior surface of the reactor. For example, in a "wholly" elastomeric device the vent channels may lie in the elastomer layer above or below the flow channel layer (and, for devices with control channels, on the side of the flow layer opposite the control channel layer or in the control channel layer). Vent channels may also be incorporated into the flow channel layer. In some embodiments, providing vent channels above the reaction chamber is the optimal arrangement. However, it is generally easier to fabricate an MSL chip with the vent below the chamber (e.g., as part of the control layer). Dead-end filling rates were similar in both arrangements. It was observed that solvent evaporation, while facilitated significantly by both kinds of vents, was less efficient with the bottom vent location in part because in this arrangement, vapors condensed on the ceiling of the reaction chamber.

Figure 14:
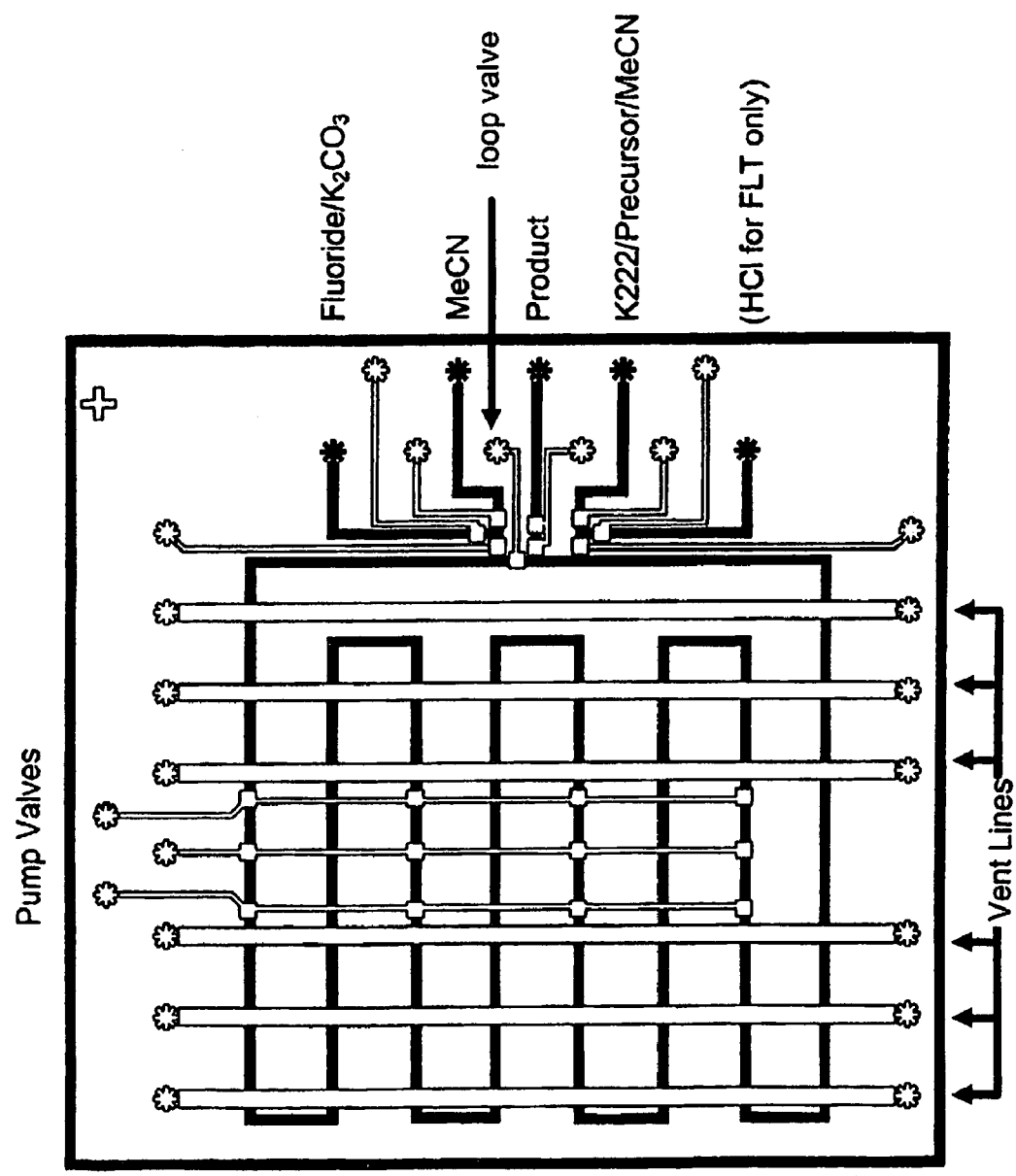
FIG. 14 shows the design of a device used to synthesize 2-(1-(6-[(2-[18F]fluoro-ethyl)(methyl)amino]-2-naphthyl) (FDDNP). Flow channels, including the reactor loop are shown in blue, Control channels are shown as thin red lines. Vent channels (400 microns wide and 25 microns high) are shown using thick red lines. Reagents can be introduced in a variety of ways. Shown is one way to introduce reagents for FDDNP synthesis, i.e., fluoride/K2CO3 solution introduced via the top channel, and precursor/Kryptofix solution are introduced through a lower channel. MeCN can be introduced via the second line from the top while keeping the valve immediately above the center line closed to flush product out of the reactor and through the exit channel as shown.

In one embodiment, vent channels can function passively (by providing a relatively short path from the isolated reactor to the topological exterior of the device). The devise shown in FIG. 14, has six vent channels ("vent lines") in communication with the atmosphere. The vent channels in FIG. 14 are situated in the control layer. In other embodiments, the use of a stream of gas, or, preferably application of a vacuum, can significantly accelerate the rate of solvent evaporation. Thus, in one embodiment, the vent channel(s) are optionally configured with a vacuum pump (or equivalent device) to draw a vacuum in the vent channels and withdraw gas from the reactor. The vacuum pump can be on continuously or actuated while certain chemical processes are underway. In an alternative embodiment, dry gas (e.g., air or $N_2$) can be flowed through the channel to remove vapor from a reactor.

Application of vacuum to the vent channel allows fast removal of gas from the chamber when the latter needs to be filled with fluid. Also during evaporation, it allows removal of solvent vapors. As a result, not only it can it speed up the evaporation, but it also reduces the vapor pressure, which allows some solvents to be removed at lower temperatures. Use of a vent channel system can also reduce pressure on closed valves during the evaporation steps.

A number of vent configurations are possible. In a preferred embodiment, the vent has two open ends to facilitate flushing the vapors (which may condense inside) out of the chip (for example, by applying $N_2$ gas). See FIG. 20.

A vent system also can be configured so as to not accelerate evaporation at certain times in a reaction or series of reactions when such acceleration is not desired due to reaction kinetics or for other reasons. The functioning of a vent system can be modulated by ceasing gas flow or turning off a vacuum source, as appropriate. The accelerated evaporation caused by passive vents can be eliminated or reduced by filling the vents with an oil or similar fluid.

Usually a vent channel system is localized over a reactor or set of reactors rather than being, for example, distributed uniformly throughout the area or footprint of the device. In one embodiment, a substantial portion of a vent channel overlies a single chamber. In this context, a substantial portion means that at least 10% of the length of the vent channel lies over the chamber, preferably at least 20%, and most preferably at least 30%, and sometimes at least 50% of the length of the vent channel lies over the chamber. This is illustrated in FIG. 11B in which about 30% of the length of the vent channel (blue) lies over the 5 ul coin-shaped reactor. Equivalently, in one embodiment, not more than 90%, preferably not more than 80%, most preferably not more than 70%, and sometimes not more than 50% of the length of the channel lies over a region or regions of the device other than a solvent exchange chamber. In one embodiment, a substantial portion of a vent channel overlies a single chamber. In this context, a substantial portion means that at least 10% of the length of the vent channel lies over the chamber, preferably at least 20%, and most preferably at least 30%, and sometimes at least 50% of the length of the vent channel lies over the chamber.

In a related embodiment, a device has more than one reactor and a substantial portion of a vent channel overlies a two or more chambers of a device. In this context, a substantial portion means that at least 10% of the length of the vent channel lies over the chambers, preferably at least 20%, and most preferably at least 30%, and sometimes at least 50% of the length of the vent channel lies over the chambers. Equivalently, in one embodiment, not more than 90%, preferably not more than 80%, most preferably not more than 70%, and sometimes not more than 50% of the length of the channel lies over a region or regions of the device other than one of the solvent exchange chambers.

Evaporation can be accelerated by any method for introducing a differential in the chemical potential for the gas molecule so that it is lower outside the chamber than inside, including increasing pressure within the reactor, reducing pressure or solvent concentration outside the reactor, placing or flowing a solution in which the solvent gas is highly soluble in a microchannel or chamber separated from the reactor chamber by the gas-permeable (e.g., elastomeric) membrane.

The invention provides methods for rapidly removing solvent (e.g., water, acetonitrile, alcohols) from a chamber using the methods above. In some embodiments the evaporation is accelerated by heating. In some embodiments heat is not used. For example, a large volume of solvent (e.g., a volume bounded by the range having a lower value of 1, 2, 3, 4, 5, 6, 7, 8, 9, or 10 microliters and an upper value of 20, 15, 10 or 5 microliters, where the upper value is greater than the lower value) can be evaporated (i.e., at least 90%, preferably at least 95% of the volume is evaporated) rapidly (i.e., less than 3 minutes, preferably less than 2 minutes, more preferably less than 1 minute, more preferably less than 45 seconds, and sometimes less than 30 seconds). In another embodiment a solvent volume between 100 and 1000 nanoliters is rapidly evaporated from the chamber (e.g., preferably less than 1 minute, more preferably less than 45 seconds, and sometimes less than 30 seconds).

In a different approach, solvent can be removed by adding a precipitant causing the reactants and/or product to be precipitated. By using a sieve valve, partially opened valve, or other filtering feature the precipitant can be trapped, the solvent eluted and replaced and the precipitant re-dissolved into solution using a second solvent system introduced through any of the valves.

Separation Devices (Chromatography Columns)

In one embodiment, the device includes one or more separation devices used to separate, purify or concentrate reactants, products or other compounds. Separation devices may be based on electrophoresis, centrifugation, and other separation methods. In some embodiments the separation device is a miniaturized chromatographic column (i.e., a microfluidic separation column) adapted to perform a chromatographic separation process. One particularly useful separation process is liquid chromatography, which may be used with a wide variety of sample types and encompasses a number of methods that are used for separating ions or molecules that are dissolved in or otherwise mixed into a solvent. As used in this context, "sample" refers to a solution containing a product, reactant or other reagent to be concentrated, purified, separated from other components of the solution and/or transferred to a different solvent.

In liquid chromatography a liquid "mobile phase" (typically consisting of one or more solvents) carries a sample containing multiple constituents or species through a separation medium or "stationary phase." Stationary phase material typically includes a liquid-permeable medium such as beads, packed granules (particulate material) or a porous monolith disposed within a tube or a channel boundary which may be derivatized, bound to or coated with a compound(s) that specifically interacts with a compound in solution as it passes through the column. In one embodiment the chromatography column is a microfluidic channel having a stationary phase that is bonded to a functional group on the inner surface of the channel.

The mobile phase may be forced through the stationary phase using pumps, voltage-driven electrokinetic flow, or other methods for generating a pressure differential. After a sample is applied to the column, components of the sample will migrate according to interactions with the stationary phase and the flow of such components are retarded to varying degrees. Individual sample components (e.g., reactants or products) may reside for some time in the stationary phase until conditions (e.g., a change in solvent) permit a component to emerge from the column with the mobile phase.

The columns of the present invention can be selected to retain the reactant/product when the sample is applied to the column and release it under certain conditions such as, typically, application of an elution solvent or elution solution. Alternatively, the reactant/product may pass rapidly though the column when the sample is applied, and other (undesired) components of the sample may be retained.

Exemplary separation devices are described in US 2002/0164816; and US 2004/0115838, e.g., para 0327-0333, and U.S. Pat. No. 6,752,922 (describing microfabricated chromatography column configured in a rotary channel). Examples of chromatographic separation material can include a bead material (e.g., cross-lined agarose or dextran beads, functionalized silica, polymer-coated silica, or porous silica particles, resins such as copolymers of styrene and divinylbenzen, and divinylbenzene and acrylic or methacrylic acid, metal and other materials) which may be derivatized, bound to or coated with a compound(s) that specifically interacts with a compound in solution as it passes through the column. For example and without limitation, chromatographic separation material can be adapted for many types of chromatography including gel filtration, anion exchange, cation exchange, hydrophobic interaction, size exclusion, reverse phase, metal ion affinity chromatography, IMAC, immunoaffinity chromatography, and adsorption chromatography. For example and not limitation chromatographic separation material that can be used in the column module can be ion exchange resins (e.g., anion-exchange resins, cation-exchange resins), affinity chromatography resins, size exclusion chromatography resins, and others. Examples of useful resins include HEI X8 (BioRad Corp.) and Source 15Q (Amersham Biosciences).

Exemplary On-Chip (Integral) Columns

In one embodiment, a column is constructed by trapping stationary phase beads (e.g., ion exchange beads) in a fluid channel isolated with partially closed valves (see, Hong et al, 2004, "A nanoliter-scale nucleic acid processor with parallel architecture" *Nature Biotechnology* 22:435-39) or sieve valves. Sieve valves are depicted in FIG. 3. Sieve valves (FIGS. 3A and C) are composed of a square-profile fluidic line and a regular control membrane, and thus differ from a normal valves (FIGS. 3A and C) based on a round-profile fluidic line. In general, when valves operate, the valve membranes deflect in an elliptic shape (FIGS. 3*c* and *d*). In the case of normal valve (FIG. 3C), the deflected membrane is fully compliant to the round-profile fluidic channel lead to complete close of the valve. For a sieve valve (FIG. 3D), a deflected membrane partially closes the valve, generating two small gaps the two channel edges of the square-profile channel. When a solution (e.g., an aqueous solution) containing suspended beads in appropriate sizes is introduced into the fluidic chambers, the beads are trapped by the sieve valves while the solution is allowed to pass through the closed sieve valve. By using this design, a variety of miniaturized columns filled with different type of beads (e.g., ion exchange resin, silica gel and $C^{18}$ can be achieved for applications such as ion extraction, filtration, purification and chromatography). In one embodiment, the favorable dimensionalities of beads are in the range of 2 μm to as 50 μm depending on the specific geometry to the channels and valves.

Sieve valves can be constructed using standard multilayer soft lithography (MSL) methods (see, e.g., Unger. et al., *Science* 2000, 288:113-16 and patent publications US20040229349; US20040224380; and US20040072278). For example, a device with sieve valves has been constructed of three layers of the silicone elastomer polydimethylsiloxane (PDMS) (General Electric) bonded to a RCA cleaned #1.5 glass coverslip. The device was fabricated as described in Fu et al., *Nat Biotechnol* 1999, 17:1109-11 with slight modifications (Studer et al., *J. Appl. Phys.* 2004, 95:393-98). Negative master molds were fabricated out of photoresist by standard optical lithography and patterned with 20,000 dpi transparency masks (CAD/Art Services) drafted with AutoCAD software (Autodesk). The flow layer masks (column portion and channel portion) were sized to 101.5% of the control layer masks to compensate for shrinking of features during the first elastomer curing step. The flow master molds were fabricated out of 40 μm AZ-100XT/13 μm SU8-2015 photoresists (Clariant/Microchem) and the control molds were cast from 24 μm SU8-2025 (Microchem).

In order to implement sieve valves, the flow channel portion where columns are to be constructed has a rectangular profile in cross section. Therefore, in one embodiment, a multistep lithography process is used for microfluidic devices composed of both sieve valves and conventional valves (Unger et al., 2000, *Science* 288:113-116). In one approach, for example, the column resist is spun onto a silicon wafer and processed, followed by processing the resist for the conventional fluid channels. The fabrication of molds having a rounded flow structure is achieved by thermal re-flow of the patterned photoresist. Negative photo-resists such as SU8 rely on thermal polymerization of UV-exposed regions, and therefore can not be reflowed. In order to be compatible with membrane valves, flow channel sections are defined using a positive photoresist such as AZ-50 (Clariant Corp. Charlotte, N.C.).

Once the fluid channels are processed, the two layer mold is heated (e.g., baked on a hot plate of 200 degrees C. for 2 hours) so that the photoresist can reflow and form a rounded shape, which is important for complete valve closure (see Unger, supra). A hard bake step is also implemented between resist steps, in order to make the column resist mechanically robust for downstream processing. Most devices that have sieve valves also have conventional valves, and have both rounded and non-rounded (e.g., rectangular) flow channels.

As noted above, the separation device can fluidically communicate with the reactor. In one embodiment a reactant is concentrated or purified and then transported to a reactor. In another embodiment a product is concentrated or purified and then transported to a reactor. It will be recognized that in a series of chemical reactions some compounds will be both reactants and products.

Exemplary Microscale (Off-Chip) Columns

In certain embodiments, the microfluidic system includes an off-chip chromatography device such as a microscale column. As used herein and in this context, off-chip means the column is not integral to the CRC, and specifically that the column material is not situated within a microfluidic channel in the device. Thus, a column that is "off-chip" in this sense can be attached to the chip, placed in a carrier module in which the chip is also placed, or fluidically tied to the chip by tubing. In these cases the chromatography column can be removed from the chip without destroying the device.

Advantages of off-chip columns for certain embodiments can include increased capacity and increased through-put, due in part to use of a column having a larger size (e.g., a microscale column) than can be conveniently fabricated within a microfluidic channel. Microscale columns useful in the present devices and methods include (but are not limited to) columns with a column volume between about 1 microliters and about 20 microliters, usually between about 5 microliters and about 10 microliters.

In certain applications an off-chip design may have advantages. Using the synthesis of [$^{18}$F]FDG as described in Example 3 as an example, advantages of using a microscale off-chip column include (a) the channels that supply the target water into the ion exchange column can be be wider, resulting in much faster loading rates; and (b) the column capacity can be increased, since at least some resin can be packaged more tightly than by collecting the beads by filtration. Other advantages can include the ability to use a modular cartridge design in which a pre-packed ion exchange cartridge is placed on the carrier module. The off-chip design also allows use and testing of a greater variety of resins, including resins having a bead size larger than 15 microns. In one embodiment the column volume is 2.2 microliters, the exchange resin is AG-1 X8 (200-400 mesh), the dead volume left for the solvent is <1 uL. Using a prototype column of this design up to 800 mCi of $^{18}$F$^-$ could be loaded with 99.5% trapping efficiency from 1.8 mL of target water. A release efficiency of 92.7% with 20 uL of 0.05M $K_2CO_3$ was observed. Off-chip columns are also useful when the stationary phase is destroyed during chromatography (for example, as in acid-neutralization chromatography using an alumina column). Columns can be replaced and devices reused.

It will be appreciated that a particular microfluidic system may have one or more (up to several hundreds or more) on-chip columns, may have one or more off-chip columns, and may employ both on-chip and off-chip columns. It will also be clear that CRCs may include multiple columns, which may have different functions in a chemical reaction or other process, and may contain different resins or other chromatography material.

Pumps

Microfluidic devices of the present invention may include one or more integral pumps for transport of fluids through flow channels and into and out of other device components (e.g., column or reactors) or the device itself. Suitable pumps can be electronic, electrostatic, magnetic, mechanical, syringe, pneumatic, or peristaltic. Preferably peristaltic pumps, such as those described in U.S. Pat. No. 6,408,878 B2, are used. Alternatively pumps can be external to the chip. Pumps are also used to transport fluids (e.g., water) through control channels to actuate valves or guard channels to minimize evaporation is selected regions of the chip. Pumps are also used to draw a vacuum in, for example, vent channels.

Temperature Control Components

In certain embodiments, a solvent, reaction mixture, reagent or product is heated or cooled to initiate, maintain or optimize a reaction or preserve the reagent or product. Thus, the devices and systems of the invention may include temperature control systems that modulate temperature of the entire device or a particular region or component of the device (e.g., reservoir or reactor). Examples of suitable temperature control systems include, but are not limited to, Peltier devices, resistive heaters, heat exchangers and an indium tin oxide element (see e.g., U.S. Pat. No. 6,960,437 B2). Solutions also can be heated using a light source such as a laser. A number of different options of varying sophistication are available for controlling temperature within selected regions of the microfluidic device or the entire device. Thus, as used herein, the term temperature controller is meant broadly to refer to a device or element that can regulate temperature of the entire microfluidic device or within a portion of the microfluidic device.

In some embodiments, it is useful to incorporate sensors detecting temperature at various regions of the device. One structure for detecting temperature is a thermocouple. Such a thermocouple could be created as thin film wires patterned on the underlying substrate material, or as wires incorporated directly into the microfabricated elastomer material itself. Temperature can also be sensed through a change in electrical resistance. For example, change in resistance of a thermistor fabricated on an underlying semiconductor substrate utilizing conventional techniques can be calibrated to a given temperature change. Alternatively, a thermistor could be inserted directly into the microfabricated elastomer material. Still another approach to detection of temperature by resistance is described in Wu et al., 2001, "MEMS Flow Sensors for Nanofluidic Applications", Sensors and Actuators A 89 152-158. Thermo-chromatic materials Monitoring Components In certain embodiments, the microfluidic system or device includes monitoring devices and signal detectors. Exemplary signal detectors monitor visible, fluorescent, and UV light (intensity, scattering, absorption) luminescence, differential reflectivity, electrical resistance, resistivity, impedance, and voltage. Applications can also utilize scintillation proximity assay techniques, confocal laser scanning, radiochemical detection, fluorescence polarization and other methods.

Control Channels

A "control channel" is a channel separated from a flow channel by an elastomeric membrane that can be deflected into or retracted from the flow channel in response to an actuation force (i.e., acting as a "valve"). The dimensions of control channels can vary widely but typically include at least one cross-sectional dimension (e.g., height, width, or diameter) less than 1 mm, preferably less than 0.5 mm, and often less than 0.3 mm. For example, in one embodiment, a control channel has dimensions of 250 micrometers wide by 250 micrometers high. In another embodiment, a control channel has dimensions of 300 micrometers wide by 50 micrometers high. See, Unger et al., 2000, Science 288:113-116; US 2004/0115838; and PCT publications WO 01/01025; WO 2005030822 and WO 2005084191.

Guard Channels

In certain embodiments, the microfluidic device contains guard channels in an elastomeric layer. Guard channels are channels formed within a elastomeric device through which a solution (e.g., water) can be flowed to increase the water vapor pressure within the elastomeric material, thereby reducing evaporation at selected portions of the device and/or at selected times in a reaction series. Guard channels are described in U.S. Patent Application Publication No. 2003/0138829.

Vias

A "via" refers to a channel formed in an elastomeric device to provide fluid access between an external port of the device and one or more flow channels. Thus, a via can serve as a sample input or output, for example. Also encompassed are "vertical vias" or interconnects between the elastomer layers (which may be created by lithographically patterning an etch resistant layer on top of a elastomer layer, then etching the elastomer and finally removing the etch resist before adding the last layer of elastomer). See U.S. Pat. No. 6,408,878 and patent publication US20050166980.

Other properties of individual reactors will be apparent on review of this disclosure. For example, in most embodiments of the invention the reactor is free of cells, cellular material, or nucleic acids, and/or occurring polypeptides from a biological source (cell, virion, etc.).

Section 4. Synthesis of a Reaction Product

As discussed above, the invention provides methods for carrying out a chemical reaction, or a series of chemical reactions, using a microfluidic device. In a basic aspect, the method involves introducing a solution containing one or more reactants into a microfluidic reactor, then fluidically isolating the reactor, and then removing solvent from the fluidically isolated reactor. A number of optional additional steps are described below. In particular, methods for effecting solvent exchanges, conducting sequential chemical reactions in the reactor, and functionally integrating various components of the microfluidic device are described.

In a first basic aspect, a solution containing a reactant in a solvent system is introduced into the reactor via microfluidic flow channels. For ease of reference, this is a first solution containing a first reactant in a first solvent system. The reactor is fluidically isolated and all or a portion of the solvent system is removed from the fluidically isolated chamber while retaining the first reactant. The reactor is fluidically joined to a channel, and a second solvent system is introduced in which the reactant is resolubilized. The second solvent system may contain a reactant or catalyst, as described below. Alternatively, the reactant in solution in the second solvent system can be removed from the reactor and transported to a different reactor, separation column, or the like, to undergo further chemical processes.

In another basic aspect, two different solutions, each containing a reactant in the chemical reaction, are introduced into the reactor via microfluidic flow channels. For ease of reference, the first solution contains the first reactant in the first solvent system, and the second solution contains the second reactant in the second solvent system. The first and second solvent systems may be the same or different, and each may consist of a single solvent (e.g., acetonitrile) or a combination of solvents (e.g., acetonitrile and water). Each solution optionally contains additional solutes, including, in some cases, additional reactants.

Introducing a solution into a reactor can be accomplished using any fluid transport mechanism suited to the particular microfluidic device. Typically solutions are pumped (e.g., with a peristaltic pump). The two solutions can be added simultaneously or in either order using any of a number of filling strategies. In one strategy, two solutions are introduced simultaneously, and the reactor is then fluidically isolated. In a second strategy, the first solution is introduced to partially fill the reactor, the second solution is then added to further (or completely fill the reactor) and the reactor is then fluidically isolated. This strategy is illustrated in Example 3, below, in which, inter alia, the reactor is two-thirds filled with a mixture of $^{18}F^-$/Kryptofix222/$K_2CO_3$ (in MeCN), and then mannose triflate (in MeCN) is introduced to fill the reactor. In a third strategy, the reactor is completely filled with the first solution, the second solution is then introduced, displacing a portion of the first solution, and the reactor is then fluidically isolated. In a fourth strategy, the reactor is completely filled with the first solution, the reactor is isolated, all or some of the first solvent system is withdrawn, the reactor is fluidically joined, the second solution is introduced, and the reactor is again fluidically isolated. This fourth strategy is illustrated in Example 1, below, in which, inter alia, (1) an aqueous solution containing $^{19}F$—KF was introduced into the reactor (reaction loop), (2) the reactor was fluidically isolated, (3) water was removed from the reactor while retaining the KF, (4) the reactor was fluidically joined, (5) D-mannose triflate and Kryptofix 222 were added, and (6) and the reactor was again fluidically isolated. Introduction of solutions into the reactor can be facilitated using vent channels to withdraw gas (e.g., air) that may occupy the reactor before filling (see Example 3, FIG. 12).

Additional solvents or solutions containing additional reactants, catalysts, buffers, reagents, reaction components, and the like can be introduced into the reactor via flow channels at any time the reactor is not fluidically isolated, including before, during and/or after the introduction of the first solution and/or before, during and/or after introduction of the second solution. Addition may be in any order consistent with the chemistry of the desired reaction. Further, it will be appreciated that, as illustrated in the examples, the reactor can be fluidically isolated or joined at various times in the filling process to facilitate filling.

Removal of a Solvent System

The invention provides a method for solvent exchange in which a solvent system is removed from a reactor that is permeable to a solvent in vapor, but not liquid, form. In certain embodiments the method includes a step of removing all or a portion of a solvent system (or individual component solvents) from the fluidically isolated reactor while retaining, and optionally without removing, a solute, such as a reactant or product, from the reactor. Solvent is removed by evaporation through a gas permeable portion of the reactor chamber wall. As discussed in Section 3, above, at least a portion of the reactor wall is permeable to the vapor form of a solvent, but not the liquid form, allowing vapor to escape a fluidically isolated reactor. As discussed in Section 3 an exemplary reactor is fabricated at least in part from a gas permeable elastomeric material. Exemplary elastomers include polydimethylsiloxane and perfluoropolyether, which are characterized by outstanding gas permeability. In one embodiment the reactor is fabricated entirely or substantially from elastomer. In some embodiments, the rate of evaporation is accelerated by application of heat and/or use of vent channels.

The presence of gas permeable materials in the reactor allows the user to (i) carry out solvent exchange(s) in the reactor; (ii) concentrate reactants, products and other solutes in the reactor; (iii) change the composition of solutions in the chamber (e.g., by differentially evaporating different solvents in a solvent system, based on different boiling points); and carry out other useful processes.

Solvent exchange can be accomplished by removing a first solvent from a fluidically isolated reactor, fluidically joining the reactor to flow channel(s) by opening a valve or valves, and introducing a second solvent into the reactor via a flow channel. The valve(s) can then be closed to again isolate the reactor. Additional reaction components (such as reactants) can also introduced and may be, for example, introduced in solution with the solvent system. Example 1 illustrates solvent exchange. As described, aqueous $^{18}F$-fluorine was introduced into the reactor, the reactor isolated, the water (solvent) was removed by heating, and a different solvent, acetonitrile, was then introduced into the reactor. It is not necessary, and is sometimes undesirable, to remove all of a first solvent during a solvent exchange step (for example, if reactants are very difficult to resoluablize). A solvent exchange step can involve removal of at least about 5%, at least about 10%, at least about 25%, at least about 50%, at least about 75%, at least about 80%, at least about 90%, at least about 95%, at least about 99%, or all of a solvent contained in a reactor.

In one aspect the invention provides a method for removing solvent from a reaction chamber (reactor) of a microfluidic device by (i) providing a microfluidic device comprising a reactor that contains a solute compound and a solvent system and (2) removing at least 25%, preferably at least 50% of the solvent system from the reactor while retaining the solute compound in the reactor, whereby the amount of the solute compound in the reactor per unit volume of the solvent system in the reactor is increased. In one embodiment the solute compound remains in solution and the concentration of the solute in the solution is increased. In one embodiment the solvent is other than water. In one embodiment the solvent is water.

In one embodiment of this method the solute compound is a radionuclide or a molecule comprising a radionuclide. The radionuclide can be, for example, [$^{11}C$], [$^{124}I$], [$^{18}F$], [$^{124}I$], [$^{13}N$], [$^{52}Fe$], [$^{55}Co$], [$^{75}Br$], [$^{76}Br$], [$^{94}Tc$], [$^{111}In$], [$^{99}Tc$], [$^{111}In$], [$^{67}Ga$], [$^{123}I$], [$^{125}I$], [$^{14}C$], or [$^{32}P$]. Preferably the solute compound is [$^{18}F$]fluoride or a molecule comprising [$^{18}F$]fluoride such as [$^{18}F$]-potassium fluoride. In some embodiments the solute compound is a cryptand, such as Kryptofix 222. In embodiments, the solute compound is i) 2-deoxy-2-$^{18}F$-fluoro-1,3,4,6-tetra-O-acetyl-beta-D-glucose; ii) 2-(1-{6-[(2-(p-toluenesulfonyloxy)ethyl)(methyl) amino]-2-napthyl}ethylidine)malononitrile; iii) D-mannose triflate; a compound listed in Table 1. In preferred embodiments of the invention, more than one solute compound is retained in the reactor. For example, 2, 3, 4, 5, 6 or more than 6 solutes may be retained in the reactor.

Generation of the Reaction Product

In certain embodiments, the reactor is maintained in a fluidically isolated state (e.g., valves are kept closed) for a time and under conditions sufficient for a reaction product to accumulate in the reactor.

For certain combinations of reactants and reaction conditions, little or no product will be formed until sufficient time has passed for the reaction to take place (as determined by reaction kinetics) and/or the reaction is initiated or accelerated by a change in the environment of the fluidically isolated reactor (e.g., heating of the reaction mixture).

In other cases, product may begin to form even before the reactor is isolated, such as soon as the reactants are intermixed, or upon introduction of a component that changes the reaction environment (a change in the solvent system, introduction of reactants, catalysts, salts, buffers, ions, etc.). If the reaction is rapid, product may be completely generated before the reactor is isolated. In one embodiment, a substantial amount of the reaction product is produced prior to the step of fluidically isolating the reactor. By "substantial amount" is meant more than 80%, preferably more than 90%, and sometimes more then 95% of the total yield of the reaction. In another embodiment, an insubstantial amount of the reaction product is produced prior to the step of fluidically isolating the reactor. By "insubstantial amount" is meant less than 20%, preferably less than 10%, and sometimes less than 5% of the total yield of the reaction. If the reaction is less rapid, a portion of the product may be generated before the reactor is isolated and product will continue to accumulate for a period after the reactor is isolated). In any event, the reactor is maintained in a fluidically isolated state for a time and under conditions sufficient for a reaction product to accumulate in the reactor. If, as a limiting example, the reactants react immediately and completely when introduced into the reactor and prior to fluidic isolation of the reactor, "maintaining the reactor in a fluidically isolated state for a time and under conditions sufficient for a reaction product" includes a "zero time;" that is, accumulation of the reaction product is complete at the time the reactor is isolated.

As noted above, for many reactions little or no product will be formed until the reaction is initiated or accelerated by a change in the environment such as heating of the reaction mixture. Advantageously, a solution inside a microfluidic reactor fabricated, entirely or in part, from certain elastomers (e.g., PDMS), can be heated above normal (atmospheric) boiling point or the solvent or solution, generating a high-temperature and high-pressure reaction environment. As a result, the reaction kinetics are accelerated, and reaction time can be shortened. Pressure is mediated not only by the heat supplied to the chip, but also by the porosity of the elastomer matrix. In this example, PDMS plays a role akin to the safety valve of a pressure cooker that regulates the "cooking pressure" within a critical range.

Mixing Solvents, Reactants and Reagents

Chemical reactions and other chemical processes may require that the reaction components be actively mixed, or may be accelerated with active mixing. Several methods for mixing are described below, for illustration and not limitation. Method (a) is particularly relevant to a reactor configured as a loop (including non-circular structures described in U.S. Pat. No. 6,767,706). Methods (b)-(g) are particularly relevant to reactors that have a large volume, such as a coin-shaped reactor.

a) Loop Channel Mixing

Solutions can be mixed in a loop channel (or "circulation loop channel") by introducing the solutions into the loop channel and activating a pump (e.g., peristaltic pump) associated with the loop channel to circulate at least one of the different fluids about the circulation loop channel to mix the different fluids. See U.S. Pat. No. 6,767,706.

b) Bottom-Up Mixing

Figure 19:
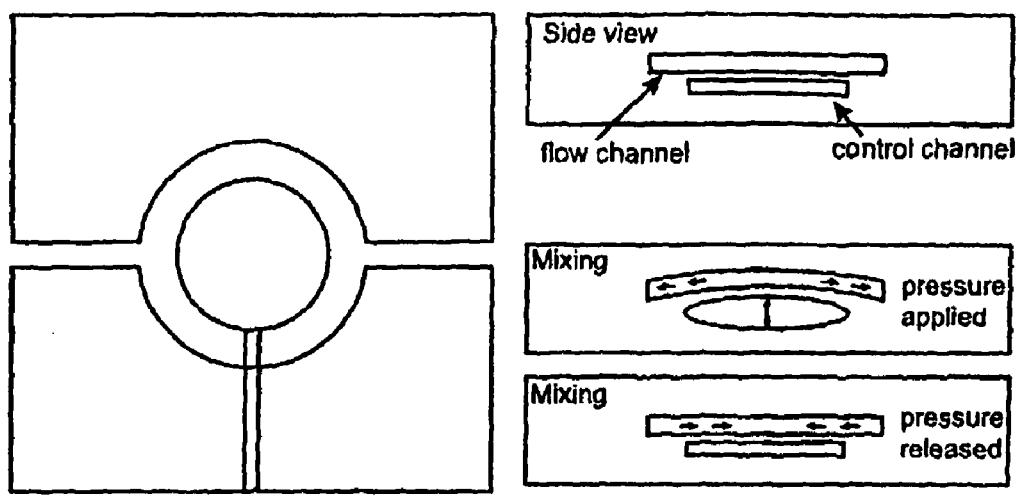
FIG. 19 shows a microscale reaction chamber with a large bottom-up mixer.

Mixing can be achieved by causing the membrane of the large flat round dead end channel (denoted "control channel" in the figure) below the reactor to be actuated (i.e., expand and contract) at a certain frequency as illustrated in FIG. 19. This method has certain disadvantages: (i) There is little room left in the control channel layer for the evaporation radiator (if a bottom vent location is used); (ii) The membrane between the control channel and the reaction chamber may collapse during the final curing of the chip because of large surface area/thickness ratio; (iii) The mixing efficiency may be limited; (iv) Complete elution of product from the reactor may be difficult; (v) The problem of leaving some product behind in the reactor after final elution still exists; (vi) The dead-end channel takes up valuable space in the (in some embodiments) control channel layer.

c) Pulse Mixing

Figure 20:
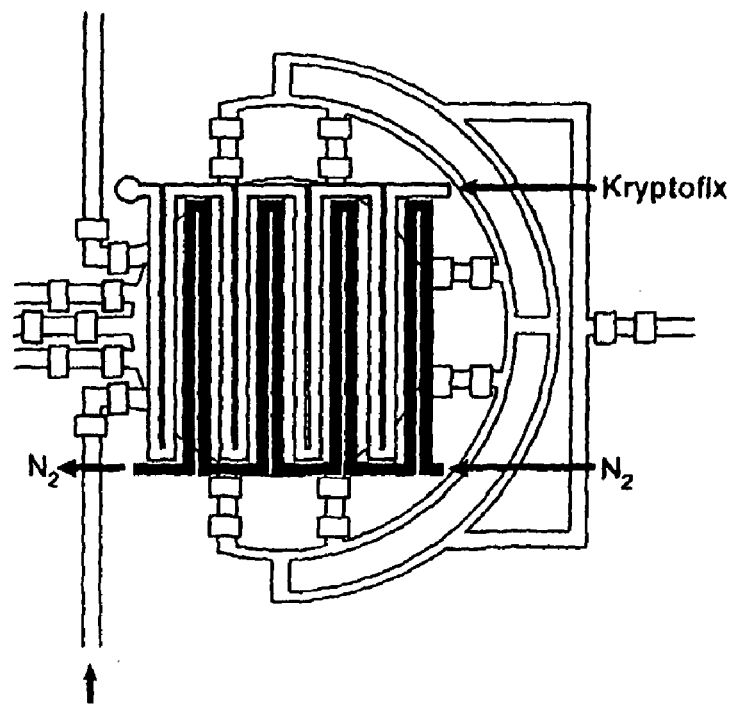
FIG. 20 shows a radiator mixer integrated with the radiator evaporator.

In one approach to mixing, a dead-end serpentine channel is positioned underneath the reactor, e.g., in the control layer underneath the reaction chamber. The dead-end channel can be filled with liquid (e.g., Krytox® oil, Dupont) and serve as a mixer by introducing waves in the reactor by pulsing the pressure applied to this channel. This system can also be used to remove product from the reactor (e.g., the same waves are oriented towards the exit channel of the reactor). To empty the reactor the serpentine channel is actuated to generate wave. In addition, gas (e.g., $N_2$) can be introduced into a vent channel (instead of vacuum) to building up pressure inside the reactor. FIG. 20 illustrates a double radiator system in which the vent channel (shown with $N_2$) and the liquid-filled dead-end channel ("Krytox"). This figure also illustrates another exemplary vent channel configuration and the arrangement of multiple systems adjacent to a reactor and in the same elastomeric layer (a "double radiator" configuration).

d) Chemically Promoted Mixing (Self-Stirring Reaction)

Mixing is chemically promoted when a reaction causes turbulence or otherwise results in movement of solutions. For example, in the [$^{18}$F]FDG synthesis described elsewhere herein, mixing of [$^{18}$F]FTAG solution with HCl in Reaction step II is "chemically promoted" by having the two solutions engage in a vigorous acid-base reaction at the interface. This produces swirling, which in turn rapidly mixes the two solutions. This type of mixing mechanism involves no additional features in the device, but relies on the choices of reactants and reaction steps. Note that in the [$^{18}$F]FDG synthesis, mixing of two solutions is only needed in the hydrolysis step, because in all other steps when a reagent solution is introduced into the reaction chamber, all other reagents are already distributed throughout the chamber in the solid form. As noted elsewhere, if the FTAG solution is evaporated to dryness, it is difficult to resolubilize.

e) Vacuum-Compression Mixing

In a coin shape reactor (for example) made from elastomeric material, the walls of the reactor chamber can collapse inward under certain circumstances. For example, in the [$^{18}$F] FDG synthesis, as the acetonitrile is evaporated from the FTAG solution in a closed reaction chamber, the coin-shape of the latter allows its flat surfaces to cave in as the volume of the solution is reduced (and a vacuum is created inside the chamber). When the valve on the acid channel is opened, the elastomer restores its shape and volume of the chamber by pulling the acid inside rapidly. The speed of such introduction of the second solution promotes virtually instantaneous mixing.

f) Expansion Mixing

Another mixing mechanism, suitable for elastomeric and similar devices takes advantage of the elasticity of the material from which the chip is fabricated. Such mixing starts by having the reactor half-full with a solution of one reagent. Subsequent introduction the second reagent fills the empty half of the chamber. In order to "stir" the reaction, the pressure can be pulsed in the flow channel used for the introduction of the second reagent (while the valve on that channel is open). The elastic chamber will expand and return to its shape at the frequency of pulsing. The contents of the chamber will then move out of the chamber and back in rapidly resulting in rapid and complete mixing followed by closing the corresponding valve on the channel used.

g) Mixing by Introduction

The spatial relationship between flow channels (such as distribution manifolds) and reactors can be selected to accelerate mixing or fluid movement within an isolated microfluidic environment. For example, the use of a distribution manifold for simultaneous introduction of a solution into the chamber can result in efficient mixing.

i) Other Mixing Methods

The mixing methods above are provided as examples, and not for limitation. A variety of other methods for mixing will be apparent to the practitioner upon review of this disclosure.

Sequential Reactions

The device of the invention is particularly suited for carrying out sequential reactions (in which a product of a first reaction is a reactant in a subsequent reaction). Thus, for example, the invention provides a method for carrying out sequential chemical reactions providing a microfluidic device comprising a reactor, providing reagents sufficient for carrying out at least two sequential chemical reactions, carrying out a first chemical reaction in the reactor, thereby producing a first reaction product; and carrying out a subsequent chemical reaction in the reactor, where the first reaction product is a reactant in the second chemical reaction and where the first reaction product is not removed from the reactor prior to the second reaction. In a related embodiment the first reaction product is a catalyst in a subsequent reaction. In one embodiment of the invention the two reactions are carried out in different solvent systems. In one embodiment, at least a portion of the solvent system in which the first reaction occurs is removed from the reactor while retaining, optionally without removing, the first product, by evaporating the solvent system out of the fluidically isolated reactor.

In a closely related embodiment the method of carrying out sequential chemical reactions include reacting a first reactant and a second reactant in the reactor, where the first and second reactants are in solution in a reaction solvent system, where the reactor is fluidically isolated, and where a first reaction product is produced; evaporating at least a portion of the reaction solvent system from the fluidically isolated reactor; introducing into the reactor a solution containing a third reactant, while retaining, optionally without removing, the first product in the reactor. In an embodiment, the first reaction product and the third reactant react to product a new (second) reaction product. In another related embodiment the method of carrying out sequential chemical reactions include reacting a first reactant and a second reactant in the reactor, where the first and second reactants are in solution in a reaction solvent system, where the reactor is fluidically isolated, and where a first reaction product is produced; evaporating at least a portion of the reaction solvent system from the fluidically isolated reactor; introducing into the reactor a solution containing a catalyst, while retaining, optionally without removing, the first product in the reactor. In an embodiment, the first reaction product reacts with a third reactant, which is either present in the reactor or added, in a reaction catalyzed by the catalyst, to product a new (second) reaction product. In another embodiment, the first reaction product does not combine with another reactant, but is instead modified (e.g., hydrolyzed, deprotected, etc.) in the presence of the catalyst. A reaction series of this type (Reactions I and II) resulting in production of [$^{18}$F]FDG is described in the Examples, below.

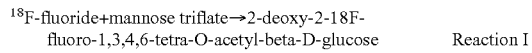

$^{18}$F-fluoride+mannose triflate→2-deoxy-2-18F-fluoro-1,3,4,6-tetra-O-acetyl-beta-D-glucose    Reaction I

2-deoxy-2-18F-fluoro-1,3,4,6-tetra-O-acetyl-beta-D-glucose+HCl→$^{18}$F-2DG    Reaction II As described, Reaction I was carried out in a reactor in acetonitrile (the reaction solvent system). At the completion of Reaction I, the acetonitrile was removed from the fluidically isolated reactor by evaporation through the PDMS wall. An aqueous solution containing HCl was introduced into the chamber and the [$^{18}$F]FDG product generated in Reaction II. In this reaction HCl acts as a catalyst. Catalysts that may be used in reactions include heterogeneous catalysts (present in different phases from the reactants, e.g. a solid catalyst in a liquid reaction mixture) and homogenous catalysts (present in the same phase, e.g. dissolved catalyst in a liquid reaction mixture). In an embodiment the catalyst is an acid.

It will be appreciated that, if desired, additional reactions can be carried out in sequence by repeating rounds of reaction, solvent modification or removal, and addition of reagents such as reactants, catalysts or reaction initiators. In one embodiment, three sequential reactions are carried out, such as:

$R1+R2 \rightarrow P1$    1.

$P1+R3 \rightarrow P2$    2.

$P2+R4 \rightarrow P3$    3.

where R1-4 are reactants and P1-3 are reaction products (P1-2 are also reactants). Solvent exchange or modification can take place, for example, between Steps 1 and 2 and between Steps 2 and 3. In some embodiments, parallel reactions (i.e., generation of more than one product in the reactor) take place, e.g.,

$R1+R2 \rightarrow P1; R3+R4 \rightarrow P2$    1.

$P1+P2+\text{catalyst} \rightarrow P3$    2.

with a solvent exchange or modification between Steps 1 and 2. In other embodiments multicomponent or combinatorial reactions are carried out. For example, and not limitation, exemplary reactions that can be carried out in the device of the invention are described below.

Although it is convenient to carry out sequential reactions in the same chamber, sequential reactions using the methods of the invention can also be carried out by conducting a first reaction in a first reactor in a first solvent, transporting the product of the reaction to a second reactor and conducting a second reaction in the second reactor in a second solvent, with solvent exchange occurring in either the first or second reactors.

In another scheme, two or more sequential reactions can be carried out in a first reactor in which solvent exchange occurs and the product then transported out of the reactor and modified, and the "modified product" transported to a second reactor. Modifications include, for example, chemical modification, concentration (e.g., by column chromatography), mixing with other agents (e.g., in a rotary mixer), heating, and various other modifications that will be apparent to the ordinarily skilled chemist.

A wide variety of chemical processes may be integrated into the microfluidic devices of the present invention and adapted for sequential synthetic processes on the nanogram scale. Examples include, for illustration, oxidation, reduction, esterification, hydrolysis, substitution, Suzuki couplings, Kumada couplings, nitrations, diazo couplings, diazotizations, photocyanations, dehydration reactions, esterifications, fluorinations, hydrolysis reactions, Grubbs metathesis, Kumada-Corriu coupling, aldol reactions, and oxidations. See *Current Opinion in Chemical Biology* 7:380-387 (2003), and de Mello et al., 2002 *Lab Chip,* 2:7N-13N. In one embodiment the chemical reaction is a substitution reaction. In one embodiment the substitution is a fluorination reaction.

Additional specific examples include of peptide syntheses, the synthesis of a series of 2-aminothiazoles using a Hantzsch synthesis, the synthesis of cycloadducts in a condensation of an aldehyde with an EDDA catalyst, Swern oxidation, and labeling of carboxylic esters with a short-lived positron-emitter (e.g., carbon-11 or fluorine-18), and oxidative dehydrogenation of alcohols. See *Current Opinion in Chemical Biology* 7:380-387 (2003), Kawaguchi et al., 2005, *Angew. Chem. Int. Ed.*, 44:2413-16, and Lu et al., 2004, *Lab Chip* 4: 523-25; de Mello et al., 2002, *Lab Chip*, 2:7N-13N.

In one embodiment, the reaction is carried out in the presence of a cryptand. For illustration and not limitation exemplary cryptands include Kryptofix 5; Kryptofix 21; Kryptofix 22; Kryptofix 22 aza trisulfate; Kryptofix 22 DD; Kryptofix 22 polymer; Kryptofix 23; Kryptofix 111; Kryptofix 211; Kryptofix 221; Kryptofix 221 B polymer; Kryptofix 222; Kryptofix 222 B; Kryptofix 222 BB; Kryptofix 222 B polymer; Kryptofix 222 CC; Kryptofix 222 D; Crown ether/12-Crown-4; Crown ether/15-Crown-5; 811684 Crown ether/18-Crown-6; Crown ether/4'-Nitrobenzo-15-crown-5; Crown ether/Decyl-18-crown-6; Crown ether/Dicyclohexyl-18-crown-6; Crown ether/N-Phenylaza-15-crown-5. All of these are commercially available (Merck KGaA). In one embodiment the cryptand is Kryptofix 222 [4,7,13,16,21,24-Hexaoxa-1,10-diazabicyclo[8.8.8]hexacosane].

These reactions may be adapted to sequential syntheses performed in the microfluidic device of the present invention. The compounds generated by such reactions can be composed of any components that can be joined to one another through chemical bonds in a series of steps. Thus, the components can be any class of monomer useful in combinatorial synthesis. Hence, the components, monomers, or building blocks can include, but are not limited to, amino acids, carbohydrates, lipids, phospholipids, carbamates, sulfones, sulfoxides, esters, nucleosides, heterocyclic molecules, amines, carboxylic acids, aldehydes, ketones, isocyanates, isothiocyanates, thiols, alkyl halides, phenolic molecules, boronic acids, stannanes, alkyl or aryl lithium molecules, Grignard reagents, alkenes, alkynes, dienes and urea derivatives.

Given the diversity of components that can be utilized in the methods of the invention, the compounds capable of being formed are equally diverse. Essentially molecules of any type that can be formed in multiple cycles in which the ultimate compound or product, is formed in a component by component fashion can be synthesized according to the methods of the invention. Examples of compounds that can be synthesized include but are not limited to molecular imaging agents, benzodiazepines, thiazolidinones, and imidizolidinones. The final compounds can be linear, branched, cyclic or assume other conformations. The compounds can be designed to have potential biological activity or non-biological activity.

In one aspect, the invention provides a method for radiolabeling a compound. Sequential radiolabeling processes that can be carried out on a automated integrated microfluidic CRC include, for example, one or more of the following: (i) concentration or pre-treatment of radioactive reagent or precursor, (ii) mixing and reacting of radiolabeling reagent with the precursor to produce radiolabeled intermediate, (iii) deprotection or chemical modification of the radiolabeled intermediate, (iv) purification of radiolabeled product which is the desired molecular probes and (v) quality analysis and control.

In one aspect, the invention provides a method for synthesizing a radiolabeled product in a microfluidic environment by mixing and reacting of a radiolabled reactant with a precursor reactant compound to produce a radiolabeled product, where the mixing and reacting occurs in a microfluidic reactor and where the radiolabled reagent is introduced into the reactor in a first solvent and the radiolabeled precursor is introduced in a second solvent that is different from the first. In some embodiments, the radiolabeled product is a radiolabeled molecular imaging probe. In some embodiments the radiolabeled molecular imaging probe is 2-deoxy-2-[$^{18}$F] fluoro-D-glucose ([$^{18}$F]FDG); 6-[$^{18}$F]fluoro-L-3,4-dihydroxyphenylalanine ([$^{18}$F]FDOPA); 6-[$^{18}$F]fluoro-L-meta-tyrosine ([$^{18}$F]FMT), 9-[4-[$^{18}$F]fluoro-3-(hydroxymethyl)butyl]guanine ([$^{18}$F]FHBG), 9-[(3-[$^{18}$F]fluoro-1-hydroxy-2-propoxy)methyl]guanine ([$^{18}$F]FHPG), 3-(2'-[$^{18}$F]fluoroethyl)spiperone([$^{18}$F]FESP), 3'-deoxy-3'-[$^{18}$F]fluorothymidine ([$^{18}$F]FLT), 4-[$^{18}$F]fluoro-N-[2-[1-(2-methoxyphenyl)-1-piperazinyl]ethyl]-N-2-pyr-idinyl-benzamide([$^{18}$F]p-MPPF), 2-(1-{6-[(2-[$^{18}$F]fluoroethyl)(met-hyl)amino]-2-naphthyl}ethylidine)malononitrile ([$^{18}$F]FDDNP), 2-[$^{18}$F]fluoro-alpha-methyltyrosine, [$^{18}$F]fluoromisonidazole([$^{18}$F]FMISO), 5-[$^{18}$F]fluoro-2'-deoxyuridine([$^{18}$F]FdUrd), [$^{11}$C]raclopride, [$^{11}$C]N-methylspiperone, [$^{11}$C]cocaine, [$^{11}$C]nomifensine, [$^{11}$C]deprenyl, [$^{11}$C]clozapine, [$^{11}$C]methionine, [11C]choline, [$^{11}$C]thymidine, [$^{11}$C]flumazenil, [$^{11}$C]alpha-aminoisobutyric acid or a protected form of one of the foregoing compounds. In particular embodiments the radiolabeled reactant is [$^{18}$F]-potassium fluoride and the precursor reactant is 2-(1-{6-[(2-(p-toluenesulfonyloxy)ethyl)(methyl)amino]-2-napthyl}ethylidine)malononitrile or is D-mannose triflate. Table 1 shows, for example and not for limitation, exemplary PET imaging agents and exemplary precursors. It will be appreciated that multiple synthetic routes can be used for synthesis of such agents.

TABLE 1

| precursor(s) | product |
|---|---|
| D-mannose triflate. | [$^{18}$F]FDG |
| 2-(1-{6-[(2-[(p-toluenesulfonyl-oxy)ethyl)(methyl)amino]-2-naphthyl}ethylidine)malononitrile, | [$^{18}$F]FDDNP |
| N-Boc-5'-O-dimethoxytrityl-3'-O-(4-nitrophenylsulfonyl)-thymidine | [$^{18}$F]FLT |
| N$^2$-(p-anisyldiphenylmethyl)-9-[(4-p-toluenes-ulfonyloxy)-3-(p-anisyldiphenylmethoxy-methyl)butyl]guanine | [$^{18}$F]FHBG |
| N$^2$-(p-anisyldiphenylmethyl)-9-[[1-[(.beta.-anisy-ldiphenylmethoxy)-3-(p-toluenesulfonyloxy)-2-propoxy]methyl]guanine | [$^{18}$F]FHPG |
| 8-[4-(4-fluorophenyl)-4,4-(ethylenedioxy)bu-tyl]-3-[2'-(2,4,6-trimethylphenylsulfonyloxyethyl)]-1-phenyl-1,3,8-triazas-piro[4.5]decan-4-one | [$^{18}$F]FESP |
| 5'-O-Boc-2,3'anhydrothymidine | [$^{18}$F]FLT |
| N-[2-[4-(2-methoxyphenyl)-1-piperazinyl]ethy-1]-4-nitro-N-2-pyridinyl-benzamide | p-[$^{18}$F]MPPF |
| 1,2-bis(tosyloxy)ethane and N,N-dimethylethanolamine | [$^{18}$F]fluoroethylcholine; |
| Ditosylmethane and N,N-dimethylethanolamine | [$^{18}$F]fluorocholine |

Methods for synthesis of these compounds are well known and can be easily adapted to use in the microfluidic systems of the invention (see, e.g., Hamacher et al., 1986, "Efficient Stereospecific Synthesis of No-Carrier-Added 2-[F-18]-Fluoro-2-Deoxy-D-Glucose Using Aminopolyether Supported Nucleophilic-Substitution" *Journal of Nuclear Medi-* cine 27:235-238; Padgett et al., 1989, "Computer-Controlled Radiochemical Synthesis—a Chemistry Process-Control Unit for the Automated Production of Radiochemicals" *Applied Radiation and Isotopes* 40:433; Machulla et al., 2000, "Simplified labeling approach for synthesizing 3'-deoxy-3'-[F-18]fluorothymidine ([F-18]FLT)" *Journal of Radionalytical and Nuclear Chemistry* 243:843-46; Shoghi-Jadid. et al., 2002, "Localization of neurofibrillary tangles and beta-amyloid plaques in the brains of living patients with Alzheimer disease" *American Journal of Geriatric Psychiatry* 10:24-35).

The skilled artisan will immediately appreciate that the invention could be readily adapted for synthesis of any appropriate radioactive compound comprising a radionuclide, including radiochemicals useful in other imaging systems. Radionuclides that may be used include, but are not limited to, positron emitting radionuclides such as $^{11}C(t_{1/2}=20.1$ min), $^{18}(t_{1/2}=110$ min), $^{124}I$ ($t^{1/2}=4.2$ days), $^{13}N$ ($t_{1/2}=19.3$ min) and $^{15}O$ ($t_{1/2}=2.03$ min) and other suitable radionuclides, e.g., $^{52}Fe$ ($t_{1/2}=8.3$ hr), $^{55}(t_{1/2}=17.5$ hr), $^{55}Co$ ($t_{1/2}=9.7$ min), $^{75}Br(t_{1/2}=98$ min), $^{76}Br$ ($t^{1/2}=16.1$ hr) and $^{94}Tc$ $^{111}In=53$ min) can be introduced into molecules to serve as molecular probes for PET. Similarly, the integrated microfluidic CRCs can be applied for introducing gamma emitters such as $^{99}Tc$, $^{111}In$, $^{67}Ga$, $^{123}I$ and $^{125}I$ and beta emitters such as $^{14}C$ and $^{32}P$ into the respective molecular probes.

For example, in some embodiments, the present invention is directed to highly efficient incorporations of [$^{11}C$]-containing molecules, for example, [$^{11}C$]methane, [$^{11}C$]carbon dioxide, [$^{11}C$]carbon monoxide, [$^{11}C$]-containing halides ([$^{11}C$]-RX), [$^{11}C$]-containing acid chloride (R[$^{11}C$]COX), ($^{11}C$]-containing carboxylic acids (R[$^{11}C$]COOH), [$^{11}C$]-containing; ester (R[$^{11}C$]COOR), [$^{11}C$]-containing alcohols (R[$^{11}C$]COH), [$^{11}C$]CN, [$^{11}C$]CCI4, [$^{11}C$]phosgene and, [$^{11}C$]urea into, e.g., PET molecular probes. In some embodiments, the present invention is directed to highly efficient synthesis of [$^{124}I$]-labeled PET molecular probes.

Generally, a radioactive isotope is reacted in an appropriate solvent, such as polar aprotic solvents, such as acetonitrile, acetone, 1,4-dioxane, tetrahydrofuran (THF), tetramethylenesulfone (sulfolane), N-methylpyrrolidinone (NMP), dimethoxyethane (DME), dimethylacetamide (DMA), N,N-dimethylformamide (DMF), dimethylsulfoxide (DMSO), and hexamethylphosphoramide (HMPA). For solutions containing $^{18}F$, the radioactive isotope is typically in the form of a coordination compound including a phase transfer catalyst and salt complex. One common $^{18}F$ solution includes Kryptofix 2.2.2 as the phase transfer catalyst and $^{18}F$ in a salt complex with potassium carbonate ($K_2CO_3$).

In some embodiments, the radiochemical synthesis reaction used in the invention comprises the additional step of deprotecting the radiochemical following reaction with the radioactive isotope. Typically, the deprotecting step is a hydrolysis reaction that includes contacting and reacting the radiochemical with a hydrolyzing agent, such as an aqueous base solution or an aqueous acid solution. The aqueous base solution may be an alkali metal hydroxide (e.g., sodium hydroxide or potassium hydroxide) and the aqueous acid solution may include hydrochloric acid.

In some embodiments, for radionuclide labeling processes, a number sequential steps may be performed within the microfluidic device. For clarity, synthesis steps are set forth below using the [$^{18}F$]fluoride ion, but are equally applicable to other radionuclides using modifications apparent to those skilled in the art. It will be appreciated that not all of these steps are required for each synthesis (e.g., intermediate and post-synthetic purification steps may be omitted) and not all of the steps recited are carried out on the microfluidic system or device of the invention. These steps may include: receiving aqueous [$^{18}F$]fluoride ion from the cyclotron target; separating the [$^{18}F$]fluoride ion from the water and collecting the water; generating a solution of reactive [$^{18}F$]fluoride ion in an organic and/or polar aprotic solvent (acetonitrile, DMF, DMSO, etc.); providing a solution of a reactive precursor in an organic and/or polar aprotic solvent (acetonitrile, DMF, DMSO, etc.); reacting the [$^{18}F$]fluoride ion with the precursor using a nucleophilic substitution reaction to create a new carbon-fluorine bond, using heat if necessary; purifying the initial [$^{18}F$]fluorinated product by solid phase extraction or chromatography; reacting the purified initial [$^{18}F$]fluorinated product with a second reagent to generate the final [$^{18}F$]fluorinated product (e.g., hydrolysis of protecting group(s), if necessary); purifying the final [$^{18}F$]fluorinated product by, for example, solid phase extraction or chromatography; desolvating the [$^{18}F$]fluorinated product; assaying the purified final [$^{18}F$]fluorinated product for radioactivity, UV absorbance, and conductivity/pH; delivering the purified final [$^{18}F$] fluorinated product; and/or dispensing the purified final [18F] fluorinated product Multicomponent Reactions In addition to the introduction into the reactor of two solutions each containing a single reactant, it is contemplated that a number of other types of reactions will be carried out.

In one embodiment, the first and second reactants are introduced into the reactor as single solution containing both reactants in a first solvent system, and a catalyst of the reaction is added in second solvent system. After the introduction of the reactants and catalyst, the reactor is fluidically isolated.

In another embodiment, the first and second reactants are introduced into the reactor as single solution containing both reactants in a first solvent system, and a compound that is neither a catalyst nor a reactant, but which affects the environment of the reactor (e.g., causes a change in pH) in a way that initiates or accelerates the reaction between the first and second reactants is added. After the introduction of the reactants and compound, the reactor is fluidically isolated.

In a third embodiment, the product is generated in a multicomponent reaction and multiple reactants are introduced into the reactor. Multicomponent reactions are convergent reactions, in which three or more starting materials react to form a product, according to a cascade of elementary chemical reactions. See, A. Dömling in: Multicomponent Reactions (J. Zhu, H. Bienayme) Wiley-VCH, Weinheim 2005, p. 76; A. Doemling, *Org. Chem. Highlights* 2005, Apr. 5. URL: http://www.organic-chemistry.org/Highlights/2005/05April.shtm; Kolb et al., 2002 *Tetrahedron Lett.* 43:6897; Fayol et al., 2005, *Org. Lett.* 7:239). Usually the multiple reagents are introduced individually (i.e., different reactants do not enter the reactor through the same port at the same time) but reagents can also be introduced in various combinations.

In a fourth, related embodiment, a product is generated by a series of reactions that generate intermediate products, e.g.:

where A, B, C and D are reactants introduced into the reactor, and X, Y and P are produced in the reactor under reaction conditions.

Combinatorial and Parallel Syntheses

It will be apparent from this disclosure that chemical reaction circuits can be used to in combinatorial chemical syntheses. For example, the products of a first series of reactions (in reactors A, B, C, and D) can be transported in various combinations (e.g., AA, AB, AC, AD, BC, BD, CD) to second reactors for combinatorial synthesis. It will be apparent from this disclosure that chemical reaction circuits can be run in parallel on the same chip. Up to several hundreds of thousands CRCs can be placed on a single chip so that multiple sequential chemical processes can be run in parallel.

Removing Product or Reagents from a Reactor

Figure 8A:
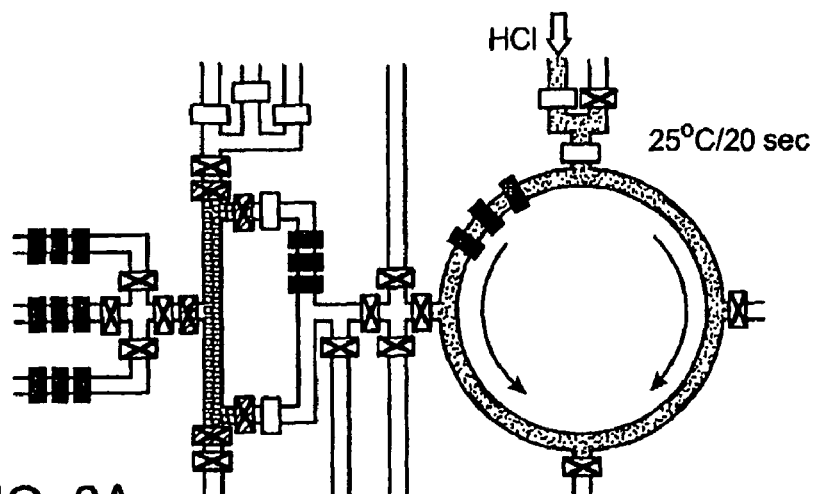
FIG. 8. Schematic diagrams summarize the hydrolytic process which is composed of 3-steps sequential operations in the CRC. (A) HCl aqueous solution (3.0 N) was introduced from the top right channel (in light blue) to the reaction loop by dead-end filling. This step took 20 seconds at 25° C. (B) The HCl and the fluorinated intermediate 2a (or 2b) were mixed by the circulating pump for 1 minute at 60° C. In this step, the intermediate 2 (or 2b) was hydrolyzed to yield the final product FDG (3a,b). (C) The solution containing FDG (3a,b) (in dark blue) was flushed out of the device though the product line located at the bottom of the CRC.
Figure 8B:
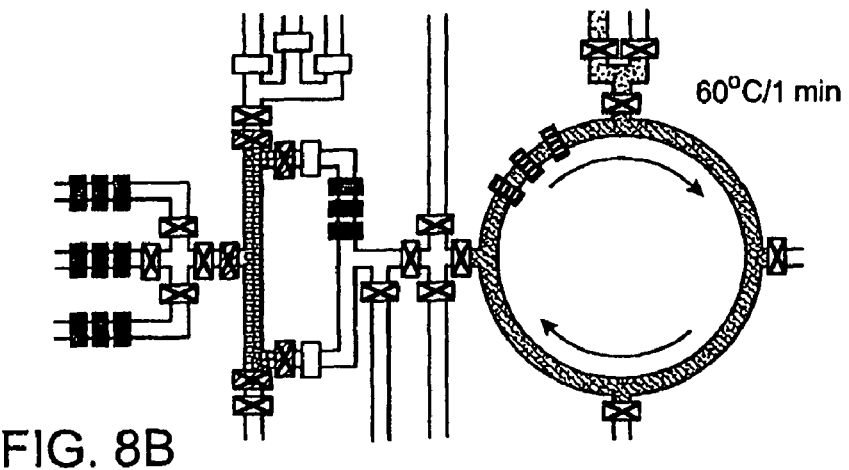
Figure 8C:
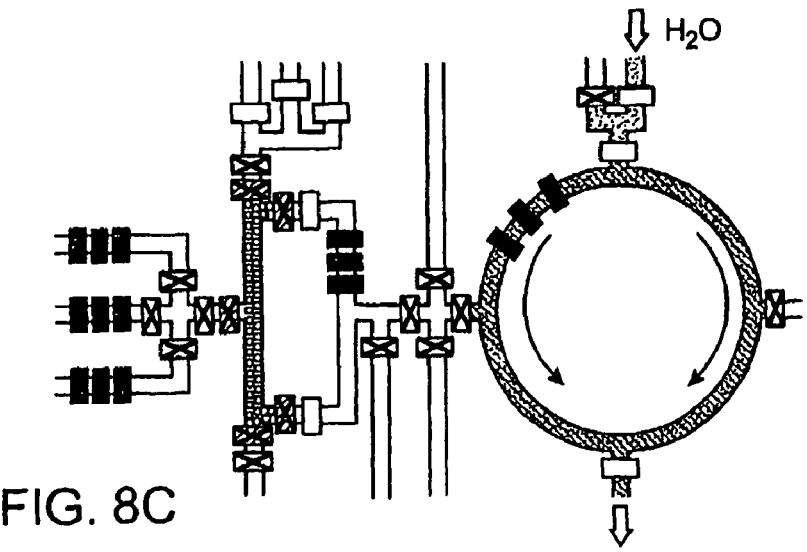

A reaction product can be removed from a reactor by flushing the reaction with a solvent (such as water). For example, as illustrated in FIG. 8C and corresponding text, solvent (e.g., water) can be flowed into a reactor to flush the product out through an open valve into a flow channel to a reservoir or other component of the system.

Figure 13:
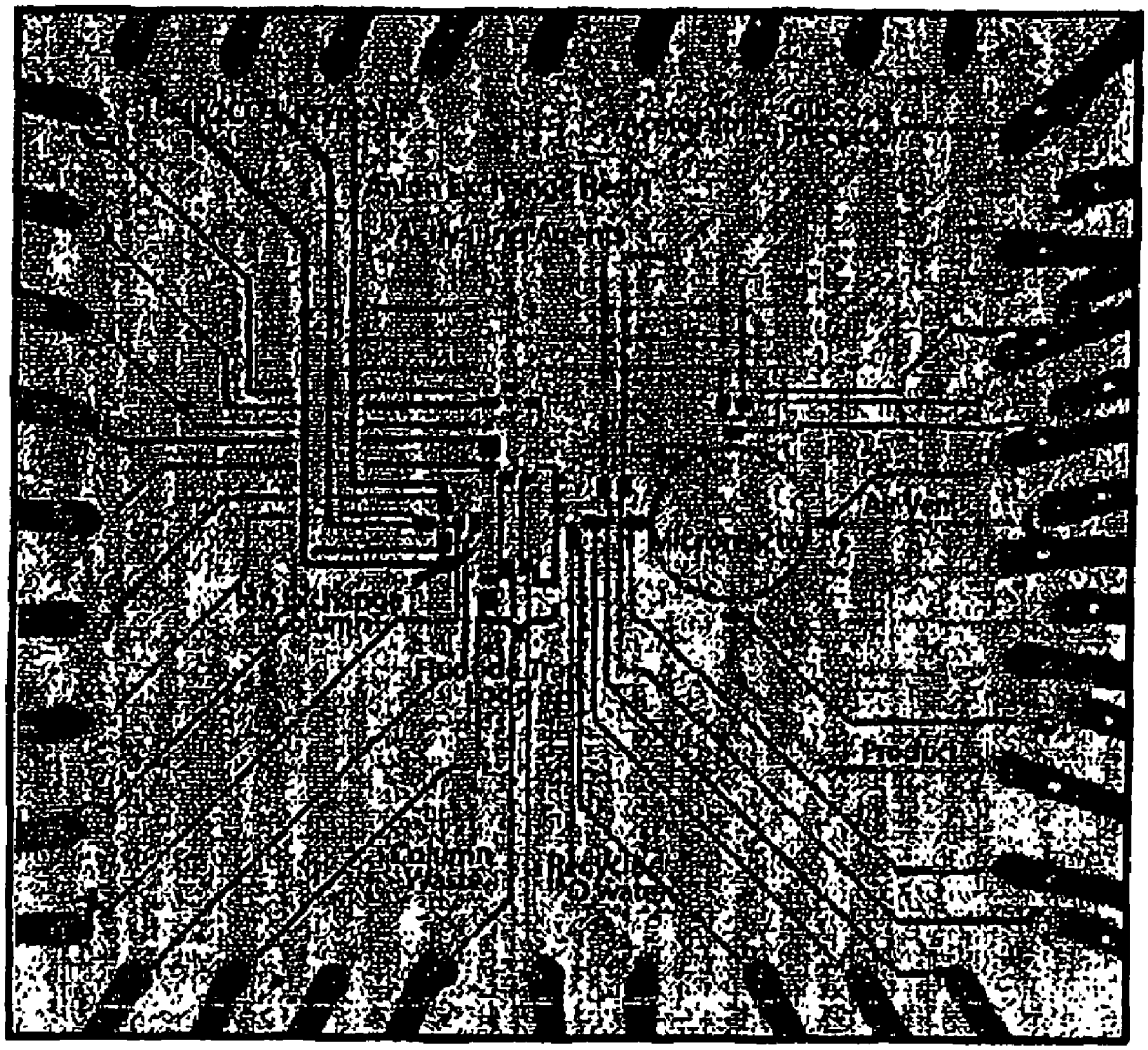
FIG. 13 shows an optical micrograph of a PDMS-based integrated CRC, which is intentionally filled with different dyes in order to better distinguish different modules in the device. The red and yellow lines signify the control channels associated with valve and pump modules, respectively. Both of the control lines are connected with gas manifolds and driven by gas pressures ranging between 5 and 30 psi. The blue and green lines indicate fluidic channels in which solutions containing starting materials and reagents are transferred and stored. At the intersections of control (red and yellow) and fluidic (blue and green) channels, valve and pump modules are located. The deflection of individual valve membrane is utilized to impede fluid flow. Three parallel-oriented valves (yellow) can be grouped to form a peristaltic pump module that is employed to control both the direction and rate of the flow in the corresponding fluidic channels by varying the pump sequence and period.

The spatial relationship between flow channels (such as distribution manifolds) and reactors can be selected to accelerate or direct fluid movement within an isolated microfluidic environment. For example, curved inlet and outlet channels for the elution of product from the reaction chamber. See, for example, FIG. 13 which shows arrangement of a fluid inlet and outlet facilitate efficient removal of [$^{18}$F]FDG from a reactor. The tangential inlet and outlet allow the water trajectory to follow along the far wall of the reaction chamber ensuring complete product elution. When the eluent solution enters and leaves the chamber through channels perpendicular to the tangent a product may be left behind, or a significant amount of solvent is required to wash it out of the reactor. With the curved inlet and outlet the solution follows a trajectory along the far wall of the reaction chamber and allows collection of product in a small volume of solvent. In addition, making the exit channel slightly narrower than the inlet allows buildup of back pressure inside the chamber during elution, which also increases the efficiency of product collection.

Thus, one way to collect product from a coin-shaped (for example) reaction chamber is by flushing the product out through the tangential exit channel by introducing solvent (e.g., water) into the reactor through another tangential channel, which allows the flow to follow the trajectory along the far wall of the chamber. Although 1-3 reactor volumes of water seem enough (experimentally) for complete collection of product, larger elution volumes may be used, especially if larger volumes facilitate off-chip manipulations.

In an alternative approach a reactor having a radiator such as is shown in FIG. 20 and described above is drained in a two-step process: First, closing off the exit from the radiator will send $N_2$ pressure into the reactor through the gas permeable membrane. This pressure should force the product out of the reaction chamber into the only open exit channel. If at the same time the mixer depicted in FIG. 20 is activated, this should aid in directing the product solution into the exit channel and out of the reactor leaving behind at most droplets (rather than regions) of product solution. The second step should collect those droplets of residual product by filling the reactor with solvent (e.g., water) and forcing it.

Synthetic Method Comprising Column

In one aspect, the invention provides a method for carrying out a chemical reaction in an integrated microfluidic device using a microfluidic separation column, as described above. In one embodiment, the method includes introducing a solution containing a first reactant into the separation column, and adsorbing the first reactant to the stationary phase of the column, eluting the first reactant from the stationary phase, and introducing the first reactant into a reactor. In an embodiment, a second reactant is introduced into the reactor before, after, or simultaneously with the first reactant. In an embodiment, the method includes maintaining the reactor for a time and under conditions sufficient for the first reagent and the second reagent to react and produce a first reaction product.

The reactant is first bound to the stationary phase of the column in a binding step and then eluted from the stationary phase of the column in an elution step prior to being introduced into the reactor. In one embodiment, the microfluidic device includes a closed flow path defined by the separation column and one or more flow channel(s) and the binding step includes circulating a solution comprising the first or second reactant through the column at least twice. In one embodiment, the wherein said microfluidic device includes a closed flow path defined by the separation column and one or more flow channel(s) and the eluting step includes circulating an elution solution through the column at least twice.

Section 5: Exemplary Devices

As will be clear from the discussion above, the invention provides a large variety of microfluidic devices useful for solvent exchange and/or carrying out a chemical reaction or sequential reactions and/or carrying out other processes. Any number of combinations and arrangements of the components described herein are encompassed and the practitioner guided by this disclosure will be able to design and produce devices.

For illustration and not limitation, one exemplary microfluidic device includes a reactor (as defined above) that does not form a closed path and has a liquid capacity of from 5 microliter to 10 microliters.

For illustration and not limitation, one exemplary microfluidic device includes a separation column with an immobile phase through which a fluid can pass, said column having an inlet and an outlet; and one or more flow channel(s) not comprising the solid phase; where the flow channel(s) and separation column define a closed path. In one embodiment, the device has a peristaltic pump capable of moving fluid through the closed path. In one embodiment the device includes a reactor configured to be in fluidic communication with one or more flow channels. In one embodiment, the microfluidic device has a closed flow path defined by the separation column and one or more flow channel(s).

For illustration and not limitation, one exemplary microfluidic device contains vent channels. In one embodiment, an exemplary microfluidic system of the invention includes a device containing vent channels and (i) a means to flow gas (e.g., air, nitrogen, argon, etc.) through the vent channels or (ii) a vacuum pump or other means for applying a vacuum that is connected to a vent channel system of a device. In one embodiment, the In one embodiment, an exemplary device contains from 1 to 5 reactors. In one embodiment, an exemplary device includes parallel paths that simultaneously produce multiple batches of the same or different compounds.

In one aspect, a device of the invention is sterilized (e.g., by heat, toxic vapor, or irradiation). In one embodiment, the device is provided in a sterilized, aseptic form and packaged to maintain sterility until use.

In one aspect, the invention provides a microfluidic device capable of synthesizing $^{18}$F-FDG from precursors in 16 minutes or less, optionally 5:50 minutes or less.

In one aspect, the invention provides a device comprising a flow channel and sieve valves. In one aspect, the invention provides a device comprising a flow channel and at least a pair of sieve valves, with a chromatographic stationary phase material (e.g., beads or resin) is disposed in the channel between the sieve valves, and where the size of the chromatographic stationary phase material is of a size that is retained by the sieve valve. In some embodiments, the device also includes a reactor, as described herein.

Section 6: Examples

Example 1

Synthesis of [$^{19}$F]FDG

The molecular imaging probe 2-deoxy-2-[$^{18}$F]fluoro-D-glucose ([$^{18}$F]FDG) is a widely used radiopharmaceutical with over a million patient doses produced in 2004 for use in positron emission tomography (PET) imaging studies. The short half-life of [$^{18}$F]fluorine makes rapid synthesis of doses essential, and the synthetic process includes common steps required in many chemical syntheses, including the preparation of other radiolabeled molecular imaging probes. The nanogram mass of PET molecular imaging probes administered to subjects is ideal for miniaturized architecture of integrated microfluidics. Thus, the multi-step synthesis of [$^{18}$F]FDG (see Hamacher et al., 1986, *J. Nuclear Medicine* 27:235) and other PET probes represents an interesting opportunity for integrated microfluidics chips.

The synthesis of [$^{18}$F]FDG (3a) is based on 5 sequential chemical processes (FIG. 2A): (i) concentration of the dilute [$^{18}$F]fluoride solution (1-10 ppm) obtained from the proton bombardment of [$^{18}$O]water with a cyclotron; (ii) solvent exchange from water to dry acetonitrile; (iii) [$^{18}$F]fluoride substitution of the D-mannose triflate precursor 1 in dry acetonitrile; (iv) solvent exchange back to water; and (v) acidic hydrolysis of the fluorinated intermediate 2a to obtain [$^{18}$F]FDG (3a). Presently, [$^{18}$F]FDG (3a) is routinely produced in about 50 min using commercial synthesizers (Padgett et al., 1989, *Applied Radiation and Isotopes* 40:433). These automated synthesizers have a physical size of approximately 80×60×40 cm, and can produce ~10 to 100 doses in a single run. Inevitably, a considerable decrease in the radiochemical yield of the resulting probe must be tolerated because of the relatively short half-life of [$^{18}$F]fluorine ($t_{1/2}$=110 min). Obtaining high yields is even more challenging for molecular imaging biomarkers labeled with other important positron emitting radioisotopes with shorter half-lives, such as $^{11}$C ($t_{1/2}$=20 min) and $^{13}$N ($t_{1/2}$=10 min).

A microfluidic chemical reaction circuit (CRC; FIG. 2) capable of executing the five chemical processes of the syntheses of both [$^{18}$F]FDG (3a) and [$^{19}$F]FDG (3b) within a nanoliter scale reaction vessel was designed and fabricated. In initial experiments, [$^{19}$F]FDG (3a) was produced on the CRC using a multiprocess synthesis. In an initial step, $^{19}$F[Fluoride] was concentrated from solution. The concentration step was developed because the concentration of [$^{18}$F]fluoride obtained from a proton-bombarded [$^{18}$O]water is usually below 1 ppm, and performing fluorination reaction at such a low [$^{18}$F]fluoride concentration is not feasible.

A miniaturized anion exchange column (FIG. 3) in the microfluidic device to concentrate the [$^{18}$F]fluoride solution to ~100 ppm was prepared. Sieve valves (FIG. 3B) were created using a square-profiled fluidic channel and a control membrane. Actuation of this membrane prohibits the passage of large particles while still permitting the solution to pass through the edges of the channel. Using these sieve valves to trap anion exchange beads, the anion exchange column (FIGS. 3C and D) was obtained for the concentration.

For the first process, concentration of dilute fluoride, a 5 ppm NaF solution was loaded into the anion exchange column (FIG. 4A). The loading rate (5.0 nL/sec) was controlled using a metering pump. After the fluoride solution was loaded completely, a $K_2CO_3$ solution (0.25 M, 18 nL) was introduced to fill the rectangular loop. The circulating pump module was then turned on so that the $K_2CO_3$ solution (0.25 M, 18 nL) could loop through the column continuously to produce a concentrated KF solution. Because the fluorination (process iii) of the D-mannose triflate 1 requires anhydrous conditions, a digitally controlled hot plate was used to heat the CRC for removing water (process ii) from the concentrated KF solution (FIG. 4B). To completely extrude any remaining moisture, dry MeCN was loaded into the reaction loop and the CRC was heated again. Moisture and MeCN vapor can penetrate and escape the gas-permeable PDMS matrix. Once the CRC had cooled to room temperature, an anhydrous MeCN solution (40 nL) containing the D-mannose triflate 1 (92 ng, limiting reagent) and Kryptofix 222 (364 ng) was introduced into the ring-shaped reaction loop containing the dried KF. This heterogeneous reaction mixture was mixed inside the loop using the circulating pump. During this step (process iii), the CRC was heated (100° C. for 30 s and then 120° C. for 50 s) to yield the fluorinated intermediate 2b (FIG. 4C), as analyzed by GC-MS. This analysis indicated that the conversion yields for the fluorination process were 98%. After removing MeCN by direct evaporation, 3 N HCl solution (40 nL) was injected into the CRC and the hydrolysis (FIG. 4D, processes iv and v) of the intermediate 2b was conducted at 60° C. to obtain [$^{19}$F]FDG (3b), in >90% purity, according to GC-MS analysis. The PDMS materials were compatible (Lee et al., 2003, *Analytical Chemistry* 75:6544) with MeCN and the entire synthesis was demonstrated on multiple chips.

Example 2

Synthesis of [$^{18}$F]FDG

Figure 10:
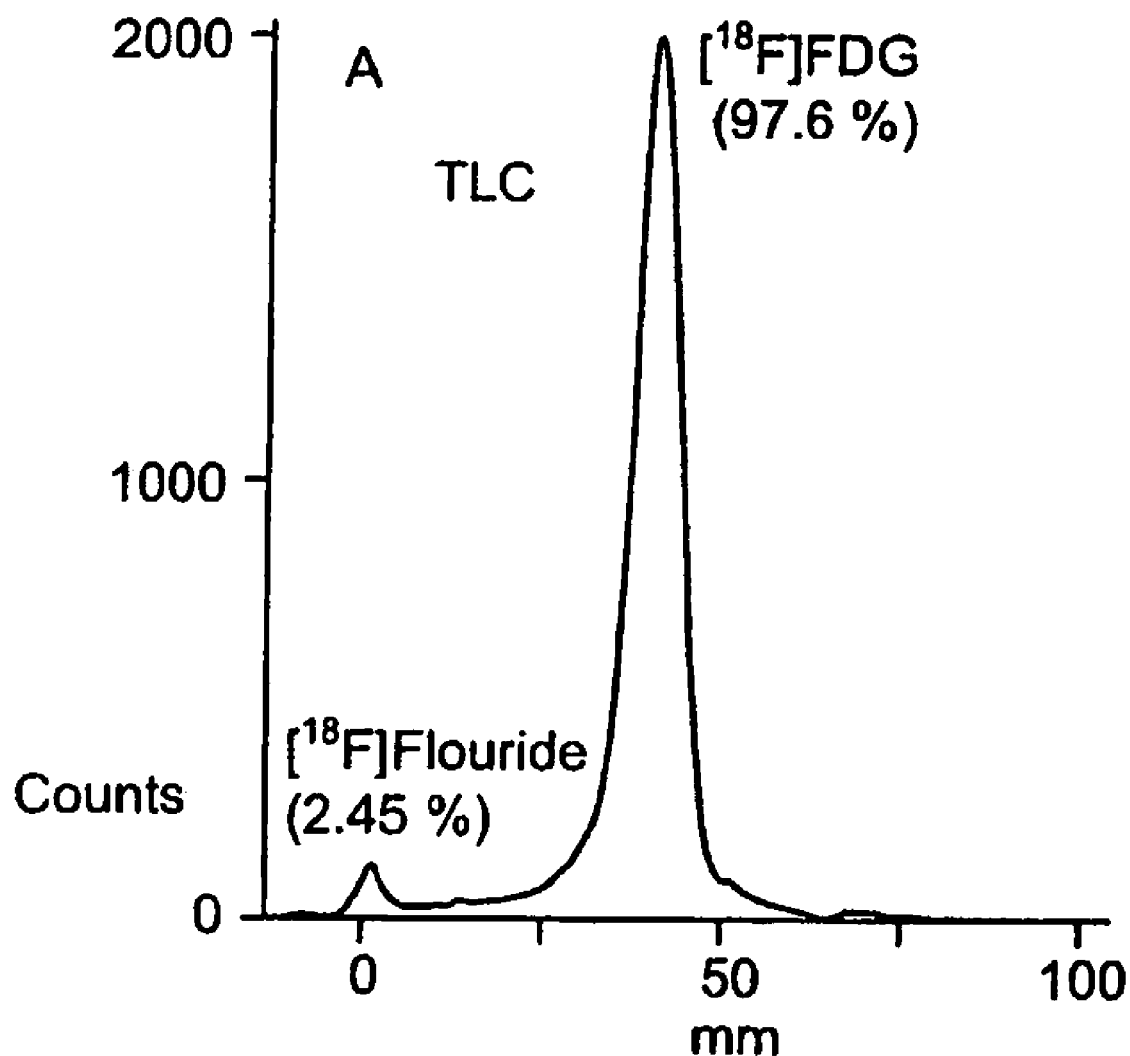
FIG. 10. Analytical TLC profile of the unpurified mixture obtained upon the sequential production of [$^{18}$F]FDG (3a) in the first generation CRC indicating that the radiochemical purity of the FDG production is up to 97.3%. The two peaks with values for $R_f$ of 0.0 and 0.4 correspond to [$^{18}$F]fluoride and [$^{18}$F]FDG (3a), respectively.

Radioactive [$^{18}$F]FDG (3a) was produced in the CRC by starting from radioactive [$^{18}$F]fluoride obtained from proton-bombarded [$^{18}$O]water. In this experiment, only 720 μCi of [$^{18}$F]fluoride (limiting reagent) in ca. 1 μL of [$^{18}$O]water was used, in an automated fashion. Because of the relative high loading rate (ca. 65 nL/sec) applied, only 500 μCi of [$^{18}$F]fluoride was trapped in the column; the subsequent chemical steps to produce [$^{18}$F]FDG (3a) were completed within 14 min to obtain 190 μCi product 3a having a radiochemical yield of 38% and a radiochemical purity of 97.6%, according to radio-TLC analysis (FIG. 10). Similar results were observed across multiple runs.

Materials and Methods

Fabrication of the first generation CRC. The chip was fabricated using multi-layer soft lithography method. (McDonald et al., 2000, *Electrophoresis* 21:27; Unger et al. 2000, *Science* 288:113.) Two different molds were first fabricated by photolithographic processes to create the fluidic channels and the control channels for actuating the values located in the respective layers of the PDMS-based CRC. The mold used to create the fluidic channels was made by a following two-step photolithographic process. In the first step, a 45-μm thick negative photoresist (SU8-2025) was spin coated on to a silicon wafer (Silicon Quest, San Jose, USA). After UV exposure and development, a square-profiled pattern for the miniaturized anion exchange column was obtained. In the next step, a second layer of 45-μm thick positive photoresist (AZ 100XT PLP) was then spin coated on the same wafer. Prior to the UV exposure the mask was aligned (Karl Suss America Inc., Waterbury, Vt.) to ensure a good match between two set of patterns of the control and fluid channels. Once the positive photoresist was developed, the wafer was heated above the glass transition temperature of the positive photoresist. As a result, the surface profile of the patterned positive photoresist was transformed into a round profile while the profile of the negative photoresist remains unchanged (square profile). This device has a channel height of 45 μm and width of 200 μm. The control channels mold was made by introducing a 25 μm-thin negative photoresist (SU8-2025) pattern on a silicon wafer. In order to achieve reliable performance of each valve, the width of the control channel was set at 250 μm in sections where the valve modules are located.

Before fabricating the device, both the fluidic and control molds were exposed to trimethylchlorosilane (TMSCl) vapor for 2-3 minutes. A well-mixed PDMS (GE, RTV 615 A and B in 5 to 1 ratio) was poured onto the fluidic mold located in a petri dish to give a 5 mm-thick fluidic layer. Another portion of PDMS (GE, RTV 615 A and B in 20:1 ratio) was spin-coated onto the control mold (1600 rpm, 60 s, ramp 15 s) to obtain the control layer. The thick fluidic layer and thin control layer were cured in an 80° C. oven for 50 minutes. After incubation, the thick fluidic layer was peeled off the mold, and holes were introduced onto the fluidic layer for access of reaction solutions. The fluidic layer was then trimmed, cleaned and aligned onto the thin control layer. After baking at 80° C. for 60 minutes, the assembled layer was peeled off the control mold, and another set of holes were punched for access of control channels. These assembled layers were then placed on top of a glass slide that was coated (1600 rpm, 60 s, ramp 15 s) with PDMS (GE RTV 615 A and B in 20:1 ratio) that had been cured for 45 minutes in the oven. The device was done after overnight incubation.

Control Interface. The pneumatic control setup consists of 4 sets of eight-channel manifolds controlled through BOB3 breakout controller board (Fluidigm, San Francisco, USA). Argon gas that was pre-dried through a gas purifier (Hammond Drierit, Xenia, USA) provides pressure (30 psi) to the manifolds. 32 Control lines from the device are individually connected to the corresponding channels on the manifolds with metal pins (23 Gauge, New England Small Pin Corp, USA) using Tygon microbore tubing (Cole-Parmer East, Bunker Court, USA). When a channel on the manifold is activated, argon gas enters the control line connected with the specific channel, providing pressure to close valves in the microfluidic device. The control interface was created using Labview program on a PC. A National Instruments card (AT-DIO-32HS) digitally controls the switching of manifolds through the BOB3 breakout controller board. The Labview program allows for manual control of individual valves and for automation of the synthesis processes.

Materials. All reagents were purchased from SIGMA-ALDRICH. Solvents purchased form VWR/EMD were purified according to literature procedure. Armarego et al., 2003, *Purification of Laboratory Chemicals* (Butterworth Heinemann, New York, ed. Fifth, 2003). GC-MS was performed with GC/EI Time-of-Flight mass spectrometer (Micromass GCT). DBS-MS capillary column (40 m long, 320 μm of OD) was employed for GC analyses of [$^{19}$F]FDG intermediate (2b) and product (3b) using Helium as carrier gas at flow rate of 1.2 mL/min. No-carrier-added [$^{18}$F]fluoride (specific activity: >10,000 Ci/mmol) was produced by 11 MeV proton bombardment of 95% $^{18}$O-enriched $H_2O$ via $^{18}O(p,n)^{18}F$ nuclear reaction using a RDS-112 cyclotron. HPLC analysis was performed using a Rainin-HP system equipped with a γ-detector. A Phenomenex column (Econosphere-$NH_2$, 5 μm, 250×4.6 mm) was used with a solvent system of 85% MeCN and 15% $H_2O$. Radio-TLC analysis was performed on silica plate (EM Separation Technology, Silica gel 60) with eluent system of 85% MeCN and 15% $H_2O$.

Preparation and Evaluation of Anion Exchange Column. Anion exchange beads (Source 15Q, Amersham Biosciences) were packed into the column module by introducing an aqueous solution containing suspended beads into the microfluidic reactor. The beads were activated by passing 1.0 M of $KHCO_3$ through the column followed by sequential introduction of DI water (18 MΩ).

Snapshots of FDG Synthesis in the CRC. The FDG (3a,b) synthesis in the CRC is based on three sequential synthetic processes starting from (i) concentration of dilute fluoride, followed by (ii) fluorine substitution reaction of the D-mannose triflate precursor 1 and (iii) acidic hydrolysis of the fluorinated intermediate 2a (or 2b). There were 15 steps to complete the FDG (3a,b) synthesis in a CRC. The details of these sequential operations using schematic diagrams shown in FIGS. 6-8.

Figure 9A:
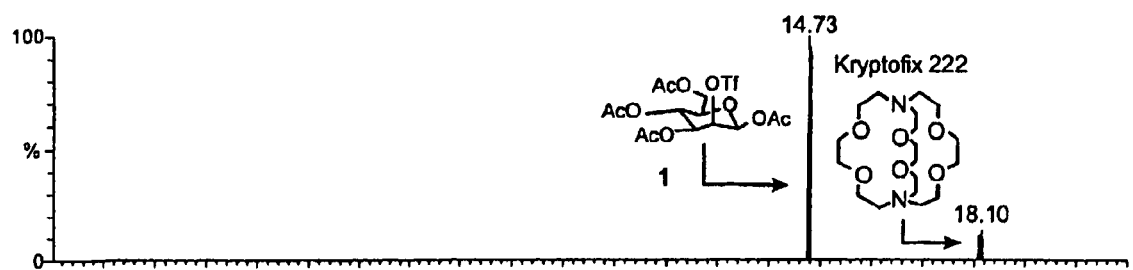
FIG. 9. (A) GC-MS plot of a mixture containing MeCN, mannose triflate 1 and Kryptofix 222. The two peaks at retention times of 14.73 and 18.10 min correspond to mannose triflate 1 and Kryptofix, respectively. (B) GC-MS plot of the mixture in (A) after its reaction with concentrated fluoride in the CRC. The peak having a retention time of 14.16 min corresponds the formation of the fluorinated intermediate 2b. A calibrated integration of the chromatogram suggests a conversion yield of 95%. (C) GC-MS plot of a TMS-functionalized [$^{19}$F]FDG (3b) which is obtained by treating crude [$^{19}$F]FDG (3b) with TMSCl. The calibrated integration indicates that the hydrolytic reaction of intermediate 2b resulted [$^{19}$F]FDG (3b) in >90% purity.
Figure 9B:
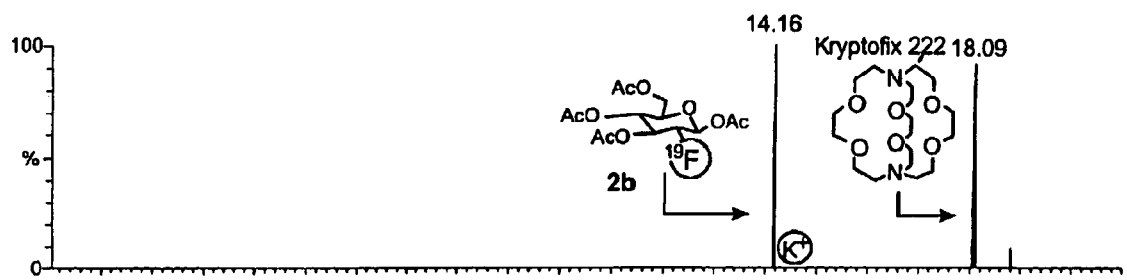
Figure 9C:
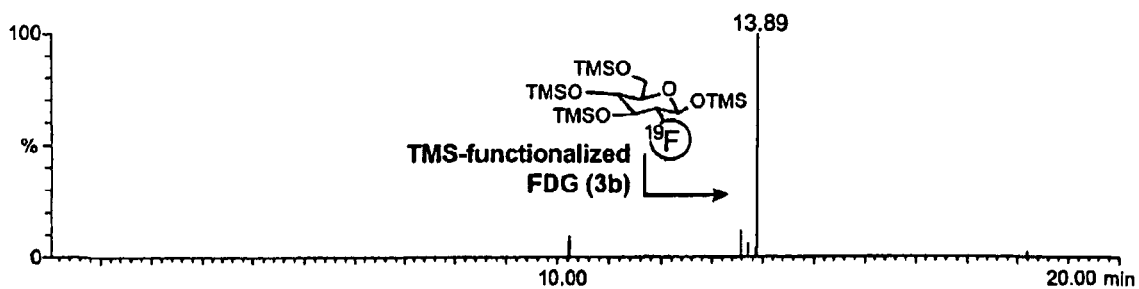

GC-MS analysis of the fluorinated intermediate 2b and [$^{19}$F]FDG (3b). The fluorinated intermediate 2b produced in the CRC was analyzed by GC-MS, indicating that the conversion yield for the fluorination reaction was about 95%. (FIG. 8B) Due to the low volatility of [$^{19}$F]FDG (3b), the [$^{19}$F]FDG (3b) obtained in the CRC had to be first treated by TMSCl prior to the GC-MS analysis. The GC-MS result indicated that the hydrolytic reaction of intermediate 2b results [$^{19}$F]FDG (3b) in >90% purity. (FIG. 9C)

1,3,4,6-Tetra-O-acetyl-2-[$^{19}$F]fluoro-2-deoxy-D-glucose (2b). A 40 nL anhydrous MeCN solution containing 1,3,4,6-tetra-O-acetyl-2-O-trifluoromethanesulfonyl-D-mannopyranose (mannose triflate) (1) (92 ng, $1.9\times10^{-10}$ mol) and 4,7,13,16,21,24-hexaoxa-1,10-diazabicyclo[8,8,8]hexacosane (Kryptofix 222) (364 ng, $9.6\times10^{-10}$ mol) was introduced into the reaction loop containing the dried KF which was concentrated by the previous fluoride concentration process. After all the valves around the reaction loop were closed, the CRC was heated at 100° C. for 30 seconds and maintained at 120° C. for 50 seconds. Meanwhile, the circulating pump was turned on to provide efficient mixing. After the chip was cooled down to 35° C., the reaction residue inside the loop was flushed out with MeCN for GC-MS analysis. Although an accurate reaction yield from GC-MS analysis could not be obtained it was obvious that the entire D-mannose triflate precursor 1 disappeared after the reaction and the fluorinated intermediate 2b was the only reaction product. (FIG. 9B)

2-Deoxy-2-[$^{19}$F]fluoro-D-glucose([$^{19}$F]FDG) (3b). After the fluorination step, 40 nL of HCl solution (3.0 N) was loaded into reaction loop. With all the valves closed and circulating pump running, the hydrolysis of the fluorinated intermediate 2 was finished in 1 minute at a temperature of 60° C. After cooling down to 35° C., the final product, [$^{19}$F] FDG (3b) was flushed out from the CRC by water. Final aqueous solution was removed in vacuo. Due to the low volatility, [$^{19}$F]FDG (3b) was derivatized with TMSCl prior to GC-MS analysis. The GC-MS result indicated that the hydrolytic reaction of intermediate 2b results [$^{19}$F]FDG (3b) in >90% purity. (FIG. 9C)

2-Deoxy-2-[$^{18}$F]fluoro-D-glucose ([$^{18}$F]FDG) (3a). 720 μCi of [$^{18}$F]fluoride in ca. 1 μL of [$^{18}$O]water was introduced into the fluoride concentration loop of the CRC. Because a relatively high loading rate (65 nL/sec) was applied, only 500 μCi of [$^{18}$F]fluoride (ca. $3.3\times10^{-11}$ mol, limiting reagent) was trapped in the column. An 18 nL of $K_2CO_3$ solution (0.25 M, $4.5\times10^{-9}$ mole) was introduced to fill the rectangular loop, and the circulating pump module was then turned on so that the $K_2CO_3$ solution could loop through the column continuously to produce a concentrated [$^{18}$F]KF solution. After circulation, 20 nL of $K_2CO_3$ solution was introduced into fluoride concentration loop to displace the concentrated [$^{18}$F]

fluoride solution into the ring-shaped reaction loop. With all the valves around reaction loop closed, the CRC was heated on a digitally controlled hotplate. The CRC was cooled down to 35° C. within 1 minute, and anhydrous MeCN (40 nL) was introduced into the reaction loop. The CRC was heated again to remove the water residue inside the loop. Kryptofix 222 (1.4 µg, 3.7×10$^{-7}$ mol) and the mannose triflate 1 (324 ng, 6.7×10$^{-10}$ mol) in anhydrous MeCN were introduced into the reaction loop. The CRC was heated with a gradient (100° C./30 seconds, 120° C./50 seconds). At the same time, the solution was actively mixed by the circulating pump to give [$^{18}$F]fluorinated intermediate 2a in the CRC. After cooling the CRC down to 35° C. within 1 minute, HCl aqueous solution (3.0 N) was introduced into the reaction loop. The mixture was mixed by the circulating pump for 1 min at 60° C. In this step, the intermediate 2a was hydrolyzed to yield the final product [$^{18}$F]FDG (3a). After cooling down to room temperature, the final product, 190 µCi of [$^{18}$F]FDG (3a) (ca. 1.25× 10$^{-11}$ mol, 38% yield) was flushed out from the chip by water for the analyses of radio-TLC (FIG. 10) and radio-HPLC. The analyses of radio-TLC and radio-HPLC suggested that the unpurified mixture obtained in the synthesis had a radiochemical purity of 97.6%.

Example 3

Second Generation CRC

This example describes a second generation CRC with the capacity to synthesize larger [$^{18}$F]FDG (3a) doses. This chip has a coin-shaped reactor (5 µL volume) equipped with a vacuum vent. It was used to synthesize 1.74 mCi [$^{18}$F]FDG (3a) sufficient for several mouse imaging experiments. From the purified and sterilized product (FIG. 5A), two doses (375 µCi and 272 µCi) were used for microPET- and microCT-based molecular imaging of two mouse models of cancer. Devices of this type can be used to synthesizing PET imaging agents on 100 mCi scale.

Fabrication of the second generation CRCs. The second generation CRCs (FIG. 11) were manufactured by a soft lithography method similar to the one described above. (Fabricated at Fluidigm Corp.) The main differences are (i) a third vent layer is located above the fluidic and control layers, (ii) all three layers of the CRC were made from 10:1 A/B PDMS and are held together by placing a 1-µm thick layer of PDMS B component between every two layers and (iii) the assembled device was mounted on a 2-inch silicon wafer. The dimensions of the arched flow channels are 250-µm wide and 45-µm tall. Only the water inlet channel is 300 µm wide. The reactor is 5 mm in diameter and 250 µm in height (with a total volume of 5 µL). The control channels form 250×250 µm intersections with flow channels. The vent is in the third layer with channels located 50 µm above the reactor 250 µm apart from each other and measuring 250×250 µm in cross-section.

Figure 5:
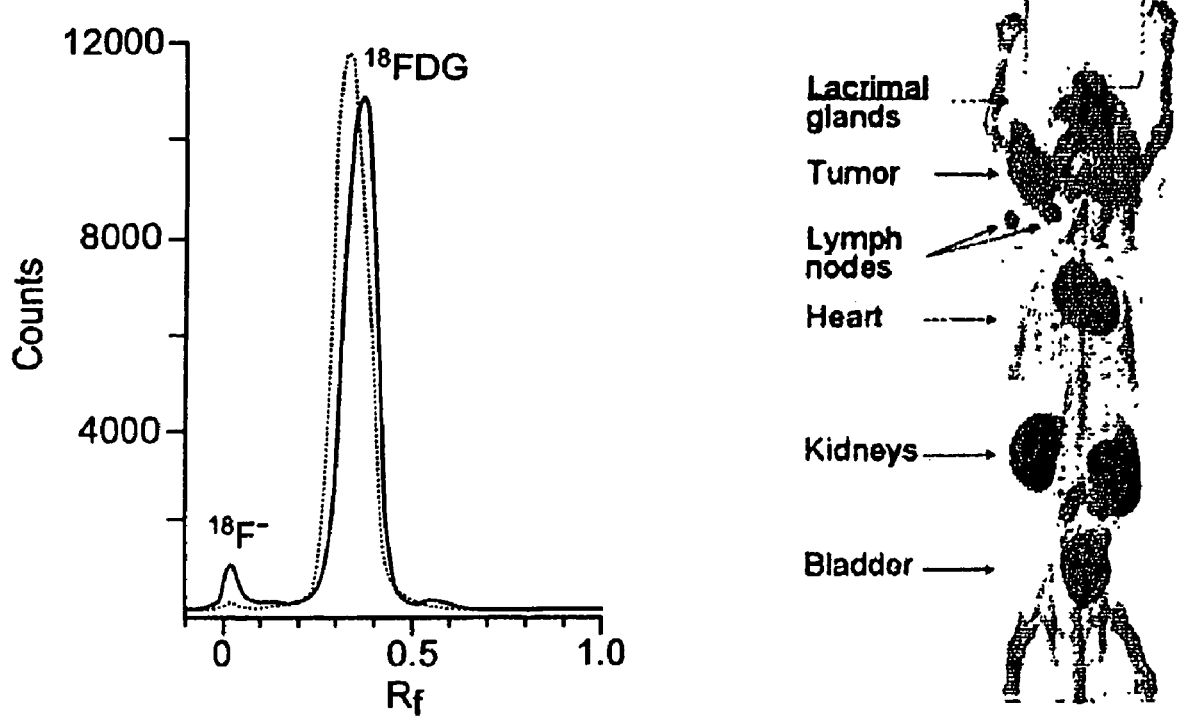
FIG. 5. (A) Analytical TLC profile of the unpurified mixture (blue curve) obtained upon the production of [$^{18}$F]FDG (3a) in the second generation CRC indicating that the radiochemical purity of the FDG production is up to 96.2%. The two peaks have $R_f$ values of 0.0 and 0.36 corresponding to [$^{18}$F]fluoride and [$^{18}$F]FDG (3a), respectively. After purification and sterilization, the [$^{18}$F]FDG (3a) (black curve) with 99.3% radiochemical purity was employed for mouse microPET/microCT imaging. (B) Projection view of microPET/microCT image of a tumor-bearing mouse injected with [$^{18}$F]FDG produced in a microfluidic chip. Organs visible are the bladder, kidneys, heart, tumor and two lymph nodes.

Chip II Description and Logic: In order to increase the amount of [$^{18}$F]FDG (3a) produced by a CRC to human dosage levels, the second generation CRCs were developed. Key features include (i) a 5-µL coin-shaped reactor, (ii) an overlaying vent channel connected to an external vacuum line, (iii) an external ion exchange column controlled by valves on the CRC, and (iv) a manifold for introducing the mannose triflate. The geometry of reactor inlets/outlets determines the fluid dynamics inside the CRC leading to better mixing during the reaction. The architecture of the new CRC also minimizes the number of valves. Currently the largest [$^{18}$F]FDG (3a) dose produced by this chip in a single run equals 1.74 mCi. This chip was used to generate [$^{18}$F]FDG (3a) for the mouse image presented in FIG. 12. The vacuum vent is advantageous during the solvent exchange steps. Full operation of the chip during [$^{18}$F]FDG (3a) synthesis is described in FIG. 12. [$^{18}$F]FDG (3a) is eluted as an acidic solution with 96% purity, which is first neutralized by 1.0 M NaHCO$_3$ and then passed through an alumina column (190 mg) to remove residual fluoride. The resulting solution exhibits 99% [$^{18}$F]FDG (3a) purity according to radio-TLC (FIG. 5A).

CRC II: Off-Chip Fluoride Concentration. For the operation of the new generation CRC, The [$^{18}$F]fluoride concentration was carried using the automatic Explora RN Nucleophilic [$^{18}$F]Fluorination system (Siemens Biomarker Solutions, Culver City, Calif.). An MP-1 resin cartridge was used to trap the dilute fluoride obtained from cyclotron. The activity was eluted with a solution of K$_2$CO$_3$ (3 mg) in water (400 µL). Upon water evaporation, the solution of Kryptofix 222 (20 mg) in MeCN (400 µL) was added followed by solvent evaporation. The residue was dissolved in anhydrous MeCN (200 µL) and the resulting solution of [$^{18}$F]Fluoride/K$_2$CO$_3$/K222 in MeCN containing 700 mCi of [$^{18}$F]fluoride was transferred from the Explora system via approximately 2 m of tubing to a conical vial (source vial) located near the CRC. Application of 10 psi of pressure to the source vial introduced concentrated [$^{18}$F]Fluoride/K$_2$CO$_3$/K222/MeCN mixture into the CRC.

Mouse Model. The tumor model used was a strongly immunogenic, non-metastasizing retrovirally-induced rhabdomyosarcoma (M-MSV/M-MuLV) (Fletcher et al., 2002, *Tetrahedron* 58:4735). MSV is a replication-defective, acutely transforming retrovirus carried with helper activity provided by M-MuLV, which encodes the gag, pol, and env components that are necessary for cell infection and replication (Worz et al., 2001, *Chemical Engineering Science* 56:1029). Rhabdomyosarcomas develop at the intramuscular inoculation site after a short latency period (7-10 days) and regress over a period of 4-5 wk following the induction of a strong immune reaction in immunocompetent adult mice. These lesions were characterized by a mixture of virus-infected myocytes and a large infiltrate of lymphocytes, granulocytes, and macrophages. Both cellular and humoral immune responses induced are dependent on presentation by H-2 D$^b$ alleles (Watts et al., 2003, *Current Opinion in Chemical Biology* 7:380). Rejection was mediated by CD8+ cytolytic T cells, which recognize peptides from the gag and env proteins of M-MuLV, and requires help from CD4+ T cells (Kobayashi et al., 2004, *Science* 304:1305; Chan et al., 2003, *Nano Letters* 3:199; Kawaguchi et al., 2005, *Angewandte Chemie-International Edition* 44:2413)

Mouse imaging. The tumor bearing mouse was injected with 272 microCi of FDG via tail vein. Following 1-h uptake and non-specific clearance, the mouse was imaged for 15 minutes in a Focus 220 microPET, followed by a microCT scan (Siemens, Knoxville, Tenn.). MicroPET and microCT images were reconstructed using MAP and Fledkamp to resolutions of 1.2 mm and 0.4 mm respectively, then fused using AMIDE image visualization software. See FIG. 5B for result.

Example 4

SYNTHESIS OF 2-(1-(6-[(2-[$^{18}$F]FLUORO-ETHYL)(METHYL)AMINO]-2-NAPHTHYL) (FDDNP)

This example describes the synthesis of 2-(1-(6-[(2-[$^{18}$F] fluoro-ethyl)(methyl)amino]-2-naphthyl)(FDDNP), a molecular imaging probe utilized in diagnosis of Alzheimer's disease. See, Agdeppa et. al., 2003, *Mol. Imag. Biol.* 5:404. The chemical steps to produce [$^{18}$F]FDDNP were completed within 20 minutes and resulted in >8 µCi product. Similar results were observed across multiple runs.

The chip design for FDDNP synthesis included a loop-type reactor, without an anion exchange column (see FIG. 14 and accompanying legend). The fabrication of the CRC for synthesis of [$^{18}$F]FDDNP was generally as described above in Example 2. All reagents with the exception of 2-(1-{6-[(2-(p-Toluenesulfonyloxy)ethyl)(methyl)amino]-2-napthyl}ethylidine)malononitrile (provided courtesy of MTI) were purchased from SIGMA-ALDRICH. [$^{18}$F]fluoride (limiting reagent) in about 1 µL of [$^{18}$O]water was used in the synthesis. The Kryptofix 222 plus 2-(1-{6-[(2-(p-toluenesulfonyloxy)ethyl)(methyl)amino]-2-napthyl}ethylidine)malononitrile ("precursor") solution is made by adding 10 mg Kryptofix and 14 micrograms precursor to 100 microliters anhydrous MeCN. A four-fold higher concentration of precursor has also been used, with similar results.

The FDDNP synthesis in the CRC is based on two sequential synthetic processes starting from (i) exchange of solvent from water to acetonitrile of dilute fluoride, followed by (ii) fluorine substitution reaction of the 2-(1-{6-[(2-(p-toluenesulfonyloxy)ethyl)(methyl)amino]-2-napthyl}ethylidine) malononitrile.

For the synthesis, 200 µCi of [$^{18}$F]fluoride in about 1 µL of [$^{18}$O]water plus $K_2CO_3$ (0.05 M) was introduced into the CRC. Because of the limited volume (350 nL) inside the reaction chamber, only 70 µCi of [$^{18}$F]fluoride (ca. $4.6 \times 10^{-12}$ mol, limiting reagent) was inside the reaction loop. With all the valves around reaction loop closed, the CRC was heated on a digitally controlled hotplate to evaporate the water. The CRC was cooled down to 35° C. within 1 minute, and anhydrous MeCN (350 nL) was introduced into the reaction loop. The CRC was heated again to remove the water residue inside the loop. Kryptofix 222 and 2-(1-{6-[(2-(p-toluenesulfonyloxy)ethyl)(methyl)amino]-2-napthyl}ethylidine)malononitrile in anhydrous MeCN were introduced into the reaction loop. The CRC was heated with a gradient (100° C./30 seconds, 120° C./180 seconds). At the same time, the solution was actively mixed by the circulating pump to give the final product. After cooling the CRC down to room temperature within 1 minute, anhydrous MeCN was introduced into the reaction loop and actively mixed by the circulation pumps to dissolve and wash off any product that might have attached to the wall of the reaction chamber. Lastly, anhydrous MeCN was used to flush the product off the chip for the analyses of radio-TLC. Analyses of radio-TLC showed that the unpurified mixture obtained contained [$^{18}$F]FDDNP at a radiochemical purity of 11.6%.

Example 5

Design, Fabrication and Use of a Microfluidic Device

This Example describes an early synthesis of FDG using a microfluidic device.

CRC Fabrication

The three-layer PDMS-based integrated CRCs were built using soft lithography method (Liu et al., 2003, "Solving the "world-to-chip" interface problem with a microfluidic matrix" *Analytical Chemistry* 75:4718-23. Two different molds were first fabricated by photolithographic processes for production of fluidic channels and the control channels located in each layer of the PDMS-based CRC.

The mold applied for fabrication of fluidic channels is fabricated by a two-step photolithographic process. In principle, the thickness of photoresist determines the height of the fluidic/control channels. During the first step a 45-µm thick negative photoresist (SU8-2025) was spin coated on to a silicon wafer. After UV exposure and development a square-profiled pattern for a column module was obtained. In the following step, a second layer of 45 µm thick positive photoresist (AZ 100XT PLP) was then spin coated on the same wafer. An alignment process was performed prior of the UV exposure to ensure a good match between the first and second layers of fluidic channel. Once the positive photoresist was developed, the wafer was heated above the glass transition temperature of positive photoresist's. As a result, the surface profile of the patterned positive photoresist was transform into a round profile while the profile of the negative photoresist remains intact. It is important to note that the heights and widths of the column and fluidic channels have to be well-matched. For this device, a channel height of 45 µm and width of 200 µm is used. The dimensionalities of column and fluidic channels were determined on the basis of reaction volume and flow rate.

Mold applied for the control channels is made by introducing a 25 µm-thin negative photoresist (SU8-2025) pattern on a silicon wafer. The height of the control layer should be above one tenth of the width of control channel to avoid collapses of valves during the CRC fabrication. The width of the control channels is very flexible. In order to achieve reliable performance of each valve, the width of the control channel was set to be 250 µm at the certain sections where the valve modules are located. To avoid parasitic valves from forming, width of the control channel are kept between 25 µm to 50 µm in all other areas. The width of control layer is inversely related to actuation pressure of the valves (Studer et al., 2004, "Scaling properties of a low-actuation pressure microfluidic valve." *J. Applied Physics* 95:393-398).

Figure 15:
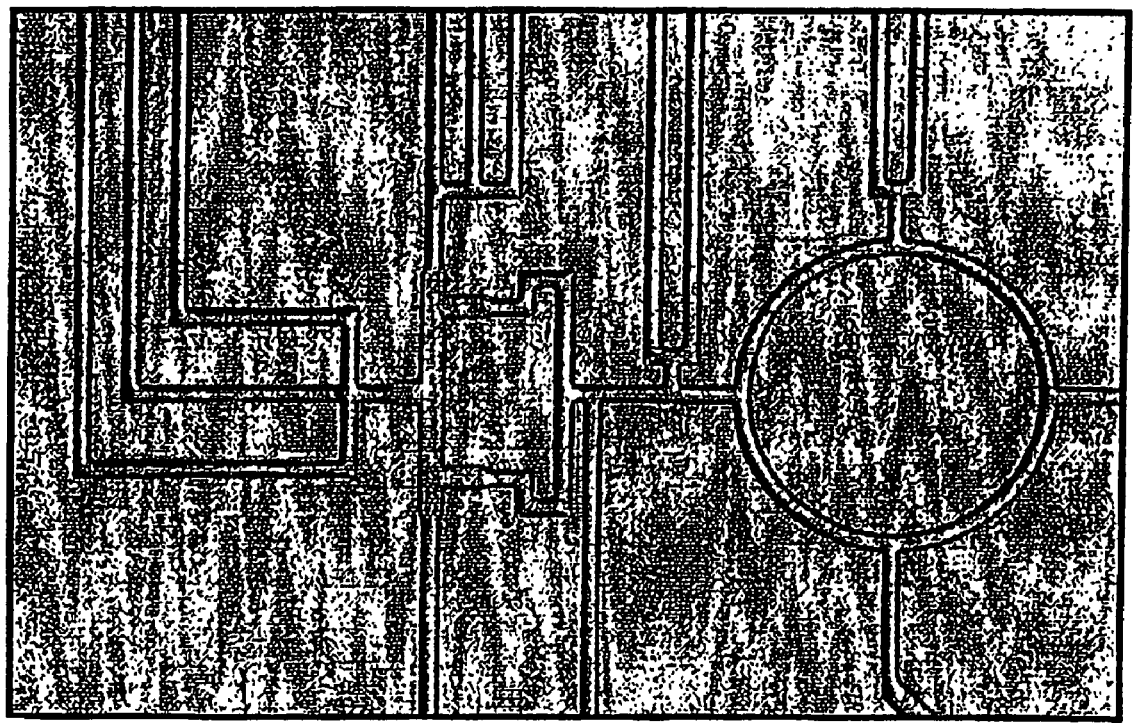
FIG. 15 shows PDMS-based chemical reaction circuits for FDG synthesis.

Before fabricating the device, both the fluidic and control molds are exposed to vapor of trimethylchlorosilane (TMSCl) for 2-3 minutes. A well-mixed PDMS (GE RTV 615 A and B in 5 to 1 ratio) was then poured onto the fluidic mold located in a petri dish to produce a 5 mm-thick fluidic layer. Another portion of PDMS (GE RTV 615 A and B in 20:1 ratio) is spin-coated onto the control mold (1600 rpm, 60 s, ramp 15 s) to give a control layer. The thick fluid layer and thin control layer are cured in an 80° C. oven for 150 minutes and 50 minutes, respectively. After incubation, the thick fluidic layer is peeled off the mold, and holes were introduced onto the fluidic layer for access of reaction solutions. This layer is then trimmed, cleaned and aligned onto the thin control layer. After backing at 80° C. for another 90 minutes, the assembled layer was peeled off the control mold, and: another set of holes are punched for access of control channels. Finally, this assembled layer is then placed on top of a glass slide that is coated with a 20:1 ratio of GE RTV 615 A and B (1600 rpm, 60 s, ramp 15 s) that had been cured for 45 minutes in the oven. The device was ready for use after a oven overnight incubation in the oven. FIG. 15 shows a PDMS-based chemical reaction circuits for FDG synthesis.

FDG Synthesis

Three sequential synthetic processes of FDG in integrated CRCs. Similar to the conventional synthetic processes utilized for a laboratory automation system, FDG can be produced in the integrated CRC by three sequential steps, including (i) concentration of fluoride, (ii) fluorination and (iii) hydrolysis.

(1) Concentration of dilute fluoride: By using an anion exchange column (FIG. 13) dilute fluoride (1 ppm with the volume raging form 10 to 500 μL) was concentrated in the square-shape mixer to obtain a three to four orders more concentrate KF solution with a volume of 45 nL.

In order to perform the concentration of dilute fluoride (first step of FDG synthesis), a column module capable of fluoride ion extraction was incorporated into the CRC. An ion exchange column (FIG. 13) was constructed by trapping ion exchange beads in a fluid channel isolated with five sieve valves. A sieve valve composed of a square-profile fluidic line and a regular control membrane is different from a normal valve based on a round-profile fluidic line (see FIGS. 3A and B). In general, when valves operate, the valve membranes deflect in an elliptic shape. In the case of normal valve, the deflected membrane is fully compliant to the round-profile fluidic channel lead to complete close of the valve. For a sieve valve, a deflected membrane partially closes the valve, generating two small gaps the two channel edges of the square-profile channel. When aqueous solution containing suspended beads in appropriate sizes is introduced into the fluidic chambers, the beads are trapped by the sieve valves while the solution is allowed to pass through the closed sieve valve.

Source 15Q anion exchange resins (2 pm, Amersham Bioscience) was first confined inside the column module. A 1.0 M solution of $KHCO_3$ was then passed through the column to convert the resins into the saturated bicarbonate forms. In order to remove the excess bicarbonate anions that are not coupled with the quaternary ammonium groups on the beads surface deionized water was subsequently flown through the column before used for fluoride concentration.

Figure 16A:
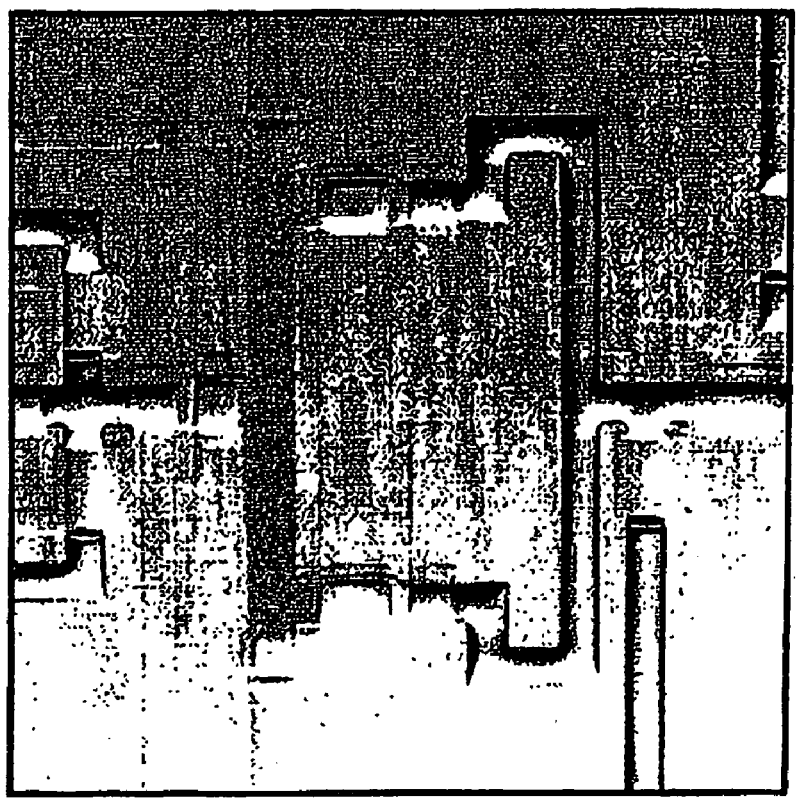
FIG. 16. (A, top) An optical micrograph of a square shaped concentration loop containing an anion exchange column, a pump and a concentration loop for concentration of dilute fluoride (B, bottom) An optical micrograph of a round-shaped reaction chamber containing a reaction loop and a pump, used for both fluorination and hydrolysis reactions.

A 200 μL aqueous solution containing cold fluoride ($^{19}F$—) was passed through the ion exchange column. The negatively charged fluoride ions were then exchanged onto the resin surfaces to replace $HCO_3$ counter ions. After the fluoride solution has completely passed through, 45 nL of 0.02 M solution of $K_2CO_3$ was introduced into the first (square-shaped, FIG. 16A) reaction loop. The pump module was then turned on for two minutes so $K_2CO_3$ solution looped through the column continuously. As a result, the surface-trapped fluoride ions were eluted off the column to a KF in solution which is ready to be transferred into the reaction loop for further process.

(2) Fluorination (synthesis of 1,3,4,6-tetra-O-acetyl-2-fluoro-2-deoxy-D-glucose): The synthesis of 1,3,4,6-tetra-O-acetyl-2-fluoro=2-deoxy-D-glucose from 1,3,4,6-tetra-O-acety Pl-2-trifluoro-methane-sulfonyl-D-manno-pyranose (mannose triflate) can be adapted from a previously developed method (Kikutani et al., 2004, *Macromolecular Rapid Communications* 25:158). In this case, mannose triflate was reacted with the complex of potassium fluoride (KF) and 4,7,13,16,21,24-hexaoxa-1,10-diazabicyclo[8,8,8]hexacosane (Kryptofix 222) in the anhydrous acetonitrile solution in the second (round-shaped, FIG. 16B) reaction chamber. Following the concentration of fluoride, water in the concentrated KF aqueous solution obtained from first reaction chamber has to be removed. In the PDMS-based CRCs, removal of water was achieved by heating the CRCs directly on a hot plate at 120° C. for 2 minutes, whereupon all valves associated with the reaction loop were closed. In order to ensure the complete removal of water residue, the loop was filled with dry acetonitrile and then heated to 150° C. for 1 minute. It is important to note that moisture and acetonitrile vapor can easily penetrate PDMS materials since the material is highly permeable to gases. In a conventional automation system the removal of water in KF solution was carried out by heating the solution under a nitrogen flow, which is less efficient and much more time-consuming when compared with the same process in the PDMS-based CRC.

Figure 16B:
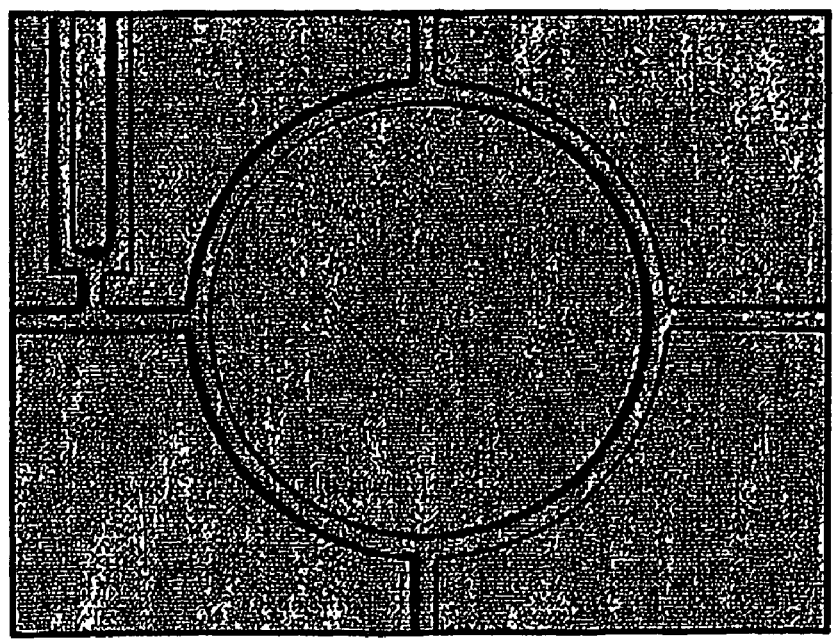

Immediately after the removal of water, 17 nL of acetonitrile solution containing Kryptofix 222 (1.7 μg) and mannose initiate (272 ng) was introduced into the reaction loop from the top fluidic channel of reaction loop presented in FIG. 16B. After closing all inlet/outlet valves, the inhomogeneous reaction mixture was then circulated inside the reaction loop by using the peristaltic pump located on the up-left portion of the loop; at the same time, the CRC was healed on a hotplate at 150° C. for 30 seconds. At this stage, the resulting intermediate was analyzed by a GC-MS. At the temperature covering 60 to 120° C., the respective yields of the fluorination process were obtained in the range of 0.6% to 16.5%. At 150° C., the GC-MS indicated that all the starting material has been transformed after reaction time of 30 seconds.

Figure 17:
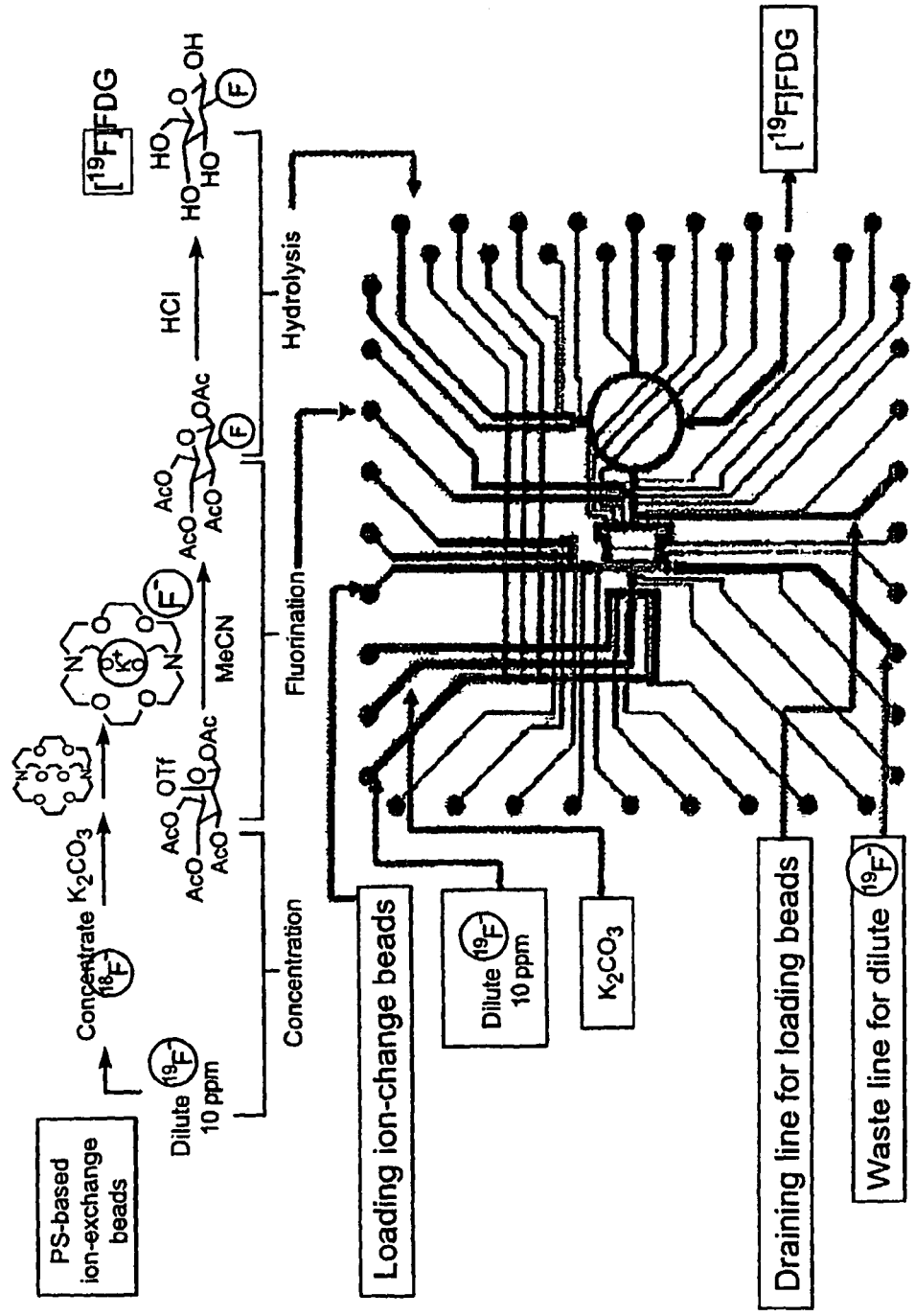
FIG. 17 is a graphical representation summarizing sequential FDG synthesis in a chemical reaction circuit.

(3) Hydrolysis (hydrolysis of 1,3,4,6-tetra-O-acetyl-2-fluoro-2-deoxy-D-glucose to FOG: After the fluorination reaction, acetonitrile was removed by direct evaporation through PDMS materials prior to the following hydrolysis reaction. 17 nL 6M. HCl solution was injected into the CRC, and the hydrolysis of 1,3,4,6-tetra-O-acetyl-2-fluoro-2-deoxy-D-glucose was carried out by at room temperature. Again, with the assistance of peristaltic pump the hydrolysis reaction was finished in 4 minutes. FIG. 17 summarizes the overall three sequential reactions in the CRC. where fluoride concentration, fluorination and hydrolysis are labeled in red, blue and green, respectively. In addition, the direction for introducing solutions, beads and reagents are Indicated by arrows.

In a laboratory automation system, it takes about 40 minute to complete the processes of fluorination and hydrolysis for FDG synthesis. By using our prototype CRC, these sequential synthetic processes can completed within 16 minutes, and we anticipate that the production time can shorten to 5 minutes or less when this CRC is fully automated. A side-by-side comparison based on respective steps for a conventional method and the CRC are outlined in Table 2.

Table 2 shows the reaction times and conditions of conventional and microfluidic preparations of FDG. FDG synthesis in microfluidic device took much less time than conventional method mainly due to the faster reaction speed and quicker solvent evaporation (water and acetonitrile) in microfluidic chips. Multi-steps organic reactions can be automatically finished step by step by controlling the pumps and valves which can be fabricated in the PDMS based chips.

TABLE 1

| Conventional Method mg compounds in ml solvent | | Time | Microfluidic ng compounds in nL solvent | Time (this example) | Time (projected) |
| --- | --- | --- | --- | --- | --- |
| Step 1 | Addition of $K_2CO_3$ in $H_2O$ | 0:04:00 | Addition of 0.24 M $K_2CO_3$ to concentrating loop | 0:00:30 | :00:20 |
| Step 2 | Addition of Kryptofix in MeCN and evaporation | 0:06:00 | elution of 18F off ion exchange column | 0:02:00 | 0:01:00 |
| Step 3 | Cooling of solution | 0:00:30 | Transfer of concentrated 18F into 2nd reaction loop | 0:02:00 | 0:01:00 |
| Step 4 | Addition MeCN | 0:04:00 | Evaporation of $H_2O$ and Addition of MeCN | 0:05:00 | 0:02:00 |

TABLE 1-continued

| Conventional Method mg compounds in ml solvent | | Time | Microfluidic ng compounds in nL solvent | Time (this example) | Time (projected) |
|---|---|---|---|---|---|
| Step 5 | Addition of Triflate suspended in MeCN | 0:05:00 | Addition of triflate and Kryptofix suspended in MeCN | 0:02:00 | 0:00:30 |
| Step 6 | Fluorination of precursor | 0:04:00 | Fluorination of triflate heat it up to 150 C.° | 0:00:30 | 0:00:30 |
| Step 7 | Hydrolysis (1M HCl) | 0:16:00 | Hydrolysis (6M HCl) | 0:04:00 | 0:00:30 |
| Total Time | | 39.30 | | 16:00 | 5:50 |

Example 6

Design, Fabrication and Use of a Microfluidic Device With an Off-Chip Column

Figure 18:
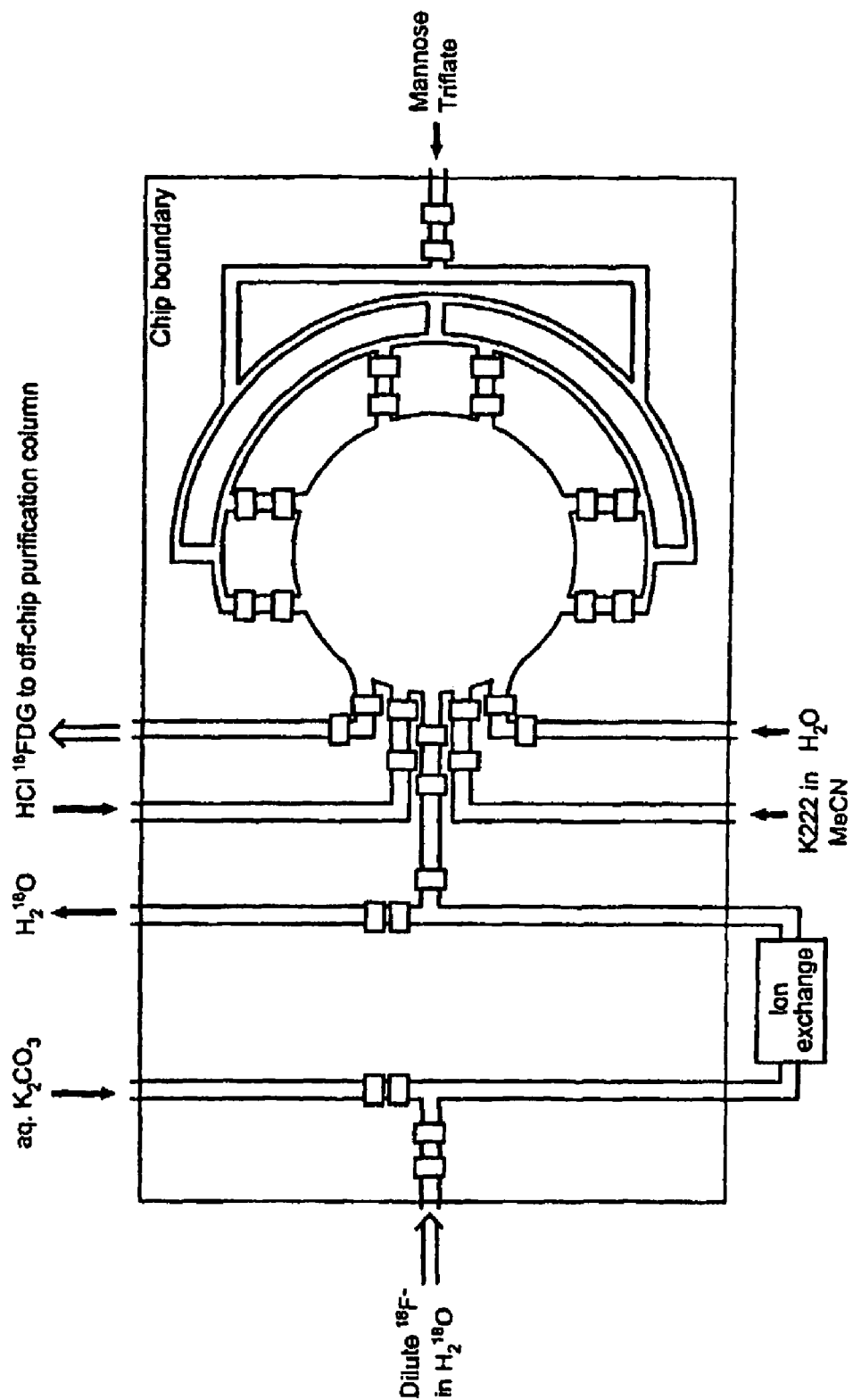
FIG. 18 shows a chip with a coin-shaped reactor and an "off-chip" chromatography column.

FIG. 18 shows a chip with a coin-shaped reactor and off-chip anion exchange column. Valves are represented by red rectangles. All inlet/outlet channels are the same size except for the larger inlet for the water (product elution). The solution distributed through the manifold travels the same distance from the origin to the chamber through all 6 ports.

The dilute [F-18] solution is passed through the column and trapped by the resin off-chip. This process is controlled by on-chip valves on short channels connecting source of [F-18] to the column and the latter to the collection vial for $H_2^{18}O$.

The aqueous $K_2CO_3$ solution routed through the chip and controlled by on-chip valves is then passed through the off-chip ion exchange column to elute the [$^{18}$F] straight into the reactor on the chip. At this point water can be evaporated leaving behind $K^{18}F$ and $K_2CO_3$ salts along with some residual moisture. (The vacuum vent is used in this and all subsequent evaporation steps. As a result the water vapor permanently leaves the chip rather than staying condensed in the chip's matrix. In order to remove this moisture by forming an azeotrope with MeCN and solubilize $K^{18}F$ in organic solvens, the chamber is now filled with a MeCN solution of Kryptofix222, followed by its evaporation. At this point mannose triflate will be introduced into the reactor through a 6-port manifold. Actuating the mixer at an elevated temperature should allow for efficient fluorination. It is also possible to achieve fluorination at ambient temperature. Upon completion of the fluorination, the solvent is partially removed by evaporation. If MeCN is evaporated completely, [F-18]FTAG forms a thick oily residue distributed unevenly throughout the reactor. This residue is very difficult to dissolve in an aqueous solution in the next step. 3N HCl solution is introduced to the half-empty reactor through one channel until the reactor is full. Efficient mixing with MeCN solution of [F-18]FTAG is achieved quickly since it is facilitated at the interface of two solutions by swirling resulting from an acid-base reaction (with $K_2CO_3$). Heating at 60° C. followed by 75° C. allows hydrolysis to proceed to completion by gradual (but fast) removal of MeCN resulting in an aqueous solution of [F-18] FDG. Two ways for collecting the product from the reaction chamber after deprotection are proposed: 1) Flushing the product out through the tangential exit channel by introducing water into the reactor through another tangential channel allows the flow to follow the trajectory along the far wall of the chamber or removing product in a two-step process involving, first, closing off the exit from the radiator will send $N_2$ pressure into the reactor through the gas permeable membrane and, second, activating the mixer shown in FIG. 19.

The product solution is delivered to a vial containing 2M $KHCO_3$ solution to neutralize HCl. Afterwards the contents of the vial are passed through an alumina column resulting in 99.3% radio-pure [F-18]FDG.

Although the present invention has been described in detail with reference to specific embodiments, those of skill in the art will recognize that modifications and improvements are within the scope and spirit of the invention, as set forth in the claims which follow. All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. A method for solvent exchange using a microfluidic device, said method comprising:
   i) providing a microfluidic device comprising a reactor, wherein said reactor
      a) is configured to fluidically communicate with at least one microfluidic channel;
      b) is configured to be fluidically isolated; and
      c) is defined by a wall at least a portion of which is permeable to a gas but substantially impermeable to a liquid corresponding to the gas;
   ii) introducing into the reactor a first solvent system comprising a first reactant;
   iii) fluidically isolating the reactor;
   iv) allowing some or all of the first solvent system to evaporate from the fluidically isolated reactor through said gas permeable wall or wall portion while retaining the first reactant in the reactor; and then
   v) introducing into the reactor a second solvent system different from the first solvent system.

2. A method for removing a solvent system from a microfluidic device comprising a reactor, wherein said reactor
   a) is configured to fluidically communicate with at least one microfluidic channel;
   b) is configured to be fluidically isolated; and
   c) is defined by a wall at least a portion of which is permeable to a gas but substantially impermeable to a liquid corresponding to the gas;
   the method comprising:
   i) combining in the reactor a first solvent system comprising a first solute and a second solvent system comprising a second solute;
   ii) fluidically isolating the reactor; and
   iii) allowing at least 25% of the volume of the combined solvent systems in the reactor to evaporate through said gas permeable wall or wall portion, so that the concentration of the first solute, the second solute, and/or a reaction product formed from either or both of said solutes increases in the volume that remains.

3. The method of claim 1 wherein the second solvent system comprises a second reactant, and wherein the first reactant and the second reactant are compounds that chemically react, under reaction conditions, to generate a first reaction product.

4. The method of claim 3 further comprising maintaining the reactor in a fluidically isolated state for a time and under conditions sufficient for the first reaction product to accumulate in the reactor.

5. A method for carrying out a chemical reaction using a microfluidic device, said method comprising:
i) providing a microfluidic device comprising a reactor, wherein said reactor
   a) is configured to fluidically communicate with at least one microfluidic channel;
   b) is configured to be fluidically isolated; and
   c) is defined by a wall at least a portion of which is permeable to a gas but substantially impermeable to a liquid corresponding to the gas;
ii) introducing into the reactor a first solvent system comprising a first reactant;
iii) introducing into the reactor a second solvent system comprising a second reactant so as to form a reaction solvent system comprising the first and second reactant,
iv) maintaining the reactor in a fluidically isolated state for a time and under conditions sufficient for the first reactant and the second reactant chemically react in the reactor to generate a product; and
v) allowing some or all of the reaction solvent system to evaporate through said gas permeable wall or wall portion while retaining the product in the reactor.

6. The method of claim 4 further comprising
i) fluidically joining the reactor and a microfluidic channel;
ii) introducing into the reactor a third solvent system comprising a third reactant and/or a catalyst by way of said microfluidic channel, while retaining the first product in the reactor;
iii) maintaining the reactor in a fluidically isolated state for a time and under conditions sufficient for a second reaction product to accumulate in the reactor as a result of introducing the third solute.

7. The method of claim 5 further comprising
i introducing into the reactor a solution comprising a third reactant and/or a catalyst, while retaining the product in the reactor.

8. The method of claim 5 wherein the reactor is coin-shaped.

9. The method of claim 5 wherein the first reactant or the second reactant is purified or concentrated in an on-chip microfluidic separation column prior to being introduced into the reactor.

10. The method of claim 5 wherein the microfluidic device comprises a separation column comprising a stationary phase;
said method comprising:
(i) introducing into the separation column a solution containing the first reactant, and adsorbing the first reactant to the stationary phase;
(ii) eluting the first reactant from the stationary phase in a solvent system;
(iii) introducing said solvent system comprising said first reactant into the reactor.

11. A method according to claim 5 for carrying out a series of chemical reactions using a microfluidic device, said method comprising
i) providing a microfluidic device comprising a reactor, wherein said reactor
   a) is configured to fluidically communicate with at least one microfluidic channel;
   b) is configured to be fluidically isolated; and
   c) is defined by a wall at least a portion of which is substantially impermeable to liquid water and liquid acetonitrile, but permeable to water vapor and acetonitrile vapor;
ii) introducing into the reactor an aqueous solution comprising [$^{18}$F]fluoride;
iii) introducing into the reactor an acetonitrile solution comprising mannose triflate;
iv) fluidically isolating the reactor;
v) reacting the [$^{18}$F]fluoride and the mannose triflate to produce 2 deoxy-2-[$^{18}$F]fluoro-1,3,4,6-tetra-O-acetyl beta-D-glucose (FTAG);
vi) fluidically joining the reactor and a microfluidic channel;
vii) introducing aqueous HCl into the reactor while retaining the FTAG in the reactor;
viii) fluidically isolating the reactor;
ix) hydrolyzing the FTAG to produce 2 deoxy-2-[$^{18}$F] fluoro-D-glucose (FDG).

12. A method for synthesizing a radiolabeled product in a microfluidic environment in accordance with the method of claim 1, comprising mixing a radiolabeled reactant with a precursor reactant compound to produce a radiolabeled product, wherein said mixing and reacting occurs in a microfluidic reactor and wherein the radiolabled reagent is introduced into the reactor in a first solvent the precursor reactant is introduced in a second solvent that is different from the first and the reactor is fluidically isolated following introduction of the radiolabled reagent and the precursor reagent.

13. The method of claim 12, further comprising deprotection or chemical modification of the radiolabeled product to produce a radiodiagnostic agent or radiotherapeutic agent.

14. The method of claim 13 wherein the radiolabeled product is a radiolabeled molecular imaging probe.

15. The method of claim 14 wherein the precursor reactant is D-mannose triflate; 2-(1-{6-[(2-[(p-toluenesulfonyloxy) ethyl)(methyl)amino]-2-naphthyl}ethylidine)malononitrile; N-Boc-5'-O-dimethoxytrityl-3'-O-(4-nitrophenylsulfonyl)-thymidine; N2-(p-anisyldiphenylmethyl)-9-[(4-p-toluenesulfonyloxy)-3-(p-anisyldiphenylmethoxymethyl) butyl]guanine; N2-(p-anisyldiphenylmethyl)-9-[[1-[(β-anisyldiphenylmethoxy)-3-(p-toluenesulfonyloxy)-2-propoxy]methyl]guanine; 8-[4-(4-fluorophenyl)-4,4-(ethylenedioxy)butyl]-3-[2'-(2,4,6-trimethylphenylsulfonyloxyethyl)]-1-phenyl-1,3,8-triazaspiro[4.5]decan-4-one; 5'-O-Boc-2,3' anhydrothymidine; N-[2-[4-(2-methoxyphenyl)-1-piperazinyl]ethyl]-4-nitro-N2-pyridinyl-benzamide; 1,2-bis(tosyloxy)ethane and N,N-dimethylethanolamine; ditosylmethane or N,N-dimethylethanolamine.

16. The method of claim 5 wherein the reactor does not form a closed path, has a liquid capacity of from 5 microliters to 10 microliters, is configured to fluidically communicate with at least one microfluidic flow channel that is a distribution manifold, and is defined by a wall at least a portion of which is permeable to a gas but substantially impermeable to a liquid corresponding to the gas, wherein said liquid is selected from the group consisting of water, acetonitrile, and mixtures of water and acetonitrile.

17. The method of claim 1, wherein the microfluidic device comprises vent channels positioned adjacent to said gas permeable wall or wall portion so as to facilitate withdrawal of gas from the reactor.

18. The method of claim 1, wherein step (iv) comprises heating the first solvent system in the reactor.

19. The method of claim 1, wherein step (iv) comprises reducing the ambient pressure.

20. The method of claim 5, wherein step (iv) comprises heating the mixture formed in the reactor as a result of steps (ii) and (iii).

* * * * *

UNITED STATES PATENT AND TRADEMARK OFFICE
CERTIFICATE OF CORRECTION

PATENT NO. : 8,206,593 B2  Page 1 of 1
APPLICATION NO. : 11/792168
DATED : June 26, 2012
INVENTOR(S) : Chung-cheng Lee et al.

It is certified that error appears in the above-identified patent and that said Letters Patent is hereby corrected as shown below:

In the Claims Section,

Col. 59 Page 55, claim 7, line 40-41, delete
"claim 5 further comprising i introducing into"
and insert
--claim 5 further comprising introducing into--
Col. 60 Page 55, claim 11, line 29, delete
"the FTAG to produce 2 deoxy-2"
and insert
--the FTAG to produce 2-deoxy-2"--

Signed and Sealed this
Twenty-eighth Day of August, 2012

David J. Kappos
*Director of the United States Patent and Trademark Office*